(12) United States Patent
Kelly et al.

(10) Patent No.: US 7,297,700 B2
(45) Date of Patent: Nov. 20, 2007

(54) BICYCLOHETEROARYL COMPOUNDS AS P2X7 MODULATORS AND USES THEREOF

(75) Inventors: Michael G. Kelly, Thousand Oaks, CA (US); John Kincaid, San Mateo, CA (US)

(73) Assignee: Renovis, Inc., South San Francisco, CA (US)

( * ) Notice: Subject to any disclaimer, the term of this patent is extended or adjusted under 35 U.S.C. 154(b) by 2 days.

(21) Appl. No.: 11/384,045

(22) Filed: Mar. 17, 2006

(65) Prior Publication Data

US 2006/0217448 A1 Sep. 28, 2006

Related U.S. Application Data

(60) Provisional application No. 60/753,194, filed on Dec. 22, 2005, provisional application No. 60/721,390, filed on Sep. 28, 2005, provisional application No. 60/712,778, filed on Aug. 31, 2005, provisional application No. 60/710,077, filed on Aug. 22, 2005, provisional application No. 60/709,186, filed on Aug. 18, 2005, provisional application No. 60/664,903, filed on Mar. 24, 2005.

(51) Int. Cl.
| | |
|---|---|
| A01N 43/54 | (2006.01) |
| A01N 43/90 | (2006.01) |
| A61K 31/517 | (2006.01) |
| A61K 31/519 | (2006.01) |
| C07D 239/00 | (2006.01) |
| C07D 239/70 | (2006.01) |

(52) U.S. Cl. ............................. 514/258.1; 544/253
(58) Field of Classification Search ............ None
See application file for complete search history.

(56) References Cited

U.S. PATENT DOCUMENTS

| 5,034,393 A * | 7/1991 | Hackler et al. ............ 514/262.1 |
| 2003/0191143 A1 | 10/2003 | Pitts et al. |
| 2005/0038023 A1 | 2/2005 | Bebbington et al. |
| 2005/0165032 A1 | 7/2005 | Norman et al. |
| 2005/0277643 A1 | 12/2005 | Kelly et al. .................. 514/243 |

FOREIGN PATENT DOCUMENTS

| JP | 04224580 | 8/1992 |
| WO | WO98/37079 | 8/1998 |
| WO | WO99/21836 | 5/1999 |
| WO | WO 01/32632 | 5/2001 |
| WO | WO 02/22602 | 3/2002 |
| WO | WO 02/22604 | 3/2002 |
| WO | WO 02/50065 | 6/2002 |
| WO | WO 02/053558 | 7/2002 |
| WO | WO 02/057259 | 7/2002 |
| WO | WO 02/059111 | 8/2002 |
| WO | WO 02 062789 | 8/2002 |
| WO | WO 00/59510 | 10/2002 |
| WO | WO 02/087513 | 11/2002 |
| WO | WO 03/049739 | 6/2003 |
| WO | WO 03/062225 | 7/2003 |
| WO | WO 03/076427 | 9/2003 |
| WO | WO 03/104230 | 12/2003 |
| WO | WO 2004/007468 | 1/2004 |
| WO | WO 2004/072086 | 8/2004 |
| WO | WO 2004/087056 | 10/2004 |
| WO | WO 2005/005397 | 1/2005 |
| WO | WO 2005/014558 | 2/2005 |
| WO | WO 2005/042537 | 5/2005 |
| WO | WO 2005/049033 | 6/2005 |
| WO | WO 2005/066171 | 7/2005 |
| WO | WO 2006/035061 | 4/2006 |
| WO | WO 2006/062981 | 6/2006 |
| WO | WO 2006/074057 | 7/2006 |

OTHER PUBLICATIONS

Chan, WN et al. Evaluation of a Series of Anticonvulsant 1,2,3,4-Tetrahydroisoquinolly -benzamides, Bioorganic & Medicinal Chemistry, 2000, vol. 8, pp. 2085-2094.

* cited by examiner

*Primary Examiner*—Zachary C. Tucker
*Assistant Examiner*—Erich A. Leeser
(74) *Attorney, Agent, or Firm*—Klauber & Jackson LLC

(57) ABSTRACT

Bicycloheteroaryl compounds are disclosed that have a formula represented by the following:

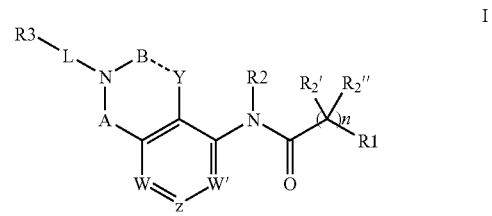

The compounds may be prepared as pharmaceutical compositions, and may be used for the prevention and treatment of a variety of conditions in mammals including humans, including by way of non-limiting example, pain, inflammation, traumatic injury, and others.

37 Claims, No Drawings

BICYCLOHETEROARYL COMPOUNDS AS P2X$_7$ MODULATORS AND USES THEREOF

CROSS REFERENCE TO RELATED APPLICATIONS

The present application claims the priority of co-pending provisional applications U.S. Ser. No. 60/664,903, filed on Mar. 24, 2005; U.S. Ser. No. 60/709,186 filed on Aug. 18, 2005; U.S. Ser. No. 60/710,077 filed on Aug. 22, 2005; U.S. Ser. No. 60/712,778 filed on Aug. 31, 2005; U.S. Ser. No. 60/721,390 filed on Sep. 28, 2005; and U.S. Ser. No. 60/753,194 filed on Dec. 22, 2005. The disclosures of all of the aforementioned applications are incorporated by reference herein in their entireties. Applicants claim the benefits of these applications under 35 U.S.C. §119(e).

FIELD OF THE INVENTION

This invention relates to novel compounds of the class bicycloheteroaryls that are capable of modulating P2X$_7$ receptor activity, and to pharmaceutical compositions containing such compounds. This invention also relates to methods for preventing and/or treating conditions that are causally related to aberrant P2X$_7$ activity, such as inflammation-related conditions in mammals, comprising (but not limited to) rheumatoid arthritis, osteoarthritis, Parkinson's disease, uveitis, asthma, cardiovascular conditions including myocardial infarction, the treatment and prophylaxis of pain syndromes (acute and chronic or neuropathic), traumatic brain injury, acute spinal cord injury, neurodegenerative disorders, inflammatory bowel disease and autoimmune disorders, using the compounds and pharmaceutical compositions of the invention.

BACKGROUND OF THE INVENTION

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members (P2X$_1$-P2X$_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three primary ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, which has been interpreted to indicate that ATP$^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor (rP2X$_7$) thus corresponds to the P2Z receptor. rP2X$_7$ is structurally related to other members of the P2X family but it has a longer cytoplasmic C-terminus domain (there is 35-40% amino acid identity in the corresponding region of homology, but the C-terminus is 239 amino acids long in the rP2X$_7$ receptor compared with 27-20 amino acids in the others). The rP2X$_7$ receptor functions both as a channel permeable to small cations and as a cytolytic pore. Brief applications of ATP (1-2s) transiently open the channel, as is the case of other P2X receptors. Repeated or prolonged applications of agonist cause cell permeabilization reducing the extracellular magnesium concentration potentiates this effect. The unique C-terminal domain of rP2X$_7$ is required for cell permeabilization and the lytic actions of ATP (Suprenant et al, Science 272:735 (1996)).

The P2Z/rP2X$_7$ receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). Certain functional differences exist between rodent and man (Hickman et al, Blood 84:2452 (1994)). The human macrophage P2X$_7$ receptor (P2X$_7$) has now been cloned and its functional properties determined (Rassendren et al, J. Biol. Chem. 272:5482 (1997). When compared with the rat P2X$_7$ receptor, elicited cation-selective currents in the human P2X$_7$ receptor required higher concentrations of agonists, were more potentiated by removal of extracellular magnesium ions, and revised more rapidly on agonist removal. Expression of chimeric molecules indicated that some of the differences between rat and human P2X$_7$ receptors could be revised by exchanging the respective C-terminal domains of the receptor proteins.

It has been reported that certain compounds act as P2X$_7$ antagonists. For example, WO99/29660 and WO99/29661 disclose that certain adamantane derivatives exhibit P2X$_7$ antagonistic activity having therapeutic efficacy in the treatment of rheumatoid arthritis and psoriasis. Similarly, WO99/29686 discloses that certain heterocyclic derivatives are P2X$_7$ receptor antagonists and are useful as immunosuppressive agents and treating rheumatoid arthritis, asthma, septic shock and atheroscelerosis. Finally, WO00/71529 discloses certain substituted phenyl compounds exhibiting immunosuppressing activity. All of the references described herein are incorporated herein by reference in their entirety.

A need therefore exists for therapeutic agents, and corresponding pharmaceutical compositions and related methods of treatment, that address the conditions causally related to aberrant P2X$_7$ activity, and it is toward the fulfillment and satisfaction of that need, that the present invention is directed.

SUMMARY OF THE INVENTION

Bicycloaryl derivatives of formulas I-VIa, and their pharmaceutical compositions are disclosed as therapeutic agents useful for the treatment of conditions in mammals associated with abnormal or aberrant activity of the P2X$_7$ receptor, including inflammatory-mediated conditions such as (but not limited to) arthritis, myocardial infarction, the treatment and prophylaxis of pain syndromes (acute and chronic [neuropathic]), traumatic brain injury, acute spinal cord injury, neurodegenerative disorders, inflammatory bowel disease and immune dysfunctions such as autoimmune disorders.

It has now been found that the present bicycloheteroaryl compounds are capable of mediating the activity of the P2X$_7$ receptor. This finding leads to novel compounds having therapeutic value. It also leads to pharmaceutical compositions having the compounds of the present invention as active ingredients and to their use to treat, prevent or ameliorate a range of conditions in mammals such as but not limited to inflammation of various genesis or etiology, for example rheumatoid arthritis, cardiovascular disease, inflammatory bowel disease, acute, chronic, inflammatory and neuropathic pain, dental pain and headache (such as migraine, cluster headache and tension headache) and other conditions causally related to inflammation or immune dysfunction.

The compounds of the present invention are also useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, uveitis, asthma, myocardial infarction, traumatic brain injury, spinal cord injury, neurodegenerative disorders, inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides bicycloheteroaryl compounds which are capable of modulating the activity of the $P2X_7$ receptor, in vivo. In a further aspect, the compounds of the invention are capable of antagonizing (suppressing or inhibiting) the activity of the $P2X_7$ receptor, and thereby treating those conditions, representative ones of which are causally related to aberrant $P2X_7$ activity.

Accordingly, in a first aspect of the invention, bicycloheteroaryl compounds are disclosed that are capable of modulating the activity of the $P2X_7$ receptor in vivo, having a formula (I):

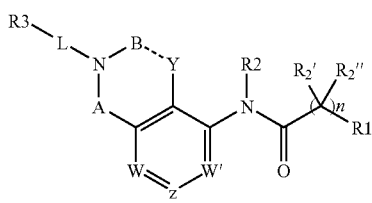

wherein
A is selected from $CR^2R^{2''}$, CO, and CS;
B is selected from $CR^{2'}$, $CR^{2'}R^{2''}$, CO, and CS;
Y is independently selected from $CR^{2'}$ and $CR^{2'}R^{2''}$;
W, W' and Z are independently selected from $CR^4$ and N, provided that all three of W, W' and Z can not be N at the same time;
L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl group, which can be optionally substituted by a substituent selected from hydroxyl, halogen and $C_1$-$C_6$ alkoxy;
n is 1, 2 or 3;
$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido; each of $R^2$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;
$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;
$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
and the dotted bond is a single or a double bond;
or a pharmaceutically acceptable salt, solvate or prodrug thereof;
and stereoisomers and tautomers thereof.

In a second aspect of the invention, bicycloheteroaryl compounds are disclosed that are capable of modulating the activity of the $P2X_7$ receptor in vivo, having a formula (Ia):

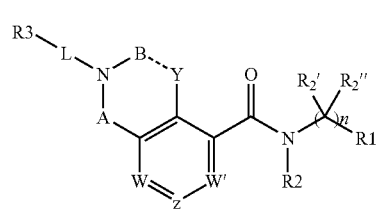

wherein

A is selected from $CR^{2'}R^{2'''}$, CO, and CS;

B is selected from $CR^{2'}$, $CR^{2'}R^{2'''}$, CO, and CS;

Y is independently selected from $CR^{2'''}$ and $CR^{2'}R^{2'''}$;

W, W' and Z are independently selected from $CR^4$ and N, provided that all three of W, W' and Z can not be N at the same time;

L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl which can be optionally substituted by a substituent selected from hydroxyl, halogen and $C_1$-$C_6$ alkoxy;

n is 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;

each of $R^2$, $R^{2'}$ and $R^{2'''}$ is independently selected from hydrogen, substituted or unsubstituted $C_1$-$C_6$ alkyl; or any of $R^{2'}$ and $R^{2'''}$ can join together to form a cycloalkyl or cycloheteroalkyl ring of 3-7 atoms;

$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;

or a pharmaceutically acceptable salt, solvate or prodrug thereof;

and stereoisomers and tautomers thereof.

In a further embodiment, with respect to compounds of formula I and Ia, n is 0.

In a further embodiment, with respect to compounds of formula I and Ia, L may be a bond and $R^3$ is selected from H, acyl, substituted acyl, substituted or unsubstituted aminocarbonyl, alkoxycarbonyl, substituted alkoxycarbonyl, substituted or unsubstituted sulfoxide, substituted or unsubstituted sulfone, substituted or unsubstituted aminosulfonyl, substituted or unsubstituted arylsulfonyl, aryloxycarbonyl, substituted aryloxycarbonyl, heteroaryloxycarbonyl, and substituted heteroaryloxycarbonyl.

In a further embodiment, with respect to compounds of formula I and Ia, L is $L^1$; and wherein $L^1$ is a bond, —CO—, —SO$_2$— or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy. In one particular embodiment, when A is CO or CS, $L^1$ is a bond or $C_1$-$C_5$ alkylene group.

In a further embodiment, with respect to compounds of formula I and Ia, L is $L^1$; and wherein $L^1$ is a bond, —CO—, —SO$_2$— or a $C_1$-$C_5$ alkylene group; and $R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl. In one particular embodiment, when $R^3$ is hydrogen $L^1$ is a bond or a $C_1$-$C_5$ alkylene group.

In a further embodiment, with respect to compounds of formula I and Ia, A, B and Y may all represent $CR^{2a}R^{2b}$. In another embodiment, A is $CR^{2a}R^{2b}$; and B and Y are independently selected from $CR^{2a}$ and $CR^{2a}R^{2b}$.

In a further embodiment, with respect to compounds of formula I and Ia, A, B and Y may all represent $CH_2$ and $R^2$ represents hydrogen.

In a further aspect, the present invention provides pharmaceutical compositions comprising a bicycloheteroaryl compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. inflammation, such as rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction, including autoimmune disorders, which method comprises administering an effective amount of one or more of the pharmaceutical compositions just described.

In yet another method of treatment aspect, this invention provides a method of treating a mammal susceptible to or afflicted with a condition that is causally related to aberrant P2X$_7$ receptor activity, and that for example, gives rise to pain responses or that relates to imbalances in the maintenance of basal activity of sensory nerves. The amnine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with conditions that are causally related to abnormal activity of the $P2X_7$ receptor, such as neurodegenerative diseases and disorders including, for example, Parkinson's disease, multiple sclerosis; diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and cardiovascular and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of the $P2X_7$ receptor and thus avert or treat any maladies that may be causally related thereto.

It is further an object of this invention to provide a series of compounds that can treat or alleviate maladies or symptoms of same, such as pain and inflammation, that may be causally related to the activation of the $P2X_7$ receptor.

A still further object of this invention is to provide pharmaceutical compositions that are effective in the treatment or prevention of a variety of disease states, including the diseases associated with the central nervous system, cardiovascular conditions, chronic pulmonary obstructive disease COPD), inflammatory bowel disease, rheumatoid arthritis, osteoarthritis, and other diseases where an inflammatory component is present.

Other objects and advantages will become apparent to those skilled in the art from a consideration of the ensuing detailed description.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that, consistent with the scope of the present invention, any of the moieties defined herein and/or set forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, $C_2$-$C_6$ alkenyl, $C_3$-$C_6$ alkynyl, $C_1$-$C_6$ alkoxy, aryl and di-$C_1$-$C_6$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamnino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S (O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'—, wherein R' is selected from hydrogen and alkyl.

"Arylamino" refers to the group aryl-NR'—, wherein R' is selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Amninocarbonyl" or "amido" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrinudine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylarnino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$—and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —$NO_2$.

"Substituted" refers to a group in which one or more hydrogen atoms are each independently replaced with the same or different substituent(s). Typical substituents include, but are not limited to, —X, —$R^{14}$, —$O^-$, =O, —$OR^{14}$, —$SR^{14}$, —$S^-$, =S, —$NR^{14}R^{15}$, =$NR^{14}$, —$CX_3$, —$CF_3$, —CH, —OCN, —SCN, —NO, —$NO_2$, =$N_2$, —$N_3$, —$S(O)_2O^-$, —$S(O)_2OH$, —$S(O)_2R^{14}$, —$OS(O_2)O^-$, —OS$(O)_2R^{14}$, —P(O)($O^-)_2$, —P(O)($OR^{14}$)($O^-$), —OP(O)($OR^{14}$)($OR^5$), —C(O)$R^{14}$, —C(S)$R^{14}$, —C(O)$OR^{14}$, —C(O)$NR^{14}R^{15}$, —C(O)$O^-$, —C(S)$OR^{14}$, —$NR^{16}$C(O)$NR^{14}R^{15}$, —$NR^{16}$C(S)$NR^{14}R^{15}$, —$NR^{17}$C($NR^{16}$)$NR^{14}R^{15}$ and —C($NR^{16}$)$NR^{14}R^{15}$, where each X is independently a halogen; each $R^{14}$, $R^{15}$, $R^{16}$ and $R^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —C(O)$R^{18}$ or —S(O)$_2R^{18}$ or optionally $R^{18}$ and $R^{19}$ together with the atom to which they are both attached form a cycloheteroalkyl or substituted cycloheteroalkyl ring; and $R^{18}$ and $R^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

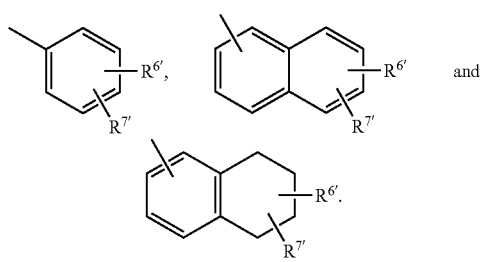

In these formulae one of $R^{6'}$ and $R^{7'}$ may be hydrogen and at least one of $R^{6'}$ and $R^{7'}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{10}COR^{11}$, $NR^{10}SOR^{11}$, $NR^{10}SO_2R^{14}$, COOalkyl, COOaryl, $CONR^{10}R^{11}$, $CONR^{10}OR^{11}$, $NR^{10}R^{11}$, $SO_2NR^{10}R^{11}$, S-alkyl, S-alkyl, SOalkyl, $SO_2$alkyl, Saryl, SOaryl, $SO_2$aryl; or $R^{6'}$ and $R^{7'}$ may be joined to form a cyclic ring (saturated or unsaturated) from 5 to 8 atoms, optionally containing one or more heteroatoms selected from the group N, O or S. $R^{10}$, $R^{11}$, and $R^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

Examples of representative heteroaryls include the following:

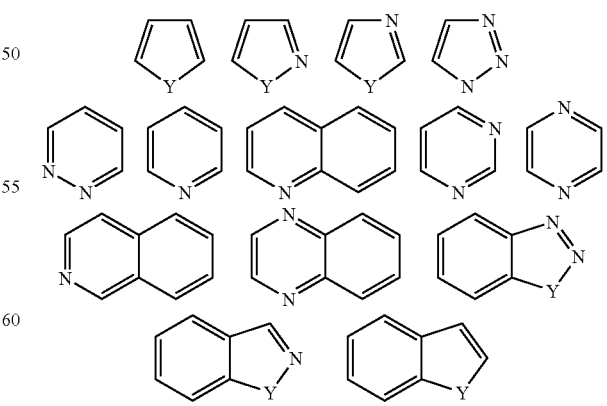

wherein each Y is selected from carbonyl, N, $NR^4$, O, and S, where $R^4$ is as defined herein.

Examples of representative cycloheteroalkyls include the following

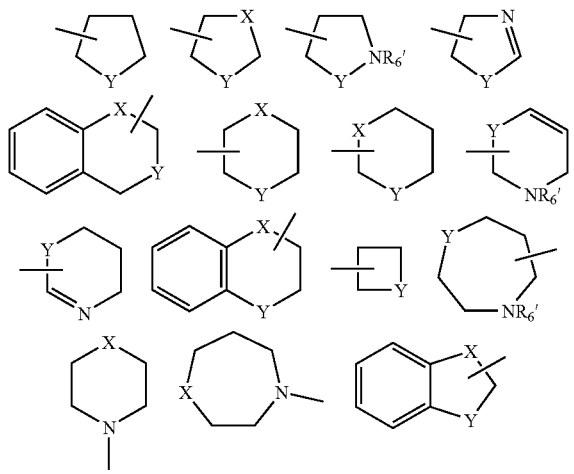

wherein each X is selected from CR$^4_2$, NR$^4$, O and S; and each Y is selected from NR$^4$, O and S, and where R$^{6'}$ is R$^2$, R$^2$ and R$^4$ being as defined herein.

Examples of representative cycloheteroalkenyls include the following:

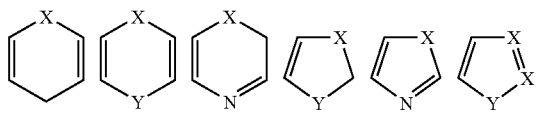

wherein each X is selected from CR$^4$, NR$^4$, O and S; and each Y is selected from carbonyl, N, NR$^4$, O and S, where R$^4$ is as defined herein.

Examples of representative aryl having hetero atoms containing substitution include the following:

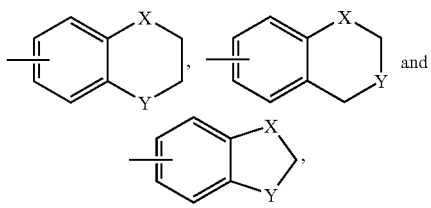

wherein each X is selected from C—R$^4$, CR$^4_2$, NR$^4$, O and S; and each Y is selected from carbonyl, NR$^4$, O and S, where R$^4$ is as defined herein.

"Hetero substituent" refers to a halo, O, S or N atom-containing functionality that may be present as an R$^4$ in a CR$^4$ group present as substituents directly on W or Z of the compounds of this invention or may be present as a substituent in the "substituted" aryl, heteroaryl and aliphatic groups present in the compounds.

Examples of hetero substituents include:
-halo,
—NO$_2$, —NH$_2$, —NHR, —N(R)$_2$,
—NRCOR, —NRSOR, —NRSO$_2$R, OH, CN, CO$_2$R,
—CO$_2$H,
—O—R,
—CON(R)$_2$, —CONROR,
—SO$_3$H, —S—R, —SO$_2$N(R)$_2$,
—S(O)R, and —S(O)$_2$R, wherein each R is independently an aryl or aliphatic, optionally with substitution. Among hetero substituents containing R groups, preference is given to those materials having aryl and alkyl R groups as defined herein. Where feasible, each R may include hydrogen. Also, where feasible, two R groups when on same atom may join to form a heterocyclic ring of 3-8 atoms. For example, two R groups of NR$^2$, SO$_2$NR$^2$, and CONR$^2$ may join, together with the N atom, to form a N-morpholino, N-pyrrolo, N-piperidino, and N-pyrazolylo ring. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring.

Examples of heterocyclic rings include, but are not limited to, piperazinyl, homopiperazinyl, piperidinyl and morpholinyl, and are shown in the following illustrative examples:

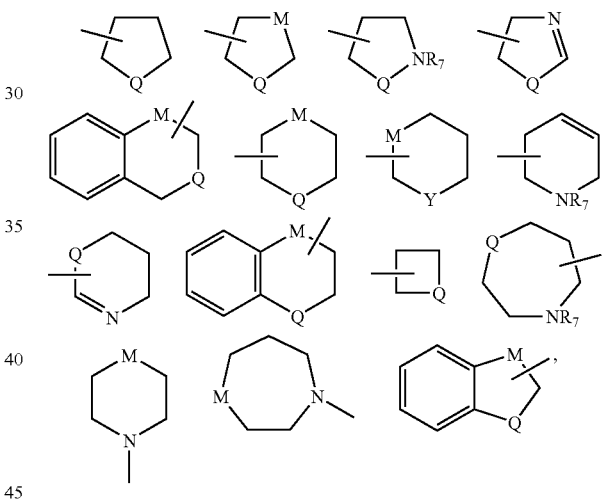

optionally substituted with one or more groups selected from the group consisting of acyl, acylamnino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is CR$^7$, NR$^2$, O or S; Q is O, NR$^2$ or S, where R$^2$ is as defined herein. R$^7$ and R$^8$ are independently selected from the group consisting of acyl, acylamino, acyloxy, alkoxy, substituted alkoxy, alkoxycarbonyl, alkoxycarbonylanino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as S(O$_2$)—R wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfoxide" refers to the divalent radical —S(O)—. "Substituted sulfoxide" refers to a radical such as S(O)—R, wherein R is any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention,which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol-keto structures and equilibrium are illustrated below:

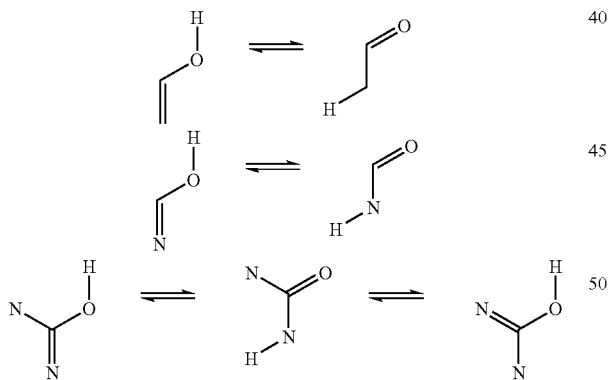

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides bicycloheteroaryl compounds useful for preventing and/or treating a broad range of conditions, associated with abnormalities in the activity of the $P2X_7$ receptor, among them, rheumatoid arthritis, Parkinson's disease, uveitis, asthma, cardiovascular conditions such as myocardial infarction, the treatment and prophylaxis of pain syndromes (acute and chronic or neuropathic), traumatic brain injury, acute spinal cord injury, neurodegenerative disorders, inflammatory bowel disease and immune dysfunctions such as autoimmune disorders or conditions, in mammals.

In a first aspect of the invention, bicycloheteroaryl compounds are disclosed that are capable of modulating the activity of the $P2X_7$ receptor in vivo, having a formula (I):

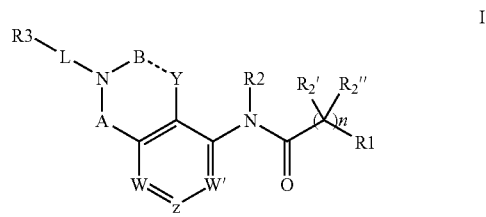

wherein
A is selected from $CR^{2'}R^{2''}$, CO, and CS;
B is selected from $CR^{2'}$, $CR^{2'}R^{2''}$, CO, and CS;
Y is independently selected from $CR^{2'}$ and $CR^{2'}R^{2'}$;
W, W' and Z are independently selected from $CR^4$ and N, provided that all three of W, W' and Z can not be N at the same time;
L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl group, which can be optionally substituted by a substituent selected from hydroxyl, halogen and $C_1$-$C_6$ alkoxy;
n is 1, 2 or 3;
$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido; each of $R^2$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;
$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and the dotted bond is a single or a double bond;

or a pharmaceutically acceptable salt, solvate or prodrug thereof;

and stereoisomers and tautomers thereof.

In another aspect the present invention provides bicycloheteroaryl compounds bicycloheteroaryl compounds are disclosed that are capable of modulating the activity of the $P2X_7$ receptor in vivo, having a formula (Ia):

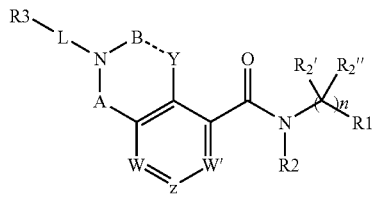

Ia wherein

A is selected from $CR^2R^{2''}$, CO, and CS;

B is selected from $CR^{2'}$, $CR^2R^{2''}$, CO, and CS;

Y is independently selected from $CR^{2'}$ and $CR^2R^{2''}$;

W, W' and Z are independently selected from $CR^4$ and N, provided that all three of W, W' and Z can not be N at the same time;

L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl group, which can be optionally substituted by a substituent selected from hydroxyl, halogen and $C_1$-$C_6$ alkoxy;

n is 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido; each of $R^2$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;

$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and the dotted bond is a single or a double bond;

or a pharmaceutically acceptable salt, solvate or prodrug thereof;

and stereoisomers and tautomers thereof.

In a further embodiment as to compounds of formula I and Ia, n may be 0.

In a further embodiment, with respect to compounds of formula I and Ia, L may be a bond and $R^3$ is selected from H, acyl, substituted acyl, substituted or unsubstituted aminocarbonyl, alkoxycarbonyl, substituted alkoxycarbonyl, substituted or unsubstituted sulfoxide, substituted or unsubstituted sulfone, substituted or unsubstituted aminosulfonyl, substituted or unsubstituted arylsulfonyl, aryloxycarbonyl, substituted aryloxycarbonyl, heteroaryloxycarbonyl, and substituted heteroaryloxycarbonyl.

In a further embodiment, with respect to compounds of formula I and Ia, L is $L^1$; and wherein $L^1$ is a bond, —CO—, —SO$_2$— or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy. In one particular embodiment, when A is CO or CS, $L^1$ is a bond or $C_1$-$C_5$ alkylene group.

In a further embodiment, with respect to compound of formula I and Ia, L is $L^1$; and wherein $L^1$ is a bond, —CO—, —SO$_2$— or a $C_1$-$C_5$ alkylene group; and $R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl. In one particular embodiment, when $R^3$ is hydrogen, $L^1$ is a bond or a $C_1$-$C_5$ alkylene group.

In a further embodiment, with respect to compound of formula I and Ia, A, B and Y may all represent $CR^{2a}R^{2b}$. In another embodiment, A is $CR^{2a}R^{2b}$; and B and Y are independently selected from $CR^{2a}$ and $CR^{2a}R^{2b}$.

In another aspect the present invention provides bicycloheteroaryl compounds bicycloheteroaryl compounds are disclosed that are capable of modulating the activity of the P2X$_7$ receptor in vivo, having a formula (II or Ia):

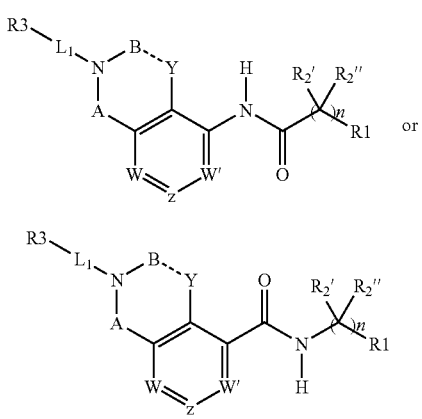

wherein

A is selected from $CR^{2a}R^{2b}$;

B and Y are independently selected from $CR^{2a}$ and $CR^{2a}R^{2b}$;

W, W' and Z are independently selected from $CR^4$ and N, provided that all three of W, W' and Z can not be N at the same time;

$L^1$ is a bond, —CO—, —SO$_2$— or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy;

n is 0, 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;

each of $R^2$, $R^{2a}$, $R^{2b}$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;

$R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and the dotted bond is a single or a double bond;

or a pharmaceutically acceptable salt, solvate or prodrug thereof;

and stereoisomers and tautomers thereof.

In one particular embodiment, with respect to compounds of formula II and IIa, when $R^3$ is hydrogen, $L^1$ is a bond or a $C_1$-$C_5$ alkylene group.

In a further embodiment, with respect to compounds of formula II and IIa, A, B and Y may all represent $CR^{2a}R^{2b}$ and the dotted bond is a single bond.

In a further embodiment, with respect to compounds of formula II and IIa, A is $CR^{2a}R^{2b}$; and B and Y each represent $CR^{2a}$ and the dotted bond is a double bond.

In a further embodiment, with respect to compounds of formula II and IIa, A, B and Y may all represent CH$_2$ and the dotted bond is a single bond.

In a further embodiment, with respect to compounds of formula II and IIa, A is CH$_2$; and B and Y each represent CH and the dotted bond is a double bond.

In one embodiment, with respect to compounds of formula II and IIa, W' is N.

In another embodiment, with respect to compounds of formula II and IIa, W' is $CR^4$.

In another embodiment, with respect to compounds of formula II and IIa, W' is $CR^4$ and $R^{4'}$ is selected from hydrogen, halo, alkoxy, alkyl, and dialkylamino.

In another embodiment, with respect to compounds of formula II and IIa each of $R^{2'}$ and $R^{2''}$ of the

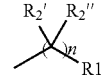

group is H.

In another embodiment, with respect to compound of formula II and IIa, wherein one of $R^{2'}$ and $R^{2''}$ of the

group is Me and the other is H.

In another embodiment, with respect to compounds of formula II and IIa, each of $R^{2'}$ and $R^{2''}$ of the

group is Me.

In another embodiment, with respect to compounds of formula II and IIa, n is 0 or 1. In one particular embodiment, n is 0. In yet another particular embodiment, n is 1.

In another embodiment, with respect to compounds of formula II and IIa, wherein the

group is selected from substituted or unsubstituted

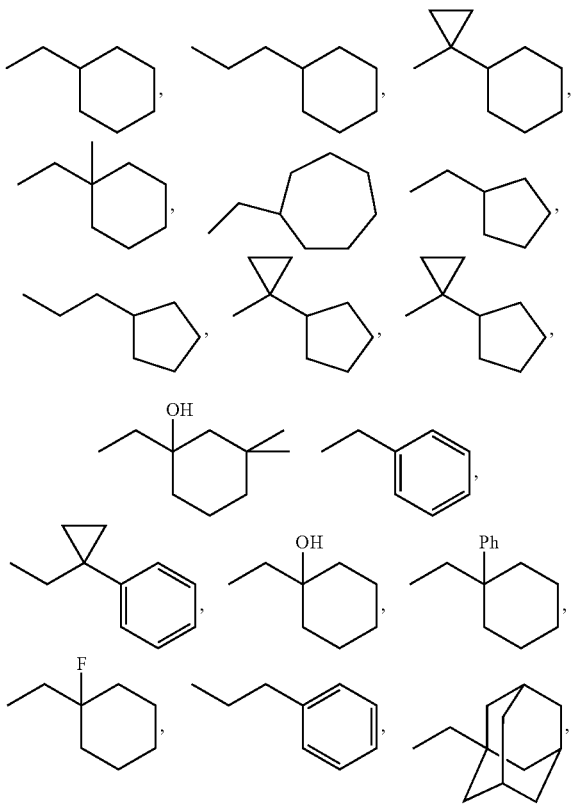

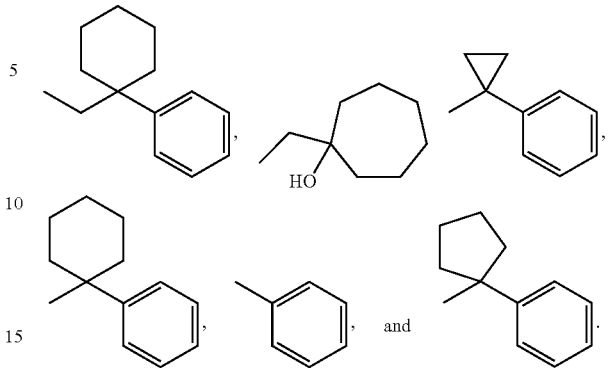

In another embodiment, with respect to compound of formula II and IIa, wherein the

group is

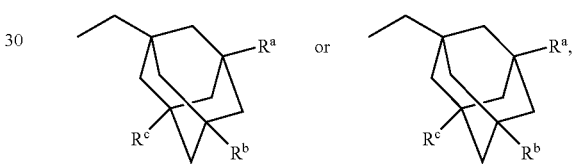

and wherein $R^a$, $R^b$ and $R^c$ are independently selected from H, halo, hydroxyl, substituted hydroxyl, alkyl, substituted alkyl, amino, substituted amino, aryl and substituted aryl.

In another embodiment, with respect to compounds of formula II and IIa, the

group is as described in the preceding paragraph, and $R^a$, $R^b$ and $R^c$ are independently selected from H, Br, Cl, OH, Me, NHAc, Ph and F. In one particular embodiment, each of $R^a$, $R^b$ and $R^c$ is H.

In another aspect the present invention provides bicycloheteroaryl compounds and bicycloheteroaryl compounds are disclosed that are capable of modulating the activity of the P2X$_7$ receptor in vivo, and that have a formula (III, IIIa, IV or IVa):

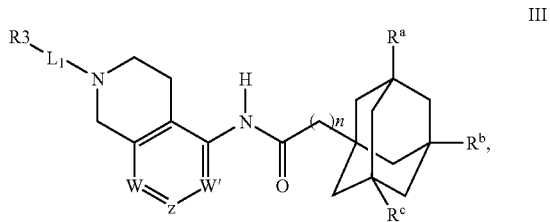

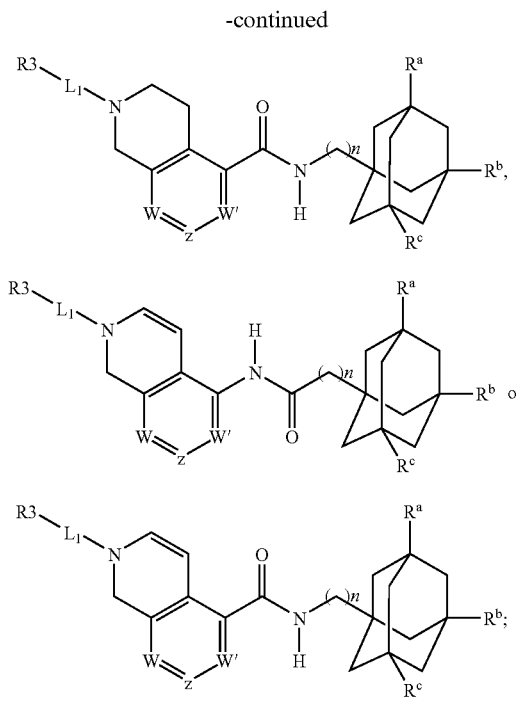

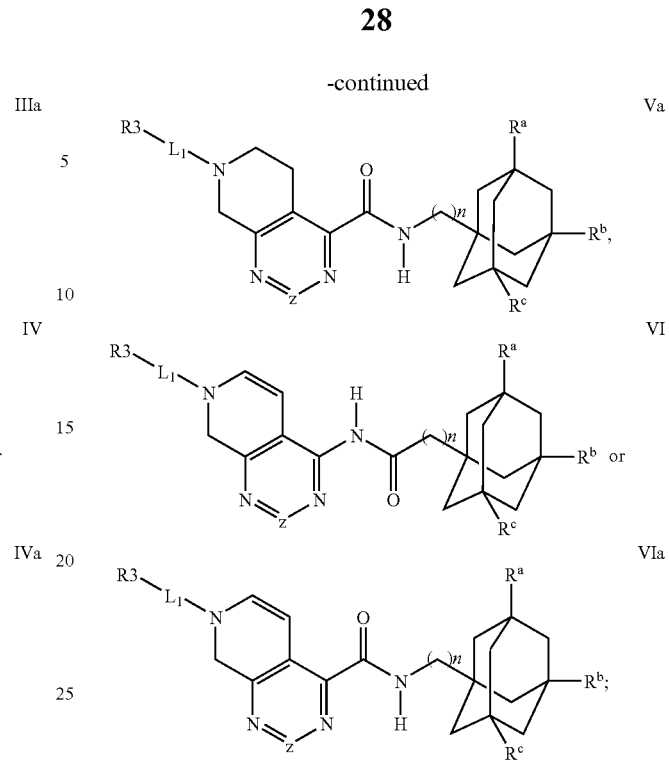

wherein $L^1$, $R^3$, W, Z, W' and n are as described for formula II or IIa; and wherein $R^a$, $R^b$ and $R^c$ are independently selected from H, halo, hydroxyl, substituted hydroxyl, alkyl, substituted alkyl, amino, substituted amino, aryl and substituted aryl.

In one embodiment, with respect to compounds of formulae II-IVa, each of W, W' and Z is independently $CR^4$.

In one embodiment, with respect to compounds of formulae II-IVa, each of W, W' and Z is independently CH.

In one embodiment, with respect to compounds of formulae II-IVa, W' is C-Me and W and Z both are CHs.

In one embodiment, with respect to compounds of formulae II-IVa, W' is N and W and Z both are $CR^4$s.

In one embodiment, with respect to compounds of formulae II-IVa, W' is N and W and Z both are CHs.

In one embodiment, with respect to compounds of formulae II-IVa, Z is $CR^4$ and W and W' both are Ns.

In one embodiment, with respect to compounds of formulae II-IVa, Z is CH and W and W' both are Ns.

In one embodiment, with respect to compounds of formulae II-IVa, Z is N and W and W' both are $CR^4$s.

In another aspect the present invention provides bicycloheteroaryl compounds and bicycloheteroaryl compounds are disclosed, that are capable of modulating the activity of the P2X$_7$ receptor in vivo, having a formula (V, Va, VI or VIa):

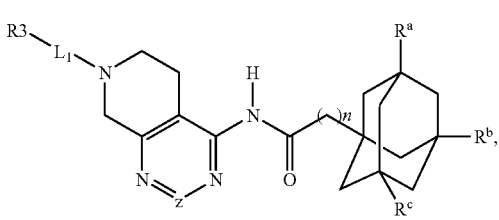

and wherein $L^1$, $R^3$, Z, and n are as described for formula II or IIa; and wherein $R^a$, $R^b$ and $R^c$ are independently selected from H, halo, hydroxyl, substituted hydroxyl, alkyl, substituted alkyl, amino, substituted amino, aryl and substituted aryl.

In one embodiment, with respect to compounds of formulae II-VIa, n is 0.

In another embodiment, with respect to compounds of formulae II-VIa, n is 1.

In one embodiment, with respect to compounds of formulae II-VIa, each of $R^a$, $R^b$ and $R^c$ is H.

In one embodiment, with respect to compounds of formulae II-VIa, each of $R^a$, $R^b$ and $R^c$ is Me.

In another embodiment, with respect to compounds of formulae II-VIa, two of $R^a$, $R^b$ and $R^c$ is Me.

In another embodiment, with respect to compounds of formulae II-VIa, one of $R^a$, $R^b$ and $R^c$ is OH.

In another embodiment, with respect to compounds of formulae II-VIa, Z is $CR^4$ and $R^4$ is selected from hydrogen, halo, alkoxy, alkyl, and dialkylamino.

In one embodiment, with respect to compounds of formulae II-VIa, $L^1$ is a bond and $R^3$ is H.

In another embodiment, with respect to compounds of formulae II-VIa, $L^1$ is a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy; and $R^3$ is H.

In another embodiment, with respect to compounds of formulae II-VIa, $L^1$ is —CO—, or —SO$_2$—.

In another embodiment, with respect to compounds of formulae II-VIa, $L^1$ is $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_{1-6}$ alkoxy.

Further in accordance with compounds of formulae II-VIa, $L^1$ may be a substituted or unsubstituted $C_1$-$C_6$ alkylene group, and particularly, may be $CH_2$, —$(CH_2)_2$—, —$(CH_2)_3$—, or —$(CH_2)_4$—.

In one embodiment, with respect to compounds of formulae II-VIa, $R^3$ is substituted or unsubstituted alkyl.

In one particular embodiment, with respect to compounds of formulae II-VIa, $R^3$ is substituted alkyl; and the substitution on alkyl is selected from aryl, heteroaryl, cycloalkyl, heteroalkyl, halo, alkoxy, hydroxy, cyano, and aryloxy. In another particular embodiment, the substitution on alkyl is selected from Ph, Cl, F, Br, CN, OH, OMe, OPh, $CF_3$, $CHF_2$, $OCF_3$, t-Bu, SMe, SOMe, $SO_2Me$, $SO_3H$, $SO_3Me$, pyridyl, cyclopropyl, cyclopentyl and cyclohexyl.

Still further in accordance with the invention, and with respect to the compounds of formalae II-VIa, where present, -$L^1$-$R^3$ may be selected from H, Me, Et, benzyl, —$(CH_2)_3$—OH, —$(CH_2)_4$—NHMe, —$(CH_2)_4$—OH, —$(CH_2)_2$—CH(OH)—$CH_2OH$, —$(CH_2)_4$—$CO_2H$, —$(CH_2)_4$—NHEt, —$(CH_2)_3$—NHEt, —$(CH_2)_2$—NH—$(CH_2)_2OH$, —$(CH_2)_3$—NH—$(CH_2)_3OH$, —$(CH_2)_4$—$NH_2$, —$(CH_2)_3$—$NHCONHSO_2Me$, —$(CH_2)_3$—NH—$(CH_2)_2$-Me, or —$(CH_2)_2CO_2H$.

In one embodiment, with respect to compounds of formulae II-VIa, $L^1$ is a —CO—, —$SO_2$— or a $C_1$-$C_5$ alkylene group and $R^3$ is substituted or unsubstituted aryl.

In one particular embodiment, with respect to compounds of formulae II-VIa, $L^1$ is a —CO—, —$SO_2$— or a $C_1$-$C_5$ alkylene group and $R^3$ is

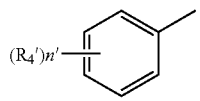

and wherein n' is selected from 1-5 and each of $R^{4'}$ is independently selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

In one particular embodiment, n' is 1, 2 or 3. In another particular embodiment, n' is 1, or 2. In yet another particular embodiment, n' is 1.

In one particular embodiment, each $R^{4'}$ is independently selected from Me, Et, Ph, Cl, F, Br, CN, OH, OMe, OPh, COPh, $CF_3$, $CHF_2$, $OCF_3$, t-Bu, SMe, CH=CH—$CO_2H$, SOMe, $SO_2Me$, $SO_3H$, $SO_3Me$, and pyridyl.

In one particular embodiment, with respect to compound of formulae II-VIa, $L^1$ is a —CO—, —$SO_2$— or a $C_1$-$C_5$ alkylene group and $R^3$ is substituted or unsubstituted cycloalkyl, heterocycloalkyl, heteroaryl, bicycloaryl or bicycloheteroaryl. In another particular embodiment, the substitution is selected from Me, Et, Ph, Cl, F, Br, CN, OH, OMe, OPh, COPh, $CF_3$, $CHF_2$, $OCF_3$, t-Bu, SMe, CH=CH—$CO_2H$, SOMe, $SO_2Me$, $SO_3H$, and $SO_3Me$.

In one particular embodiment, with respect to compound of formulae II-VIa, $L^1$ is a —CO—, —$SO_2$— or a $C_1$-$C_5$ alkylene group and $R^3$ is substituted or unsubstituted naphthalene, furanyl, thiophenyl, pyrrolyl, pyrazolyl, imidazolyl, triazolyl, pyridyl, pyrimidinyl, quinoline, isoquinolinyl, tetrahydroquinolinyl, tetrahydroisoquinolinyl, indolyl, benzopyranyl, benzofuranyl, benzoxazinyl, or benzodioxanyl. In another particular embodiment, the substitution is selected from Me, Et, Ph, Cl, F, Br, CN, OH, OMe, OPh, COPh, $CF_3$, $CHF_2$, $OCF_3$, t-Bu, SMe, CH=CH—$CO_2H$, SOMe, $SO_2Me$, $SO_3H$, and $SO_3Me$.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the $P2X_7$ receptor. Accordingly, the compounds and pharmaceutical compositions of this invention find use as therapeutics for preventing and/or treating autoimmune, inflammatory and cardiovascular conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, multiple sclerosis; diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present amine compounds for use as a pharmaceutical especially in the treatment or prevention of the aforementioned conditions and diseases. We also provide use of a present amine compound in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis,* Second Edition, Wiley, N.Y., 1991, and references cited therein.

The following schemes are presented with details as to the preparation of representative bicycloheteroaryls that have been listed hereinabove. The compounds of the invention may be prepared from known or commercially available starting materials and reagents by one skilled in the art of organic synthesis.

The intermediate heteroaryl amines, heteroaryl acids, acid chlorides (Intermediate 1-16) can be obtained using synthetic methods given below.

Intermediate 1

Preparation of 7-benzyl-5,6,7,8-tetrahydropyrido[3,4-d]pyrimidin-4-amine a) 7-Benzyl-5,6,7,8-tetrahydropyrido[3,4d]pyrimidin-4(3H)-one hydrochloride

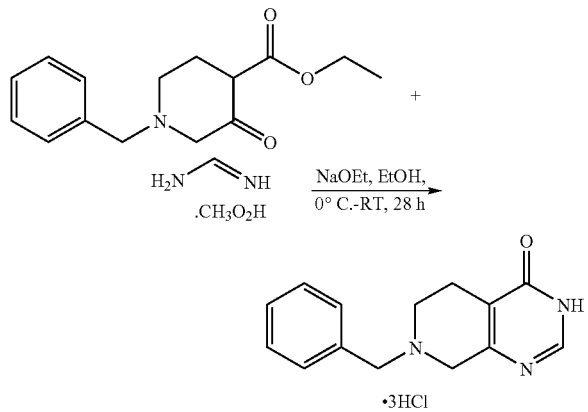

Ethyl 1-benzyl-3-oxopiperidine-4-carboxylate (30 g, 101 mmol) was combined with formamidine aceate (10.5 g, 101 mmol) and EtOH (450 mL) in a 2-liter flask. The resulting mixture was stirred at 0° C. and treated with NaOEt (21% in EtOH) (112.6 mL, 299 mmol). The reaction was heated at 60° C. overnight and monitored for completion via 1 cms and TLC (DCM:MeOH:: 95:5). Additional ethyl 1-benzyl-3-oxopiperidine-4-carboxylate (2 g, 6.6 mmol) was added after 12 h with continued heating at 60° C. The reaction was complete after 4 h as indicated by LCMS. The cooled reaction was reduced in vacuo and the residue was treated concentrated HCl (300 mL) and stirred overnight at room temperature. The solvents were removed under vacuum and the resulting solids treated with EtOH (300 mL), stirred for 15 minutes, and then filtered. The mother liquor was discarded and the precipitate dried in a vacuum oven affording 7-benzyl-5,6,7,8-tetrahydropyrido[3,4-d]pyrimidin-4-ol (44 g) as the tri-HCl salt which was used directly in the next step.

LCMS (ESI⁺) m/z 242.2 [M+H]⁺

¹H NMR (300 MHz CD₃OD) δ 7.98 (s, 1H), 7.35-7.32 (m, 5H), 3.72 (s, 2H), 3.41-3.40 (m, 2H), 2.75 (t 2H), 2.57 (m, 2H).

b) 7-Benzyl-4-chloro-5,6,7,8-tetrahydropyrido[3,4-d]pyrimidine

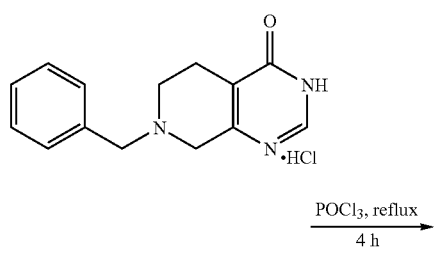

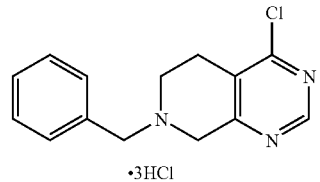

7-Benzyl-5,6,7,8-tetrahydropyrido[3,4-d]pyrimidin-4-ol-.HCl (35.5 g, 0.101 mol) was added in a 250 ml round bottom flask, equipped with a reflux condenser, followed by the addition of POCl₃ (100.5 g, 0.655 mol). The resulting mixture was refluxed for 4 h under argon, cooled to room temperature, and diluted with DCM (200 mL). The crude reaction was then poured into ice-cold water (200 mL) and stirred overnight at 0° C. The layers were separated and the pH of aqueous layer was carefully adjusted to 7 via the addition of satd. NaHCO₃. The aqueous layer was extracted with DCM (3×100 mL) and the combined organics washed with satd. NaHCO₃ (50 mL), dried over anhyd. Na₂SO₄, and reduced in vacuo to yield 7-benzyl-4-chloro-5,6,7,8-tetrahydropyrido[3,4-d]pyriridine as a viscous dark brown oil (21 g, 80%).

LCMS (ESI⁺) m/z 260.1 [M+H]⁺

¹H NMR (300 MHz CD₃OD) δ 8.68 (s, 1H), 7.36-7.29 (m, 5H), 3.75 (s, 2H), 3.65 (s, 2H), 3.65 (s, 2H), 2.86 (s, 4H).

c) 7-Benzyl-5,6,7,8-tetrahydropyrido[3,4-d]pyrimidin-4-amine

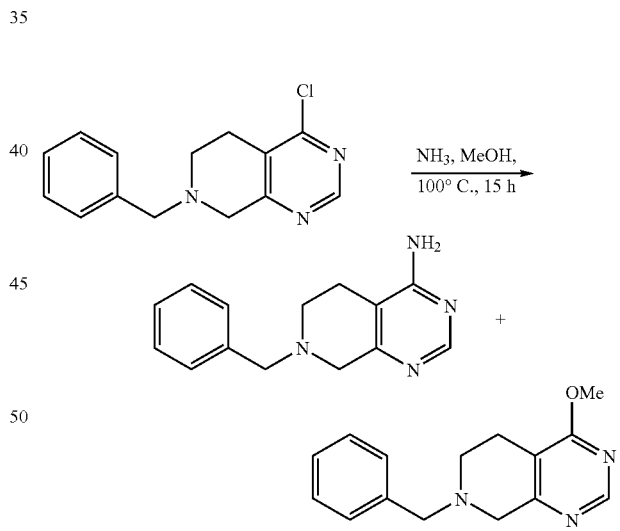

7-Benzyl-4-chloro-5,6,7,8-tetrahydropyrido[3,4-d]pyrimidine (9.83 g, 38 mmol) was dissolved in solution of NH₃ in MeOH (7N, 60 mL) in a re-sealable tube. The sealed tube was heated at 100° C. for 21 h. The reaction was cooled to room temperature and kept standing at room temperature for 48 h which led to the precipitation of the desired product 7-benzyl-5,6,7,8-tetrahydropyrido[3,4-d]pyrimidin-4-amine. (5.1 g, 56%). The mother liquor was evaporated and dried under vacuum to yield a mixture of 4.12 g of desired product together with the side product 7-benzyl-4-methoxy-5,6,7,8-tetrahydropyrido[3,4-d]pyrimidine.

LCMS (ESI+) m/z 241.3 [M+H]+

¹H-NMR (300 MHz, CDCl₃) δ 8.33 (s, 1H), 7.28 (m, 5H), 4.86 (br 's', 2H), 3.69 (s, 2H, 3.55 (s, 2H), 2.79 (t, 2H), 2.48 (t, 2H).

¹³C NMR (75 MHz, CDCl₃) δ 161.2, 161.1, 155.8, 137.6, 129.3, 128.6, 127.5, 110.2, 62.6, 57.6, 49.5, 23.2.

Intermediate 2

Preparation of 2-adamantan-1-yl-N-(5,6,7,8-tetrahydro-pyrido[3,4-d]pyrimidin-4-yl)-acetamide Method A Representative Synthesis of Compound 5 a) 2-Adamantan-1-yl-N-(7-benzyl-5,6,7,8-tetrahydro-pyrido[3,4-d]pyrimidin-4-yl)-acetamide

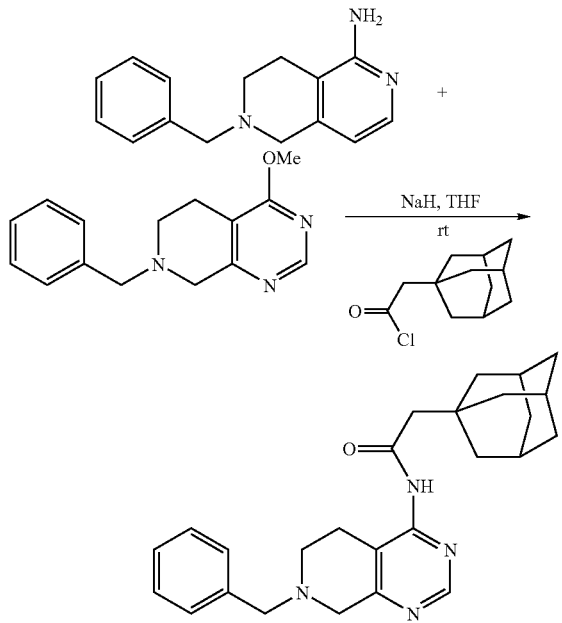

To a solution of 7-benzyl-4-methoxy-5,6,7,8-tetrahydropyrido[3,4-d]pyrimidine and 7-benzyl-5,6,7,8-tetrahydropyrido[3,4-d]pyrimidin-4-amine (1.2 g, 5 mmol (based on 5)) in THF (15 mL was added NaH (60% in mineral oil) (0.04 g, 1.67 mmol) and the resulting mixture was stirred for 1 h. 1-adamant-1-yl -acetyl chloride (1.11 g, 0.86 mmol) was then added to the reaction mixture and the reaction stirred at room temperature for 18 h. The reaction was monitored by LCMS and treated with an additional amount each of NaH (0.3 g) and 1-adamant-1-yl-acetyl chloride (0.3 g). Upon completion the reaction mixture was treated with saturated. NaHCO₃ (50 mL) and extracted with EtOAc (2×50 ml). The combined organics were dried over anhydrous Na2SO4, filtered and concentrated to yield 2-Adamantan-1-yl-N-(7-benzyl-5,6,7,8-tetrahydro-pyrido[3,4-d]pyrimidin-4-yl)-acetamide (2.06 g)

LCMS (ESI+) m/z 417.5 [M+H]+

1H-NMR (300 MHz, CDCl3) δ 8.68 (s, 1H), 7.50 (s, 1H), 7.30 (m, 5H), 3.70 (s, 4H), 2.74 (s, 4H), 2.30 (s, 2H), 1.98 (br 's', 3H), 1.65 (m, 12H).

b) Representative Synthesis of Compound 6

2-Adamantan-1-yl-N-(5,6,7,8-tetrahydro-pyrido[3,4-d]pyrimidin-4-yl)-acetamide

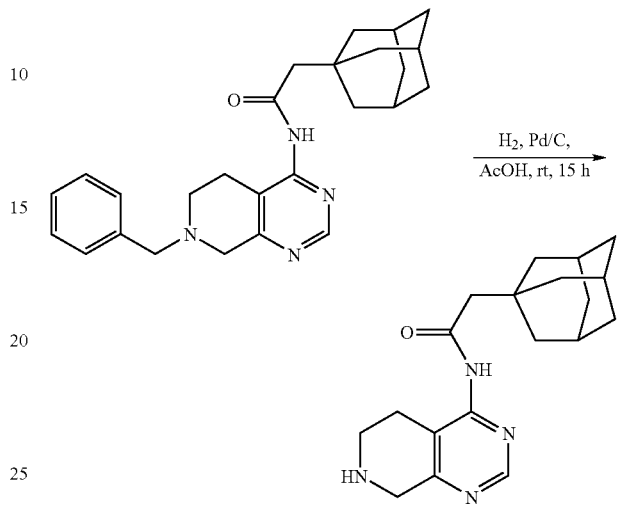

To a solution of 2-adamantan-1-yl-N-(7-benzyl-5,6,7,8-tetrahydro-pyrido[3,4-d]pyrimidin 4-yl)-acetamide in glacial acetic acid (15 mL) in a 250 ml round bottom flask was added 10% Pd/C (0.45 g). The resulting mixture was stirred for 15 h under an atmosphere of hydrogen (via a balloon), which was introduced after evacuation of air from the reaction vessel. The reaction was then filtered over celite, washed with EtOAc (20 mL) and the filtrate concentrated under reduced pressure. The residue was re-dissolved on EtOAc (50 mL) and stirred with aq. 10% NaOH solution (50 mL) for 1 h. The layers were separated and the aqueous layer washed with EtOAc (5×50 mL). The combined organics were dried over anhyd. Na₂SO₄, filtered and concentrated to yield 2-adamantan-1-yl-N-(5,6,7,8-tetrahydro-pyrido[3,4-d] pyrimidin-4-yl)-acetamide (0.68 g, 2.1 mmol, 87%) as a tan colored solid. LCMS (ESI+) m/z 327.3 [M+H]+

¹H-NMR (300 MHz, CDCl₃) δ 8.70 (s, 1H), 7.73 (s, 1H), 4.06 (s, 2H), 3.13 (t, J=5.7 Hz, 2H), 2.66 (t, 2H), 2.29 (s, 2H), 1.99 (br s, 3H), 1.71 (m, 12H).

Intermediate 3

Preparation of (3,5-Dimethyl-adamantan-1-yl)-acetyl chloride

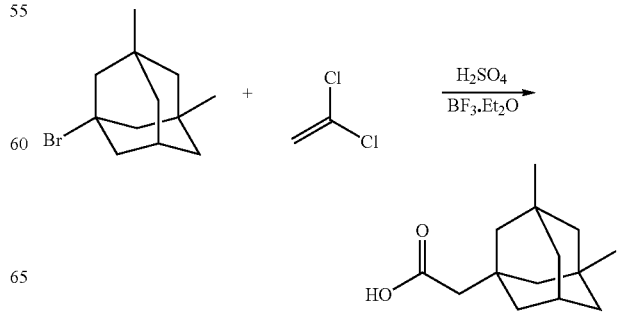

(3,5-Dimethyl-adamantan-1-yl)-acetic acid

The bromide (24.32 g, 100 mmol) in dichloroethane was added into 90% $H_2SO_4$ solution at 10° C. (cold water bath). The reaction mixture was stirred at 10° C. for 1 hr. Then $BF_3$ etherate (2.84 g, 20 mmol) was added dropwise in 30 minutes via a syringe. The reaction mixture was stirred at 10-15° C. for 2 more hours with additional $BF_3$ etherate was added until complete consumption of the starting bromide before pouring onto ice. The water was adjusted to pH=9 followed by extraction with ether. The aqueous layer was acidified with HCl to pH=3 followed by extraction with ether, dried, removal of organic solvent to give solid product, which was taken on directly to the next step.

$^1$H NMR (300 MHz, $CD_3Cl_3$), 2.13 (s, 2H), 1.74 (s, 1H), 1.02-1.38 (m, 12H), δ 0.82(s, 6H),

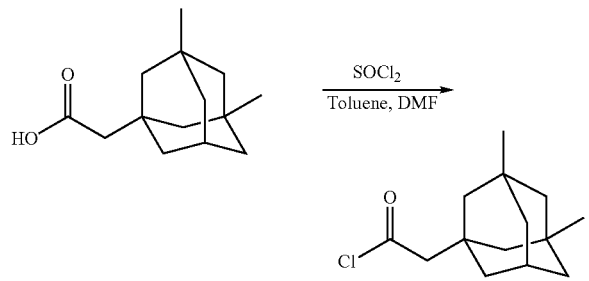

(3,5-Dimethyl-adamantan-1-yl)-acetyl chloride

Into a flask containing 3,5-dimethyl-adamantan-1-yl)-acetic acid in toluene (50 ml) was added $SOCl_2$ and 1 drop of DMF. Reaction was then heated to 60° C. for 1 hour. After removal of solvent and co-evaporation with toluene (2 ml), the crude product was used without further purification.

Intermediate 4

Preparation of (3,5,7-Trimethyl-adamantan-1-yl)-acetyl chloride

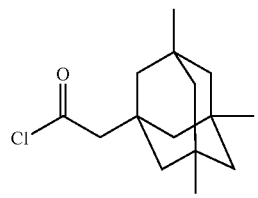

3,5,7-trimethyl adamantane-1-carboxylic acid was converted to it's acid chloride per the procedure described for 3,5-dimethyl-adamantan-1-yl)-acetic acid. It was then homologated to the corresponding benzyl ester via the procedure described in Tetrahedron Letters, 1980, 21, 4461-4462. The benzyl ester was converted to the acid by standard hydrogenation conditions of 10% Pd/C in MeOH/EtOAc:: 1:1. The acid was then converted to the acid chloride via standard treatment with thionyl chloride at reflux for 1 to 2 hours. Excess reagent was azeotropically removed with hexanes and the resulting acid chloride was used without further purification.

Intermediate 5

Preparation of 2-Adamantan-1-yl-2-methyl-propionyl chloride

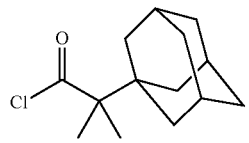

2-Adamantan-1-yl-2-methyl-propionic acid methyl ester

The methyl ester was prepared via the route described in Tetrahedron Letters, 1978, 17, 1455-1458. Thus 1-bromoadamantane (6.17 g, 28.7 mmol), (1-methoxy-2-methyl-prop-1-enyloxy)-trimethylsilane (5.5 g, 31.6 mmol), and $ZnCl_2$ (300 mg) in DCM (40 ml) was stirred at rt for 3 days. The reaction was monitored for the disappearance of the bromide by LCMS and worked up according to the literature reference.

2-Adamantan-1-yl-2-methyl-propionic acid

The methyl ester was dissolved in DMSO (15 ml) and treated with NaSMe (6.654 g, 9.3 mmol, 2 equiv.) and heated at 80° C. for 3 h. The reaction was cooled to room temperature and treated with 100 ml of water, extracted with $Et_2O$ and the layers were then separated. The aqueous layer was acidified to ph 3 to give 1.07 g of 2-Adamantan-1-yl-2-methyl-propionic acid as a white solid.

2-Adamantan-1-yl-2-methyl-propionyl chloride

2-Adamantan-1-yl-2-methyl-propionyl chloride was prepared via treatment with $SOCl_2$ at reflux for 1 to 2 h. Excess reagent was removed under reduced pressure and the mixture azeotroped with hexanes and the resulting acid chloride was used without further purification in the next step.

Intermediate 6 and 7

Preparation of 2-Methyl-2-(3,5,7-trimethyl-adamantan-1-yl)-propionyl chloride and 2-(3,5-dimethyl-adamantan-1-yl)-2-methyl-propionyl chloride

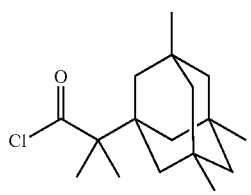

Intermediate 6

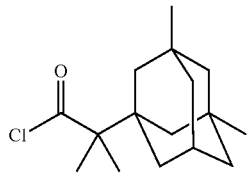

Intermediate 7

Prepared in an analogous manner to that for 2-Adamantan-1-yl-2-methyl-propionyl chloride, Intermediate 5.

Method B

Representative Synthesis of Compound 341

N-(7-Benzyl-5,6,7,8-tetrahydro-pyrido[3,4-d]pyrimidin-4-yl)-2-(3,5-dimethyl-adamantan-1-yl)-acetamide

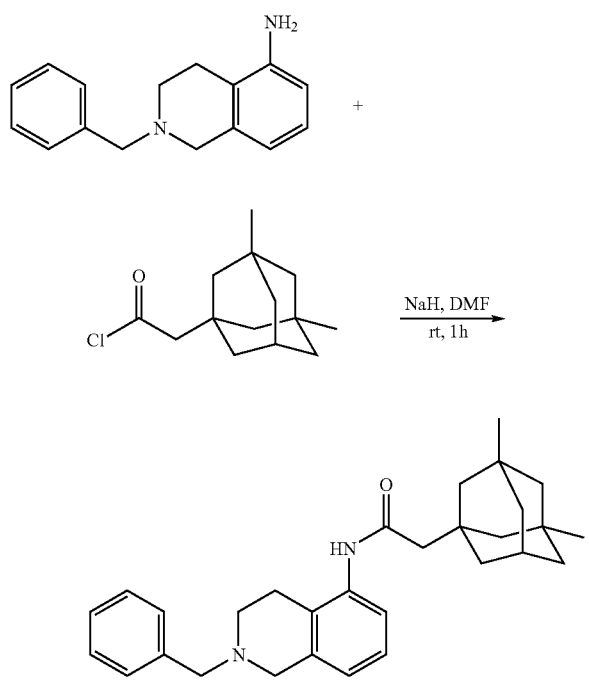

The reaction was performed in DMF under an inert atmosphere as follows: 7-benzyl-5,6,7,8-tetrahydropyrido[3,4-d]pyrimdin-4-amine (30 mg, 0.012 mmol) in 1 ml of DMF was treated with 15 mg of NaH and the result stirred at rt for 10 minutes. 40 uL intermediate 3 was added and stirring continued for 1 h at rt. After quenching with water (8 ml) and Satd. NaHCO₃ (10 ml) the resulting mixture was extracted with Et₂O. The combined organics were concentrated under reduced pressure to give the crude product, which was purified by HPLC to give the pure product (19 mg, 0.042 mmol) in a 35% yield.

Representative Synthesis of Compound 334

Adamantane-1-carboxylic acid(7-benzyl-5,6,7,8-tetrahydro-pyrido[3,4-d]pyrimidin-4-yl)-amide

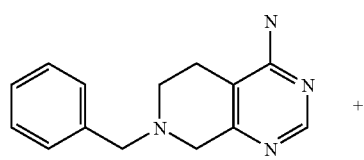

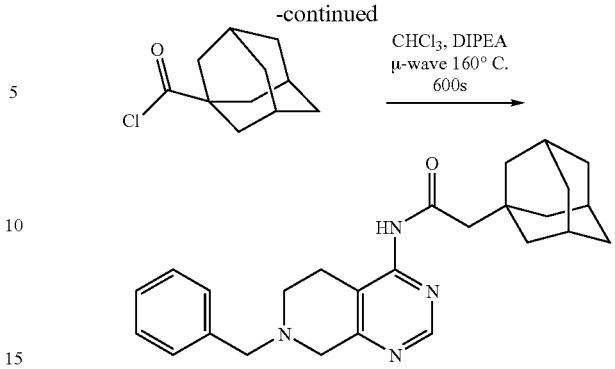

In a 20 ml microwave vessel was added 7-benzyl-5,6,7,8-tetrahydro-pyrido[3,4-d]pyrimidin-4-ylamine (1.5 g, 6.3 mmole) in 7.0 ml of chloroform, diisopropylethylarnine (2.2 ml, 12.6 mmole) and 1-adamantane carbonylchloride (2.51 g, 12.6 mmole). The reaction was heated at 160° C. for 7.0 minutes in a microwave. After completion the solvent was evaporated and the residue was dissolved in EtOAc and washed with sat. NaHCO₃, washed with brine and dried over sodium sulphate. The solvents were removed under reduced pressure and the residue was chromatographed using chloroform (100%) to give the desired product as a white solid (1.06 g).

ESI-MS m/z 403 [M+H]⁺.

The following examples were prepared in a manner analogous to that given for Method A or Method B using 7-benzyl-5,6,7,8-tetrahydropyrido[3,4-d]pyrimidin-4-amine and the appropriate intermediate acid or acid chloride as listed in the table below.

Compound 9

Prepared by reacting 7-benzyl-5,6,7,8-tetrahydropyrido[3,4-d]pyrimidin-4-amine with cyclohexylacetyl chloride.

Compound 10

Prepared by reacting 7-benzyl-5,6,7,8-tetrahydropyrido[3,4-d]pyrimidin-4-amine with cycloheptylacetyl chloride.

Compound 24

Prepared by reacting 7-benzyl-5,6,7,8-tetrahydropyrido[3,4-d]pyrimidin-4-amine with 3-(3-methoxyphenyl)propanoyl chloride.

Compound 339

Prepared by reacting 7-benzyl-5,6,7,8-tetrahydropyrido[3,4-d]pyrimidin-4-amine with Intermediate 5.

Compound 341

Prepared by reacting 7-benzyl-5,6,7,8-tetrahydropyrido[3,4-d]pyrimidin-4-amine with Intermediate 3.

Compound 343

Prepared by reacting 7-benzyl-5,6,7,8-tetrahydropyrido[3,4-d]pyrimidin-4-amine with Intermediate 7.

Compound 344

Prepared by reacting 7-benzyl-5,6,7,8-tetrahydropyrido[3,4-d]pyrimidin-4-amine with Intermediate 4.

Compound 345

Prepared by reacting 7-benzyl-5,6,7,8-tetrahydropyrido[3,4-d]pyrimidin-4-amine with Intermediate 6.

Compound 346

Prepared by reacting 7-benzyl-5,6,7,8-tetrahydropyrido[3,4-d]pyrimidin-4-amine with 3,5,7-trimethyl-adamantane-1-carbonyl chloride.

The following examples were prepared by debezylation of the corresponding N-benzyl derivatives and in a manner analogous to that given for the preparation of 2-adamantan-1-yl-N-(5,6,7,8-tetrahydro-pyrido[3,4-d]pyrimidin-4-yl)-acetamide (Compound 6).

Compound 11

Prepared by debenzylation of Compound 9.

Compound 12

Prepared by debenzylation of Compound 10.

Compound 25

Prepared by debenzylation of Compound 24.

Intermediate 8

2-Adamantan-1-yl-N-(5,6,7,8-tetrahydro-pyrido[3,4-d]pyrimidin-4-yl)-isobutyramide Prepared by debenzylation of Compound 339.

Intermediate 9

2-(3,5-Dimethyl-adamantan-1-yl)-N-(5,6,7,8-tetrahydro-pyrido[3,4-d]pyrimidin-4-yl)-acetamide Prepared by debenzylation of Compound 341

Intermediate 10

Preparation of Adamantane-1-carboxylic acid(5,6,7,8-tetrahydro-pyrido[3,4-d]pyrimidin-4-yl)-amide

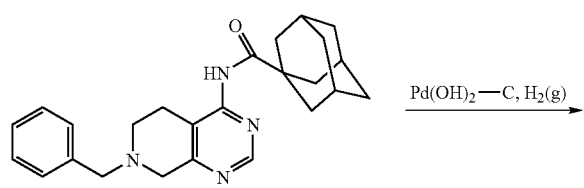

Pd(OH)₂—C, H₂(g)

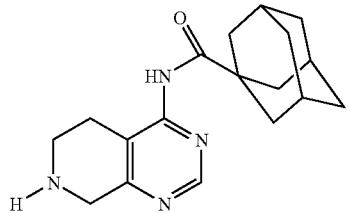

Adamantane-1-carboxylic acid (7-benzyl-5,6,7,8-tetrahydro-pyrido[3,4-d]pyrimidin-4-yl)-amide (1.1 g, 2.64 mmole) was suspended in 30 ml of methanol. To the mixture was added palladium hydroxide on carbon (20% wt, 0.41 g) and the reaction was shaken under 60 PSI of hydrogen gas for 16 hrs. The mixture was filtered through celite and the filtrate was concentrated to give the desired product as an off white solid (0.8 g).

ESI-MS m/z 313 [M+H]⁺.

General methods for the preparation of substituted 5,6,7,8-tetrahydropyrido[3,4-d]pyrimidin-4-yl acetamides

Method C

Representative Synthesis of Compound 46

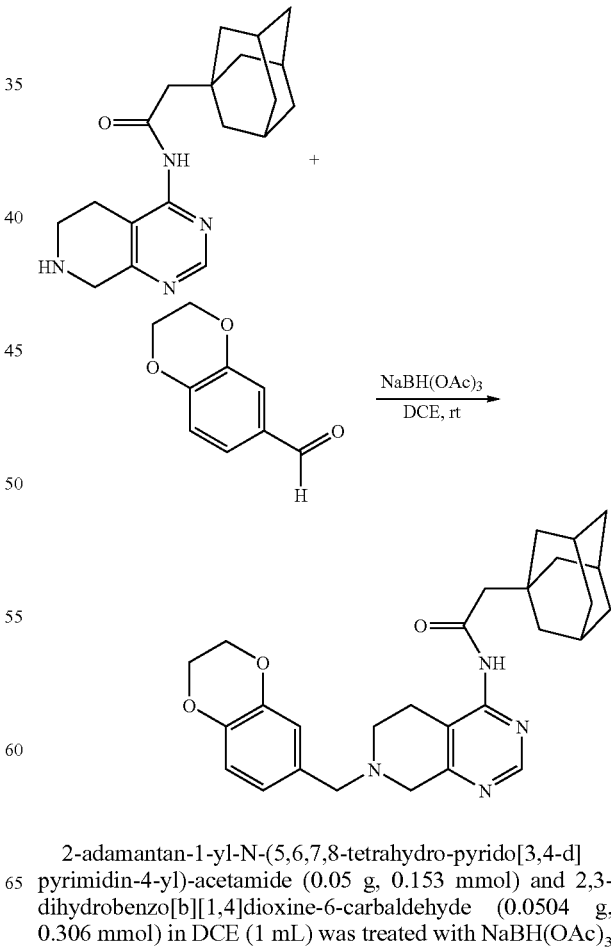

2-adamantan-1-yl-N-(5,6,7,8-tetrahydro-pyrido[3,4-d]pyrimidin-4-yl)-acetamide (0.05 g, 0.153 mmol) and 2,3-dihydrobenzo[b][1,4]dioxine-6-carbaldehyde (0.0504 g, 0.306 mmol) in DCE (1 mL) was treated with NaBH(OAc)₃

(0.065 g, 0.306 mmol) and the resulting mixture agitated overnight at room temperature. The crude reaction was purified by HPLC affording the desired compound.

LCMS (ESI⁺) m/z 474.9 [+H]⁺

NMR (300 MHz, CD$_3$OD): δ 8.65 (s, 1H), 6.86-6.79 (m, 3H), 4.21 (s, 4H), 3.62 (m, 4H), 2.76 (s, 4H), 2.22 (s, 2H), 1.97 (br s, 3H), 1.74-1.64 (m, 12H).

The reductive alkylation products with other aldehydes and ketones to obtain specified examples in Table 1A-1E were obtained in an analogous manner by using 2-adamantan-1-yl-N-(5,6,7,8-tetrahydro-pyrido[3,4-d]pyrimidin-4-yl)-acetamide, or the appropriate corresponding amine (0.05 g, 0.153 mmol) and 2 mmol of the corresponding aldehyde or ketone and reducing agent.

Method D

Representative Example (Compound 361)

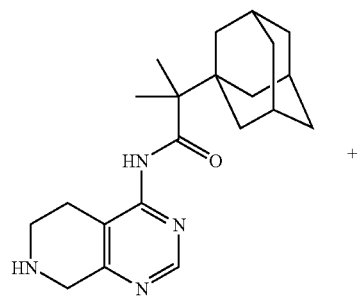

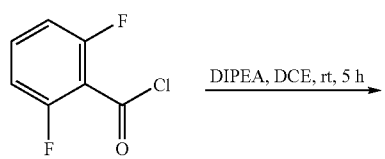

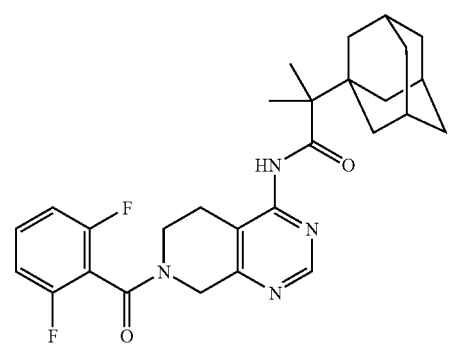

To a solution of 1,1-dimethyl-2-adamantyl-N-(5,6,7,8-tetrahydropyrido[3,4-d]pyrimidin-4-yl)acetamide (29 mg, 0.082 mmol) in anhydrous dichloroethane (2 mL) was added diisopropylethylamine (0.04 mL, 0.24 mmol) and 2,6-difluorobenzoyl chloride (21.7 mg, 0.12 mmol) at room temperature. After stirring at room temperature for 5 h, the reaction was quenched with water (0.5 mL) and evaporated to dryness. The dry residue was purified by prep-HPLC directly and afforded desired product.

LCMS (ESI⁺) m/z 495.3 [M+H]⁺

NMR (300 MHz, CDCl$_3$): δ 8.80 (s, 0.5H), 8.72 (s,0.5H), 7.64 (m, 1H), 7.37 (m, 1H), 6.97 (m, 2H), 5.01 (s, 1H), 4.56 (s, 1H), 4.04 (t, 1H), 3.57 (t, 1H), 2.85 (t, 1H), 2.75 (t, 1H), 2.03 (br m, 3H), 1.57-1.73 (m, 12H), 1.27 (s, 3H), 1.24 (s, 3H).

Specific representative examples of N-benzoyl and N-sulfonyl derivatives of 1,1-dimethyl-2-adamantyl-N-(5,6,7,8-tetrahydropyrido[3,4-d]pyrimidin-4-yl)acetamide given in Table 1A-1E can be or were prepared in an analogous manner by using either 1,1-dimethyl-2-adamantyl-N-(5,6,7, 8-tetrahydropyrido[3,4-d]pyrimidin-4-yl)acetamide (29 mg, 0.082 mmol) or 2-(3,5-dimethyl)adamantyl-N-(5,6,7,8-tetrahydropyrido[3,4d]pyrimidin-4-yl)acetamide (26 mg, 0.073 mmol), and 0.12 mmol of the corresponding acyl chlorides and sulfonyl chlorides.

Method E

A parallel synthetic method for N-benzoylation of 2-Adamantan-1-yl-N-(7-benzyl-5,6,7,8-tetrahydro-pyrido[3,4-d]pyrimidin-4-yl)acetamide Representative Synthesis of Compound 220

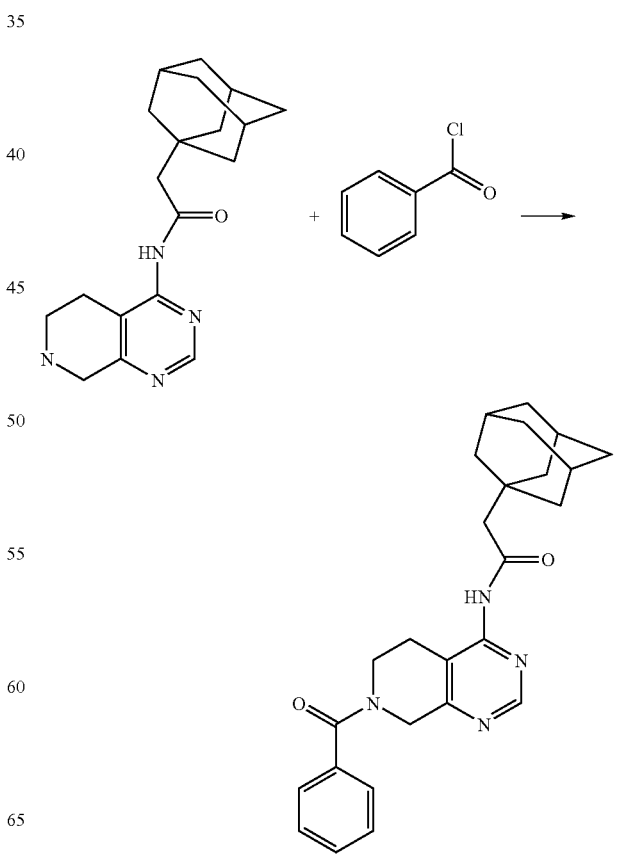

In one well of a 96-well polypropylene reaction plate was added 2-Adamantan-1-yl-N-(7-benzyl-5,6,7,8-tetrahydropyrido[3,4-d]pyrimidin-4-yl)acetamide (3.27 mg, 10 μmol) in 100 μl of anhydrous chloroform. To the reaction was added benzoyl chloride (2.1 mg, 15 μmol), followed by diisopropylethylamine (5.2 mg, 40 μmol). The reaction plate was heated at 50° C. for 15 minutes and the solvent was evaporated. The residue was dissolved in DMSO and purified using LC-MS based purification.

ESI-MS m/z 431 [M+H]⁺.

Specified examples of Table 1A-1E compounds were prepared in an analogous manner using the appropriate acyl chloride

Method F

A parallel synthetic method method for N-Sulphonylation of 2-Adamantan-1-yl-N-(7-benzyl-5,6,7,8tetrahydropyrido[3,4-d]pyrimidin-4-yl)acetamide Representative Example (Compound 143)

Method G

A parallel synthetic method for N-benzylation of 2-Adamantan-1-yl-N-(7-benzyl-5,6,7,8-tetrahydropyrido[3,4-d]pyrimidin-4-yl)acetamide Representative Example (Compound 5)

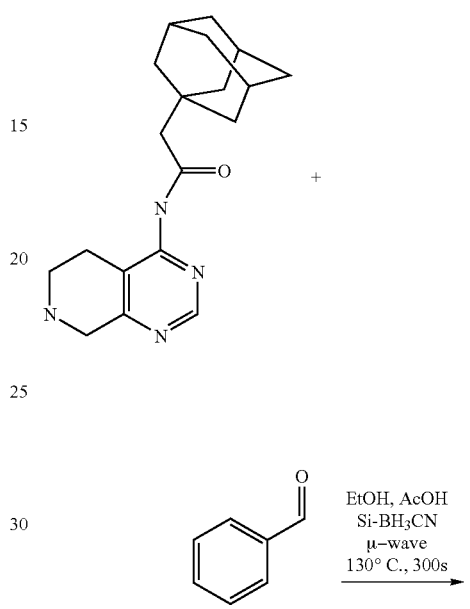

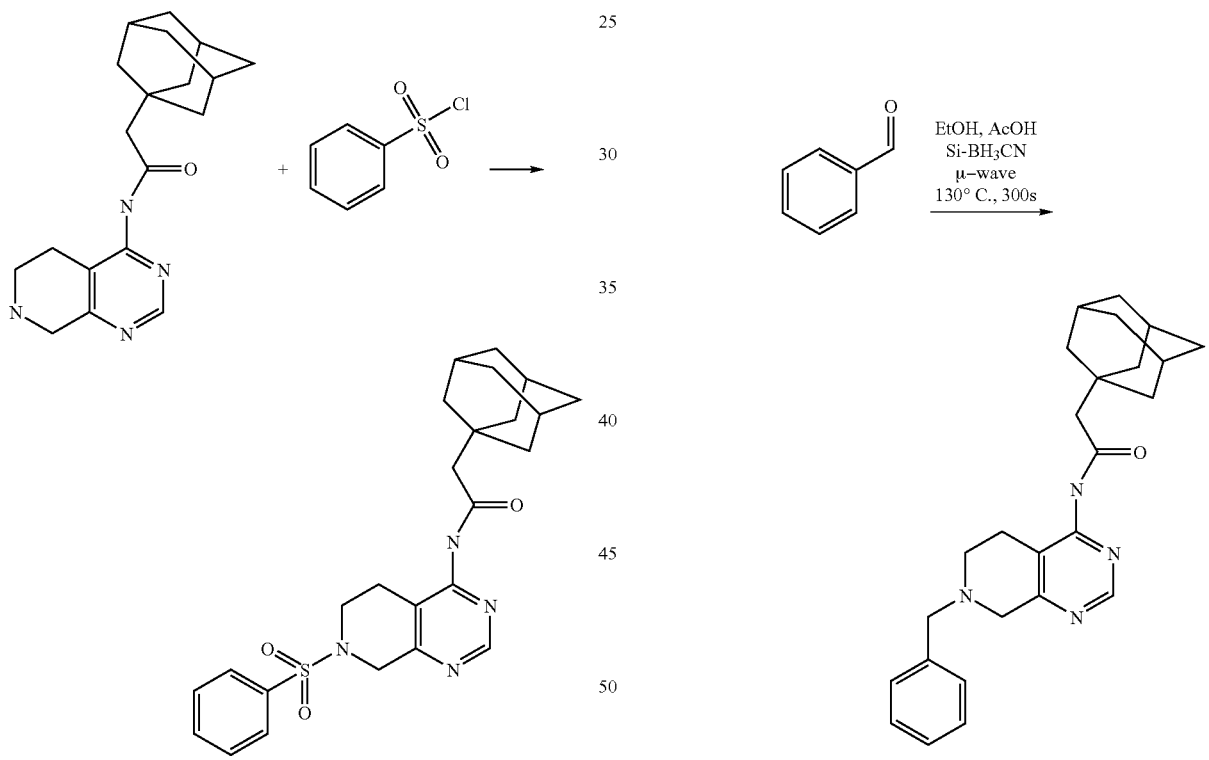

In one well of a 96-well polypropylene reaction plate was added 2-2-Adamantan-1-yl-N-(7-benzenesulfonyl-5,6,7,8-tetrahydropyrido[3,4-d]pyrimidin-4-yl)acetamide (3.27 mg, 10 μmol) in 100 μl of anhydrous chloroform. To the reaction was added benzenesulphonyl chloride (2.64 mg, 15 μmol), followed by diisopropylethylamine (5.2 mg, 40 μmol). The reaction plate was heated at 50° C. for 15 minutes and the solvent was evaporated. The residue was dissolved in DMSO and purified using LC-MS based purification ESI-MS m/z 467 [M+H]⁺.

Specified examples of Table 1A-1E compounds were prepared in an analogous manner using the appropriate sulphonyl chloride.

In a 2.0 ml -wave vessel was added 2-Adamantan-1-yl-N-(7-benzenesulfonyl-5,6,7,8-tetrahydropyrido[3,4-d]pyrimidin-4-yl)acetamide (3.27 mg, 10 mol) in 600 μl of absolute ethanol. To the reaction was added benzaldehyde (2.1 mg, 15 mol), followed by acetic acid (60 l) and silica bound sodium cyanoborohydride (15 mg, 15 mol). The reaction was heated at 120° C. for 5 minutes and the solvent was evaporated. The residue was dissolved in DMSO and purified using LC-MS based purification.

ESI-MS m/z 417 [M+H]⁺.

Specified examples of Table 1A-1E compounds were prepared in an analogous manner using the appropriate aldehyde

Method H

A parallel synthetic method for N-benzoylation of Adamantane-1-carboxylic acid(5,6,7,8-tetrahydro-pyrido[3,4-d]pyrimidin-4-yl)-amide Representatitive Example (Compound 394)

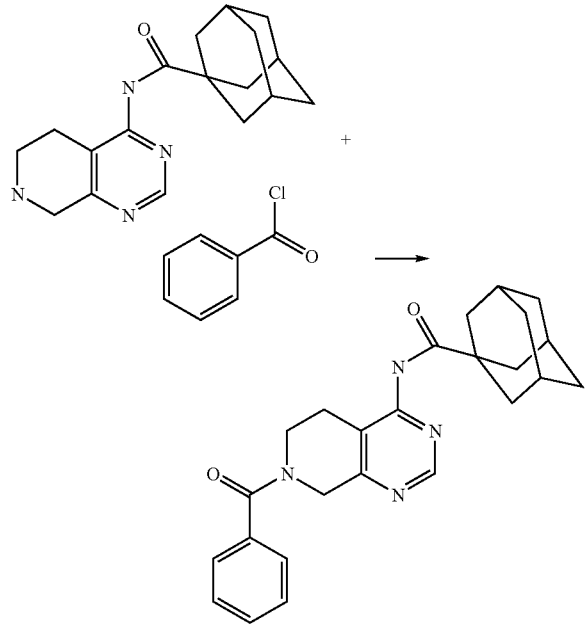

In one well of a 96-well polypropylene reaction plate was added adamantane-1-carboxylic acid(5,6,7,8-tetrahydro-pyrido[3,4-d]pyrimidin-4-yl)-amide (3.12 mg, 10 μmol) in 100 μl of anhydrous chloroform. To the reaction was added benzoyl chloride (2.1 mg, 15 μmol), followed by diisopropylethylamine (5.2 mg, 40 μmol). The reaction plate was heated at 50° C. for 15 minutes and the solvent was evaporated. The residue was dissolved in DMSO and purified using LC-MS based purification.

ESI-MS m/z 417 [M+H]+.

Specified examples of Table 1A-1E compounds were prepared in an analogous manner using the appropriate acyl chloride

Method 1

A parallel synthetic method for N-Sulphonylation of Adamantane-1-carboxylic acid (5,6,7,8-tetrahydro-pyrido[3,4-d]pyrimidin-4-yl)-amide Representative Example (Compound 481)

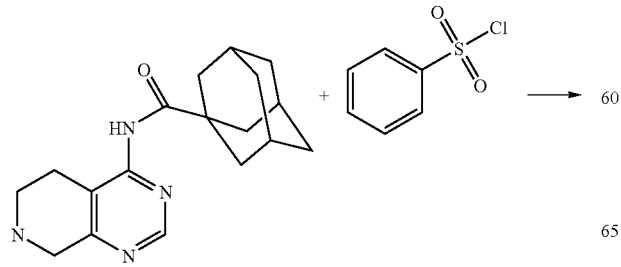

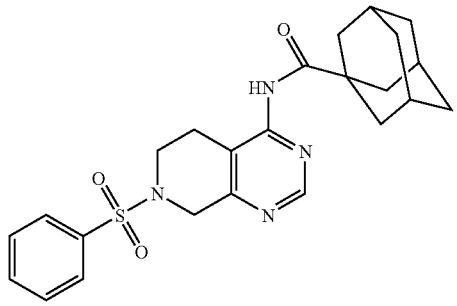

In one well of a 96-well polypropylene reaction plate was added 2-adamantane-1-carboxylic acid(5,6,7,8-tetrahydro-pyrido[3,4-d]pyrimidin-4-yl)-amide (3.12 mg, 10 μmol) in 100 μl of anhydrous chloroform. To the reaction was added benzenesulphonyl chloride (2.64 mg, 15 μmol), followed by diisopropylethylamine (5.2 mg, 40 μmol). The reaction plate was heated at 50° C. for 15 minutes and the solvent was evaporated. The residue was dissolved in DMSO and purified using LC-MS based purification.

ESI-MS m/z 453 [M+H]+.

Specified examples of Table 1A-1E compounds were prepared in an analogous manner using the appropriate sulphonyl chloride.

Method J

A parallel synthetic method for N-benzylation of Adamantane-1-carboxylic acid (5,6,7,8-tetrahydro-pyrido[3,4-d]pyrimidin-4-yl)-amide Representative Example (Compound 334)

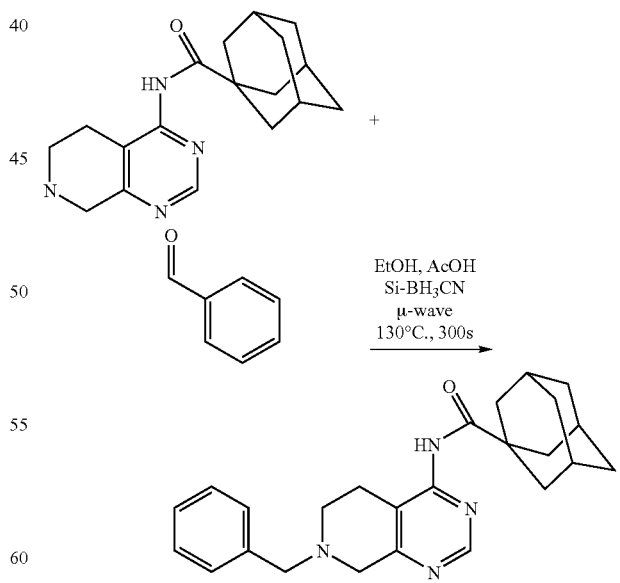

In a 2.0 ml microwave vessel was added adamantane-1-carboxylic acid (5,6,7,8-tetrahydro-pyrido[3,4-d]pyrimidin-4-yl)-amide (3.12 mg, 10 μmol) in 600 μl of absolute ethanol. To the reaction was added benzaldehyde (2.1 mg, 15 μmol), followed by acetic acid (60 μl) and silica bound sodium cyanoborohydride (15 mg, 15 µmol). The reaction was heated at 120° C. for 5 minutes and the solvent was evaporated. The residue was dissolved in DMSO and purified using LC-MS based purification ESI-MS m/z 403 [M+H]$^+$.

Specified examples of Table 1A-1E compounds were prepared in an analogous manner using the appropriate aldehyde.

Intermediate 11

Preparation of 7-benzyl-5,6,7,8-tetrahydropyrido[3,4-d]pyrimidine-4-carboxylic acid a) 7-Benzyl-5,6,7,8-tetrahydropyrido[3,4-d]pyrimidine-4-carbonitrile

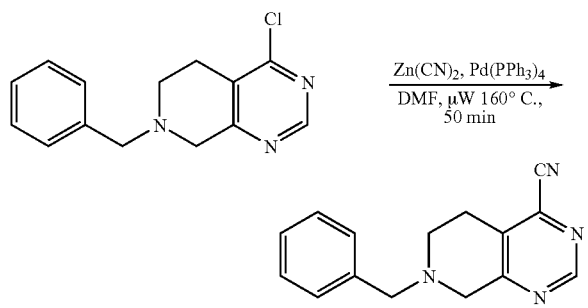

Four 10-20 mL microwave vials were each charged with 7-benzyl-4-chloro-5,6,7,8-tetrahydropyrido[3,4-d]pyrimidine (1 g, 4 mmol), Pd((PPh3)$_4$ (500 mg, 0.4 mmol) and Zn(CN)$_2$ (300 mg, 2 mmol) were suspended in dry DMF (7 mL). These sealed suspensions were then heated at 160° C. for 50 min in a microwave reactor. After cooling the reaction mixture an aliquot was taken and the sample tested by LCMS. The reaction showed 100% conversion of 7-benzyl-4-chloro-5,6,7,8-tetrahydropyrido[3,4-d]pyrimidine to desired product. The crude reaction mixtures were poured into water (200 mL), resulting in the precipitation of a brown solid, which was filtered and dried. The aqueous filtrate was extracted with DCM (2×100 mL). The organic layer was filtered through a Horizon Technology DryDisk and concentrated. The crude solids and oil were purified via column chromatography first with DCM/MeOH (20:1)of 7-benzyl-5,6,7,8-tetrahydropyrido[3,4-d]pyrimidine-4-carbonitrile. (2.1 g, 55%)

ESI-MS n/z 251.3 [M+H]$^+$.

$^1$H NMR (300 MHz, CD$_3$OD) δ 8.99 (s, 1H), 7.4-7.3 (m, 5H), 3.79 (s, 2H), 3.73 (s, 2H), 3.05 (t, 2H), 2.91 (t, 2H).

b) Methyl 7-benzyl-5,6,7,8-tetrahydropyrido[3,4-d]pyrimidine-4-carboxylate

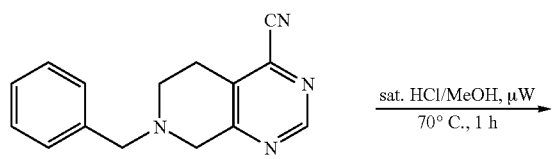

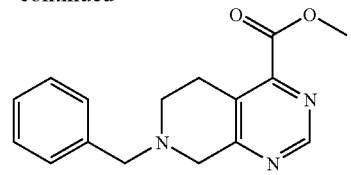

7-benzyl-5,6,7,8-tetrahydropyrido[3,4-d]pyrimidine-4-carbonitrile (2.1 g, 8.38 mmol) was dissolved in satd. solution of HCl/MeOH (15 mL) in a microwave tube. The vial was heated in a microwave reactor at 70° C. for 1 h. The reaction was cooled and depressurized and concentrated under reduced pressure. The crude oil was dissolved in MeOH followed by removal of MeOH under reduced pressure to assist with the remove of excess HCl. The red-brown oil was dissolved in minimal amount of water (10 mL) and added to an ice cold sat. NaHCO$_3$ solution (200 mL). The aqueous layer was extracted with DCM (3×100 mL). The combined organic layers were then filtered through a Horizon Technologies DryDisk and concentrated. The resulting red-brown oil was purified by flash chromatographed using DCM/MeOH (20:1) as elutant. The pure fractions were combined, treated with norite, filtered through a pad of celite and the filtrate concentrated to afford methyl 7-benzyl-5,6,7,8-tetrahydropyrido[3,4-d]pyrimidine-4-carboxylate (1.01 g, 42.3%.)

ESI-MS m/z 284.3 [M+H]$^+$.

$^1$H NMR (300 MHz, CD3OD) δ 8.94 (s, 1H), 7.4-7.3 (m, 5H), 3.96 (s, 3H), 3.76 (s, 2H), 3.73 (s, 2H), 3.15 (t,2H), 2.82 (t, 2H), c) 7-Benzyl-5,6,7,8-tetrahydropyrido[3,4-d]pyrimidine-4-carboxylic acid

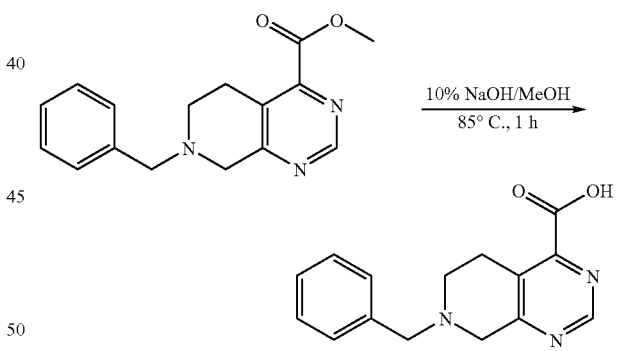

Methyl 7-benzyl-5,6,7,8-tetrahydropyrido[3,4-d]pyrimidine-4-carboxylate (0.2 g, 0.705 mmol) was dissolved in MeOH (10 mL). 10% NaOH solution (1.5 mL) was added. The solution was heated at 85° C. for 1 h. Solvent was removed under reduced pressure. The aqueous. layer was acidified to ca. pH 4. The aqueous layer was then extracted with DCM (2×50 mL) to remove organic impurities. The acidic aqueous layer was dried on the lyophilizer. The resulting solids were washed with MEOH (10 mL) and filtrate concentrated to give 7-benzyl-5,6,7,8-tetrahydropyrido[3,4-d]pyrimidine-4-carboxylic acid (0.173 g, 0.642 mmol, 91%) as a brown oil. The resulting product was used without further purification.

ESI-MS m/z 270.3 [M+H]$^+$.

$^1$H NMR (300 MHz, CD$_3$OD) δ 8.75 (s, 1H), 7.4-7.3 (m, 5H), 3.74 (s, 2H), 3.65 (s, 2H), 3.00 (t, 2H), 2.82 (t, 2H).

Preparation of Compound 17

7-Benzyl-N-adamantylmethyl-5,6,7,8-tetrahydropyrido[3,4-d]pyrimidine-4-carboxamide

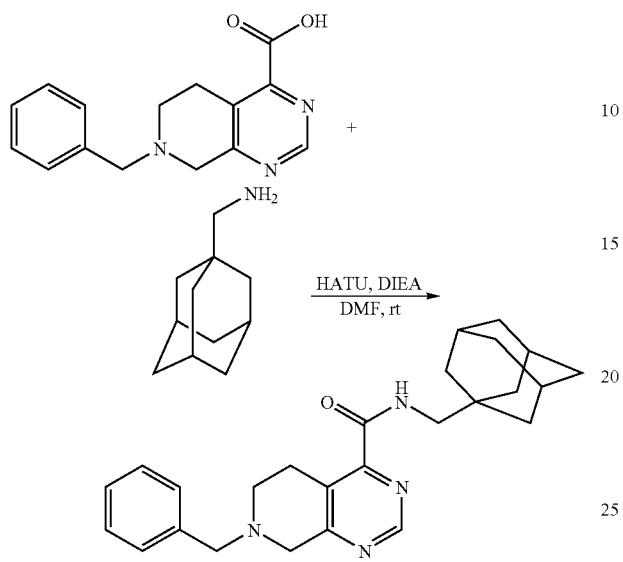

In a 2-dram vial, intermediate 11 (0.5 g, 1.85 mmol) was dissolved in DMF (1 mL) with 1-adamantyl methylamine (0.37 g, 2.24 mmol) and HATU (1.2 g, 2.8 mmol) followed by DIEA (300 µL, 2.79 mmol) was added to the mixture. The vial was sealed and placed on an orbital shaker for 16 h. The reaction mixture was diluted with DCM (50 mL). The organic layer was washed with sat. NaHCO$_3$ solution (1×25 mL) and water (1×25 mL). The organic layer was filtered through a Horizon Technologies DryDisk and concentrated. The crude product was purified by column chromatography to afford 7-benzyl-N-adamantylmethyl-5,6,7,8-tetrahydropyrido[3,4-d]pyrimidine-4-carboxamide (0.048 g 6.2%) which was taken on to the next step without further purification.

ESI-MS m/z 417.1 [M+H]$^+$.

$^1$H NMR (300 MHz, CD$_3$OD) δ 8.91 (s, 1H), 7.4-7.3 (m, 5H), 3.75 (s, 2H), 3.7 (s, 2H), 3.25 (t, 2H), 3.08 (s, 2H), 2.81 (t, 2H), 1.98 (s, 3H), 1.78-1.6 (m, 12H).

Intermediate 12

Preparation of 1-(aminomethyl)-3,3-dimethylcyclohexanol hydrochloride

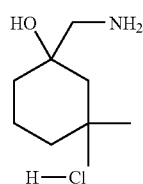

Prepared by standard LAH reduction in THF at 0° C. using 1.49 g (9.74 mmol) of 1-hydroxy-3,3-dimethylcyclohexanecarbonitrile and 740 mg (19.48 mmol) of LAH. The mixture was stirred at room temperature overnight. The mixture was quenched with 740 ul of water and 740 ul of 15% methanol in water, stirred for 2 hours and then filtered. The filtrate was washed with EtOAc, concentrated under reduced pressure and dried under high vacuum. The dark viscous oil was taken up in 50 ml of EtOAc and was treated with 20 ml of 4M HCl solution in 1,4-dioxane followed by 10% MeOH and then heated to ensure dissolution. Upon cooling to room temperature followed by further cooling to −78° C. 1 g (73%) of the recrystallized HCl salt of 1-(aminomethyl)-3,3-dimethylcyclohexanol was obtained.

Intermediates 13, 14 and 15

Preparation of 1-(aminomethyl)cycloheptanol, (1-p-tolylcyclohexyl)methanamine and cycloheptylmethanamine Intermediate 13

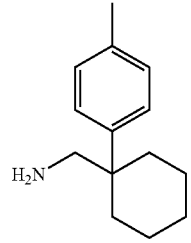

Intermediate 14

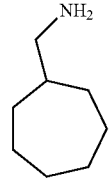

Intermediate 15

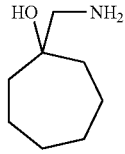

The title intermediates were prepared in an analogous manner to that for 1-(aminomethyl)-3,3-dimethylcyclohexanol using the appropriate nitrile.

Preparation of Compounds 1, 4, 58, 59 and 60 and 1

The title compounds were prepared in a manner analogous to that given for Compound 17 using the Intermediate 11 and the appropriate amine.

Intermediate 16

Preparation of 5,6,7,8-tetrahydro-pyrido[3,4-d]pyrimidine-4-carboxylic acid (adamantan-1-ylmethyl)-amide

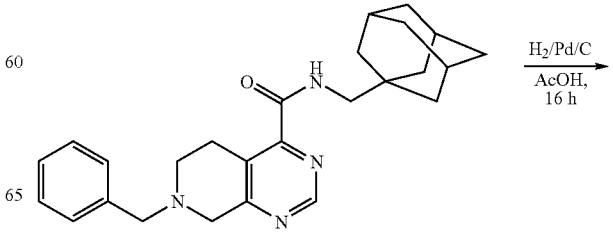

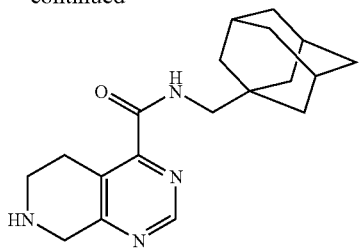

In a round bottom flask, 7-Benzyl-5,6,7,8-tetrahydro-pyrido[3,4-d]pyrimdine-4-carboxylic acid(adamantan-1-yl-methyl)-amide(1.15 g, 2.74 mmol) was dissolved in glacial acetic acid (10 mL) with stirring and 10% Pd/C (417 mg) was added. The suspension was stirred under an atmosphere of H₂ for 16 h. By LCMS and TLC (DCM:MeOH::20:1), no starting material appeared to be present. The desired m/z was observed at 327.3 (M+H). The reaction mixture was then filtered through a pad of celite. The filtrate was concentrated. The resulting oil was re-dissolved in EtOAc (50 mL) with stirring. A 10% NaOH solution (50 mL) was added. The mixture was stirred at RT for 1 h. The layers were separated and the aqueous layer was extracted with EtOAc (3×50 mL). The combined organic layers were filtered through a Horizon Technologies DryDisk and concentrated. The crude oil was chromatographed using DCM/MeOH (0-30% gradient) as elutant affording 0.133 g of the title compound.

ESI-MS m/z 327.3 [M+H]⁺.

¹H NMR (300 MHz, CD₃OD) δ 8.96 (s, 1H), 4.13 (s, 2H), 3.3-3.2 (m, 4H), 3.07 (s, 2H), 1.98 (s, 3H), 1.79-1.6 (m, 12H).

Preparation of Compounds 2 and 3

The title compounds were prepared in a manner analogous to that given for intermediate 16 using Compounds 4 and 1 as starting materials, respectively.

Method K

General procedure for the N-benzylation of 5,6,7,8-Tetrahydro-pyrido[3,4-d]pyrimidine-4-carboxylic acid (adamantan-1-ylmethyl)-amide Preparation of a representative example Compound 137

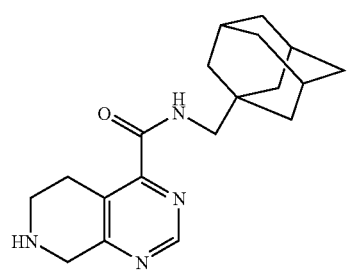

+

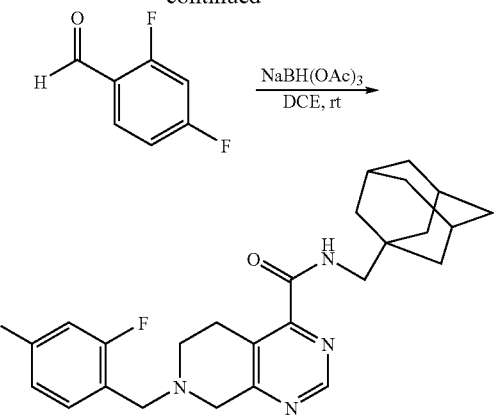

In a 2-dram vial, a solution of 5,6,7,8-Tetrahydro-pyrido[3,4-d]pyrimidine-4-carboxylic acid (adamantan-1-ylm-ethyl)-amide (0.44 g, 0.134 mmol) in DCE was added followed by 2,4-difluorbenzaldehyde (0.26 g, 0.18 mmol). The solution was placed on an orbital shaker at room temperature for 1 h. Sodium triacetoxyborohydride (0.43 g, 0.2 mmol) was added. The mixture was agitated for an additional 16 h at room temperature. LCMS and TLC (DCM:MeOH::20:1), indicated that no starting material remained. The reaction was quenched by the addition of MeOH (0.5 mL). The mixture was then filtered through a pad of celite®. The pad was subsequently washed with MeOH (2 mL). The filtrate was concentrated and the crude solid was purified via HPLC to yield the title compound (0.0166 g) as a yellow oil.

ESI-MS m/z 453.3 [M+H]⁺.

¹H NMR (300 MHz, CD₃OD) δ 8.92 (s, 1H), 7.51 (q,2H), 6.97, (t, 1H), 3.81 (s, 2H), 3.38 (s, 2H), 3.25 (t, 2H), 3.23 (s, 2H), 2.84 (t, 2H), 1.98 (s, 3H), 1.79-1.6 (m, 12H).

Specified examples of Table 1A-1E compounds were prepared from 5,6,7,8-tetrahydro-pyrido[3,4-d]pyrimidine-4-carboxylic acid(adamantan-1-ylmethyl)-amide, and Compound 2 in an analogous manner using the appropriate aldehyde.

Preparation of a Representative Example Compound 13

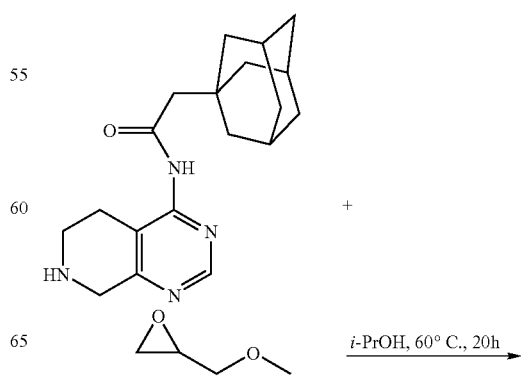

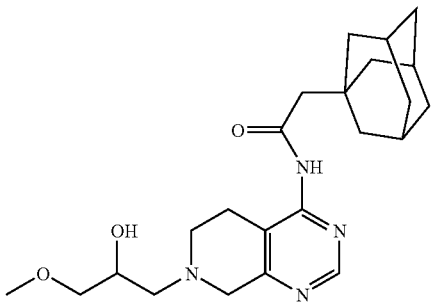

A solution of 2-adamantan-1-yl-N-(5,6,7,8-tetrahydro-pyrido[3,4-d]pyrimidin-4-yl)-acetamide (0.1 g, 0.306 mmol) and 2-Methoxymethyl-oxirane (0.035 g, 0.398 mmol) in i-PrOH (5 mL) was stirred at 60° C. for 20 h. The reaction vessel was allowed to cool to room temperature, opened, and the volatiles were removed under reduced vacuum. The crude product was purified by HPLC to afford 2-adamantan-1-yl-N-[7-(2-hydroxy-3-methoxy-propyl)-5,6,7,8-tetrahydro-pyrido[3,4-d]pyrimidin-4-yl]-acetamide (Compound 13) (0.0134 g, 0.032 mmol, 100%) in 100% purity as determined by LCMS.

ESI-MS m/z 415.5 [M+H]$^+$.

$^1$H-NMR (300 MHz, CDCl$_3$): δ 8.71 (s, 1H), 7.88 (s, 1H), 3.99 (m, 1H), 3.86 (d, 1H), 3.71 (d, 1H), 3.46 (m, 2H), 3.40 (s, 3H), 2.94 (m, 1H), 2.76 (m, 3H), 2.70-2.55 (m, 2H), 2.28 (s, 2H), 1.99 (br s, 3H), 1.74-1.65 (m, 12H).

Preparation of a Representative Example
Compound 23

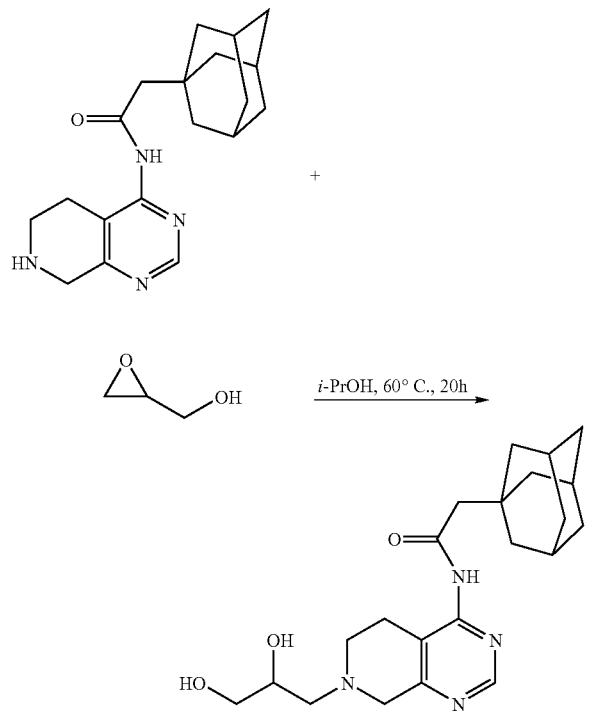

2-Adamantan-1-yl-N-[7-(2,3-dihydroxy-propyl)-5,6,7,8-tetrahydro-pyrido[3,4-d]pyrimidin-4-yl]-acetamide was synthesized from 2-adamantan-1-yl-N-(5,6,7,8-tetrahydro-pyrido[3,4-d]pyrimidin-4-yl)-acetamide (0.05 g, 0.153 mmol) and glycidol (0.015 g, 0.2 mmol) in i-PrOH (3 mL) in a manner analogous to the preparation of Compound 13. Preparative TLC purification using DCM/MeOH/TEA (10:1:1)) afforded the desired product (0.0074 mg, 12%).

ESI-MS m/z 401.3 [M+H]$^+$.

Preparation of a Representative Example
Compound 19

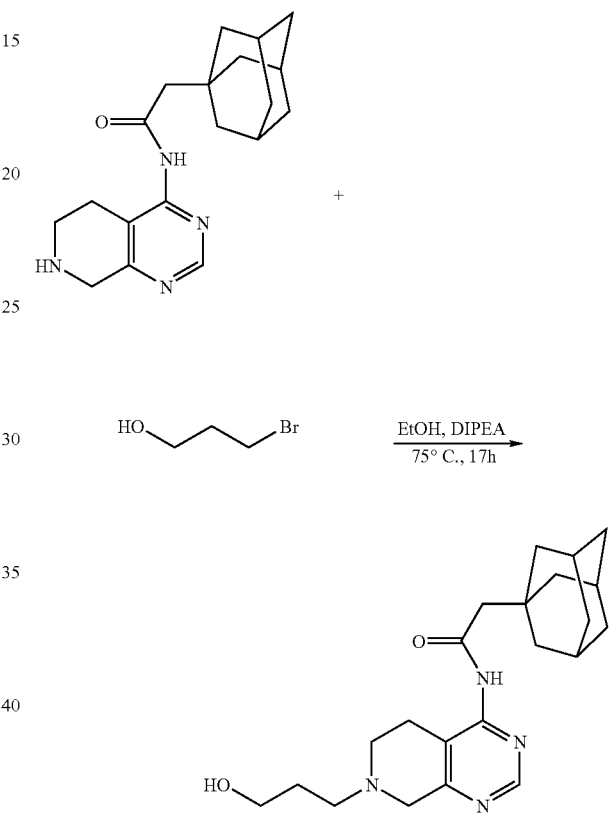

A solution of 2-adamantan-1-yl-N-(5,6,7,8-tetrahydro-pyrido[3,4-d]pyrimidin-4-yl)-acetamide (0.05 g, 0.153 mmol), 3-bromo-1-propanol (0.021 g, 0.15 mmol) and DIPEA (0.045 g, 0.35 mmol) in EtOH (4 mL) was stirred at 75° C. for 17 h. The reaction vessel was allowed to cool to room temperature, opened, and the volatiles were removed on a rotary evaporator. The residue was redissolved in THF (3 mL). PL-NCO resin (300 mg) was added, and the resulting suspension was stirred at room temperature for 16 h. The resin was filtered and the volatiles were removed under vacuum. The crude product was purified by HPLC to afford 2-adamantan-1-yl-N-[7-(3-hydroxy-propyl)-5,6,7,8-tetrahydro-pyrido[3,4-d]pyrimidin-4-yl]-acetamide (0.0098 g, 17%).

ESI-MS m/z 385.5 [M+H]$^+$.

$^1$H-NMR (300 MHz, CDCl$_3$): δ 8.71 (s, 1H), 7.65 (s, 1H), 3.82 (t, 2H), 3.75 (s, 2H), 2.86-2.75 (m, 6H), 2.30 (s, 2H), 1.99 (br's', 3H), 1.83 (m, 2H), 1.74-1.60 (m, 12H).

The title compound was prepared in a manner analogous to that given for Compound 21 using the appropriate starting material.

Preparation of a Representative Example Compound 18

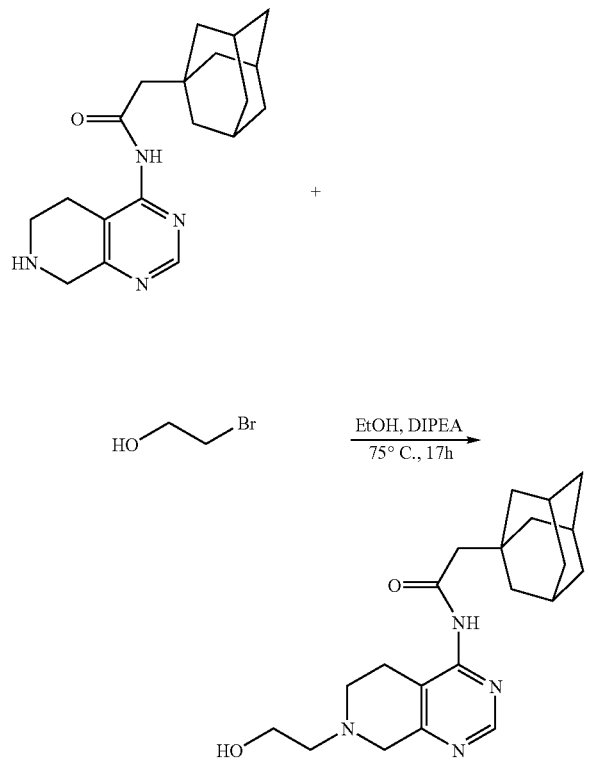

2-Adamantan-1-yl-N-[7-(2-hydroxy-ethyl)-5,6,7,8-tetrahydro-pyrido[3,4-d]pyrimidin-4-yl]-acetamide was synthesized from 2-adamantan-1-yl-N-(5,6,7,8-tetrahydro-pyrido[3,4-d]pyrimidin-4-yl)-acetamide (0.05 g, 0.153 mmol), 2-bromoethanol (0.019 g, 0.15 mmol) and DIPEA (0.052 g, 0.4 mmol) in EtOH (4 mL) in a manner analogous to compound 21 The crude reaction was purified by HPLC affording the desired product (0.0064 g, 0.017 mmol, 12%).
ESI-MS m/z 371.3 [M+H]$^+$.

Preparation of a Representative Example Compound 22

The title compound was prepared in a manner analogous to that given for Compound 21 using the appropriate starting materials.

Preparation of 7-Benzyl-3-methyl-5,6,7,8-tetrahydro-[2,7]naphthyridine-4carboxylic acid (adamantan-1-ylmethyl)-amide (Compound 368)

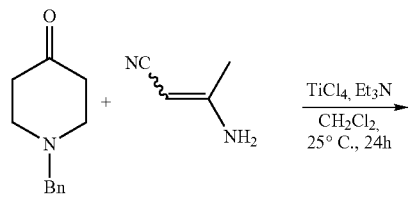

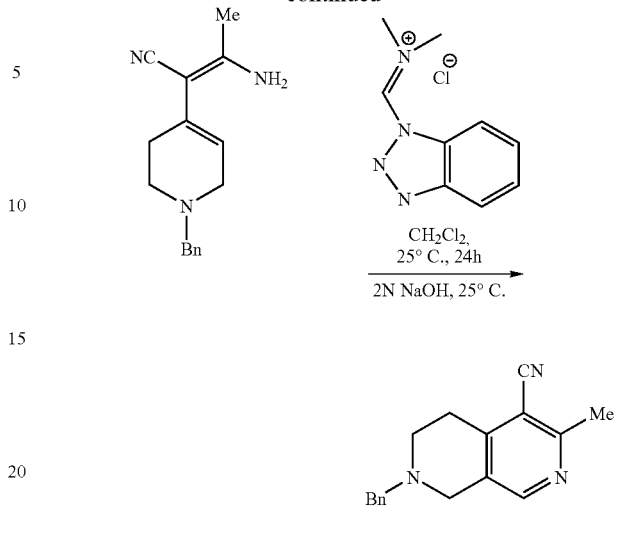

A solution of β-aminocrotononitrile (12 g, 147 mmol) and NEt$_3$ (37 mL, 266 mmol) in CH$_2$Cl$_2$ (150 mL) was cooled with an ice bath to 0°. TiCl$_4$ (7.9 mL, 72 mmol) in CH$_2$Cl$_2$ (100 mL) was added slowly with stirring followed by N-benzyl-4-piperidone (21.4 mL, 120 mmol) in one portion. The mixture was stirred for 24 h at ambient temperature and the volatiles were removed under reduced pressure. Ethly ether (400 mL) was added, and the resulting mixture was stirred vigorously until the residue was ground to a fine powder. The powder was filtered off and washed with ethyl ether (400 mL) and evaporation of the solvent afforded (E)-3-amino-2-(1-benzyl-1,2,3,6-tetrahydro-pyridin-4-yl)-but-2-enenitrile as an oil (20 g, 70%), which was used without further purification.

To a solution of (E)-3-amino-2-(1-benzyl-1,2,3,6-tetrahydro-pyridin-4-yl)-but-2-enenitrile (15 g, 0.056 mole) in dichloromethane (200 mL), freshly prepared benzotriazol-1-ylmethylene-dimethyl-ammonium chloride (12 g, 0.068 mole) was added in one portion. The mixture was stirred for 24 h at ambient temperature. NaOH (2N, 200 mL) was added, and the resulting mixture was stirred vigorously for 5 min. The phases were separated and the aqueous phase was extracted with dichloromethane (100 mL). The combined organic phases were dried over magnesium sulfate, and the solvent was removed in vacuo. The crude product was purified by column chromatography to give 7-benzyl-3-methyl-5,6,7,8-tetrahydro-2,7-naphthyridine-4-carbonitrile as a colorless oil (8.9 g, 53% yield).

$^1$H NMR (CDCl$_3$) δ 8.28 (s, 1H), 7.36-7.31 (m, 5H), 3.72 (s, 2H), 3.59 (s, 2H), 3.01 (t, 2H), 2.80 (t, 2H), 2.71 (s, 3H)

Preparation of 7-benzyl-3-methyl-5,6,7,8-tetrahydro-[2,7]naphthyridine-4-carboxylic acid amide

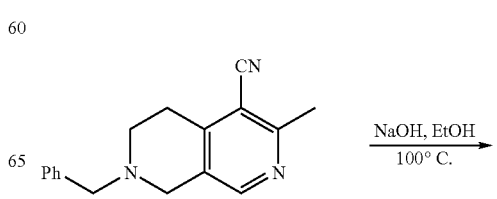

-continued

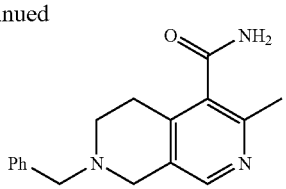

NaOH (9.1 mg, 2.24 mmol) was added to 0.5 ml of EtOH, which contained 30 mg (0.114 mmol) of the nitrile and the resulting mixture was heated at 100° C. overnight. The mixture was acidified by concentrated HCl to pH>2 and extracted with dichloromethane. The pH of the aqueous layer was then adjusted to 7 and extracted with dichloromethane. The combined DCM layers were washed with brine, dried, and concentrated under reduced pressure to afford the crude product, which was purified by column chromatography using MeOH:DCM (3-25%) to afford the pure product (22 mg, 0.078 mmol) in a 69% yield.

Preparation of 7-benzyl-3-methyl-5,6,7,8-tetrahydro-[2,7]naphthyridine-4-carboxylic acid(adamantan-1-ylmethyl)-amide

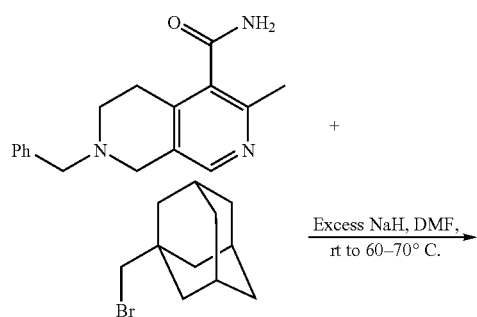

7-benzyl-5,6,7,8-tetrahydro-3-methyl-2,7-naphthyridine-4-carboxamide (40 mg, 0.142 mmol) was taken up in anhydrous DMF (0.5 ml) under an inert atmosphere. NaH (60% in mineral oil) (6.8 mg, 0.17 mmol) was added to the reaction vessel and the mixture stirred for 30 minutes until the evolution of hydrogen gas ceased. To this mixture was added 1-adamantylmethylbromide in DMF (0.5 ml) and reaction was stirred at room temperature for 4 hr. The reaction was monitored by TLC and LCMS. Excess NaH and 1-adamantylmethylbromide and heated from 40 to 75° C. for 3 days. The mixture was cooled to room temperature, and added to ice water. The aqueous layer was extracted with EtOAc, washed with water, brine, dried over sodium sulfate, and reduced in vacuo. The crude was purified by flash chromatography followed by prep. TLC using MeOH:DCM (5-10%) to afford the title compound. (5 mg, 8%).

Preparation of 2-Adamantan-1-yl-N-(7-benzyl-5,6,7,8-tetrahydro-[1,7]naphthyridin-4-yl)-acetamide (Compound 342)

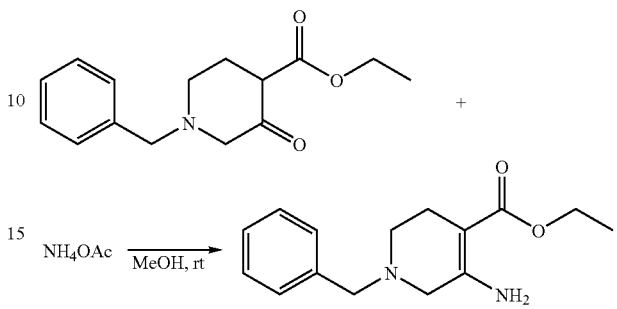

Preparation of 5-amino-1-benzyl-1,2,3,6-tetrahydropyridine-4-carboxylic acid ethyl ester Ethyl 1-benzyl-3-oxopiperidine-4-carboxylate (25 g, 83.96 mM) and ammonium acetate (32.36 g, 419.79 mM) in MeOH (250 mL) were agitated overnight. The mixture was concentrated, the crude product was dissolved in methylene chloride and washed sequentially with aqueous saturated potassium carbonate solution and water. The organic was dried and reduced in vacuo to yield the title compound (24.0 g, 110%, higher yield possibly due to accluded solvents) as an oil which solidified on standing.

Preparation of 7-benzyl-4-hydroxy-5,6,7,8-tetrahydro-[1,7]naphthyridine-3-carboxylic acid methyl ester

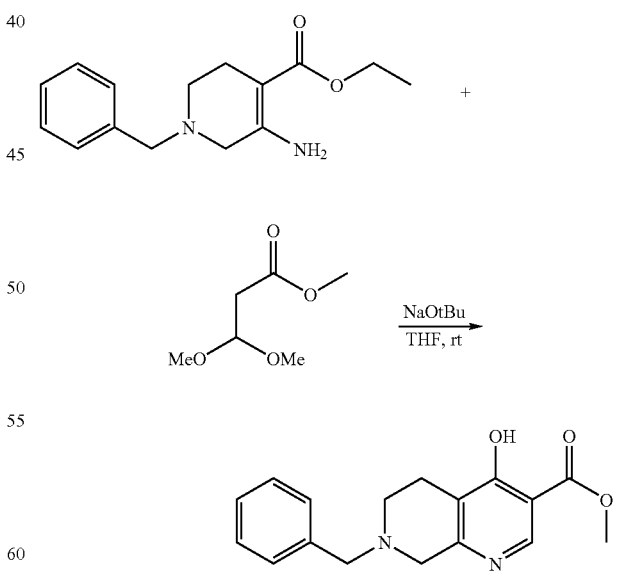

To a suspension of NaOtBu (4.23 g, 34.57 mM) in THF (50 mL) was added a mixture of ethyl 3-amino-1-benzyl-1,2,5,6-tetrahydropyridine-4-carboxylate (3.0 g, 11.52 mM) and methyl 3,3-dimethoxypropanoate (5.12 g, 34.57 mM) in THF (20 mL) in one portion and the mixture was agitated at ambient temperature overnight. The mixture was concentrated to half the volume before being quenched with ice-cold water. The homogeneous solution was extracted ethyl ether and the aqueous layer was carefully acidified with HCl until acidic. The precipitate was filtered, washed with water, and dried under vacuum to obtain the title compound as an off-white solid (1.6 g, 47%).

Preparation of 7-benzyl-4-hydroxy-5,6,7,8-tetrahydro-[1,7]naphthyridine-3-carboxylic acid

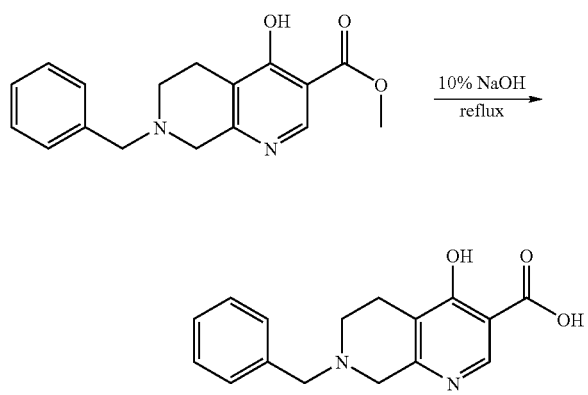

In a round bottom flask, 7-Benzyl-4-hydroxy-5,6,7,8-tetrahydro-[1,7]naphthyridine-3-carboxylic acid methyl ester (56 mg) was dissolved in methanol (15 mL) and a 10% NaOH solution in water (5 mL) was added with stirring. The mixture was heated at reflux for 2 hours, reduced in vacuo, and the aqueous remainder was acidified with 1N HCl. The aqueous layer was extracted with with dichloromethane. The aqueous layer was concentrated to give 0.06 grams of the product as its hydrochloride salt after drying.

d)
7-Benzyl-5,6,7,8-tetrahydro-[1,7]naphthyridin-4-ol

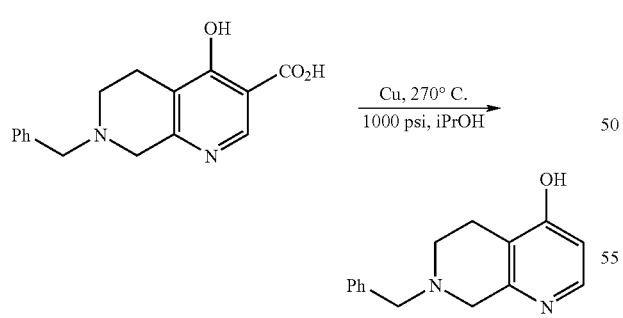

7-Benzyl-4-hydroxy-5,6,7,8-tetrahydro-[1,7]naphthyridine-3-carboxylic acid (0.025 g, 0.089 mmol) in 2 ml of I-PrOH and column packed with Cu(O) was heated to 270° C. under 1000 psi in a continuous flow reactor. The flow rate was adjusted to 1.5 μl/min. After cooling, filtering, and washing with methanol the filtrate was concentrated to afford 50 mg (0.208 mmol) of the desired product.

ESI-MS m/z 241.1 [M+H]$^+$.

Preparation of 7-benzyl-4-chloro-5,6,7,8-tetrahydro-[1,7]naphthyridine

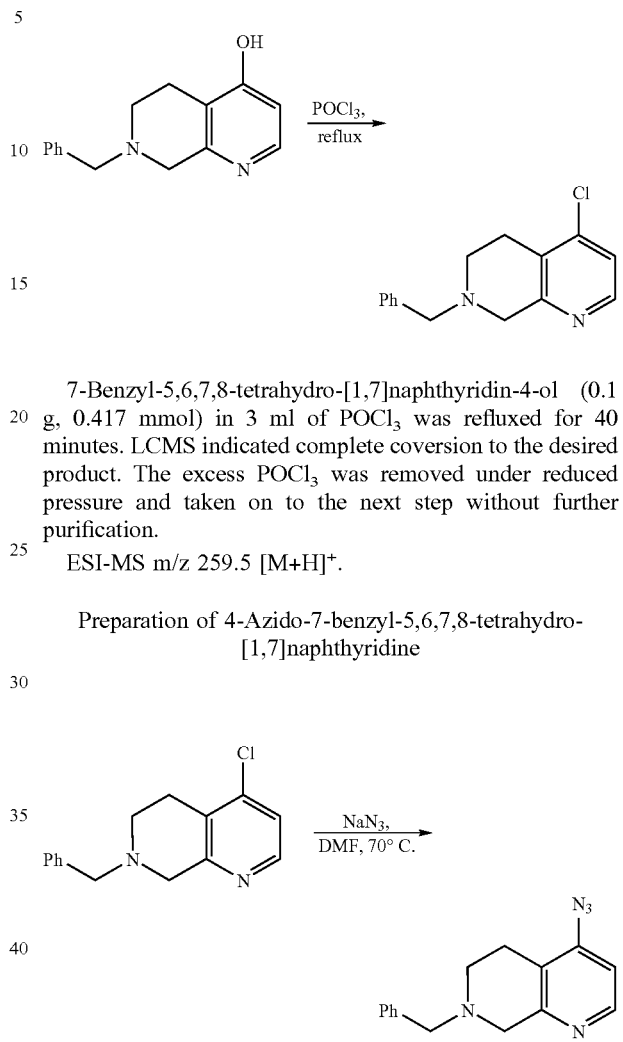

7-Benzyl-5,6,7,8-tetrahydro-[1,7]naphthyridin-4-ol (0.1 g, 0.417 mmol) in 3 ml of POCl$_3$ was refluxed for 40 minutes. LCMS indicated complete coversion to the desired product. The excess POCl$_3$ was removed under reduced pressure and taken on to the next step without further purification.

ESI-MS m/z 259.5 [M+H]$^+$.

Preparation of 4-Azido-7-benzyl-5,6,7,8-tetrahydro-[1,7]naphthyridine

7-Benzyl-4-chloro-5,6,7,8-tetrahydro-[1,7]naphthyridine (0.417 mmol) was treated with 5 equiv. of NaN$_3$ (135 mg) in DMF (0.5 ml) and heated to 70° C. for 4 h. The residue was dissolved on 50 ml of DCM and washed with brine. The organic layer was concentrated to afford a black oil, which was purified by column chromatography to afford the desired azide (61 mg), which was used directly in the next step.

ESI-MS m/z 266.5 [M+H]$^+$.

7-Benzyl-5,6,7,8-tetrahydro-[1,7]naphthyridin-4-ylamine

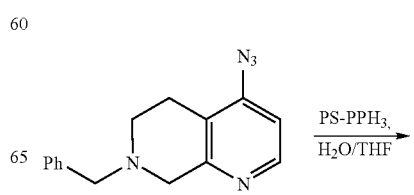

-continued

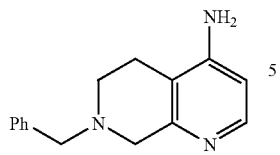

4-azido-7-benzyl-5,6,7,8-tetrahydro-1,7-naphthyridine (0.06 g, 0.226 mmol) was treated with 0.5 g of PS-PPh₃ resin in a 8 ml mixture THF:H2O (18:1) at 32° C. ON. The reaction was monitored by LCMS and TLC. The reaction mixture was filtered and washed with THF and methanol. The combined filtrate was concentrated and used directly in the next step.

ESI-MS m/z 240.3 [M+H]$^+$.

Preparation of 2-Adamantan-1-yl-N-(7-benzyl-5,6,7,8-tetrahydro-[1,7]naphthyridin-4-yl)-acetamide (Compound 342)

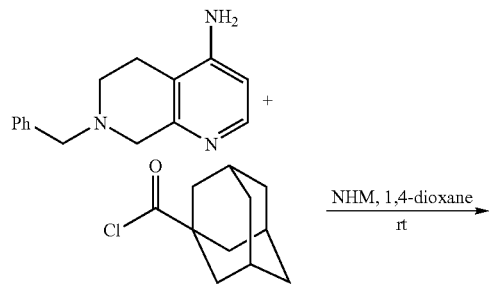

-continued

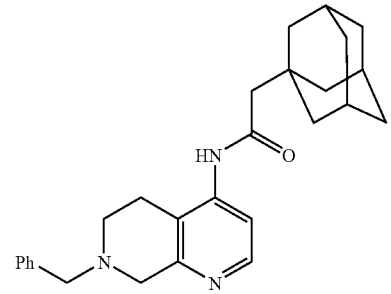

7-Benzyl-5,6,7,8-tetrahydro-[1,7]naphthyridin-4-ylamine (48 mg, 0.202 mmol) in 6 ml of dioxane was treated with NMM (22 μl, 0.202 mmol) followed by adamantan-1-yl-acetyl chloride (0.043 g, 0.202 mmol) and stirred at rt under argon. The reaction was monitored by TLC and LCMS. Excess acid chloride was added and the reaction was stirred. The contents were concentrated and purified by HPLC to afford the desired product (3.3 mg, 4%).

ESI-MS m/z 416.7 [M+H]$^+$.

Exemplary Compounds of the Invention

In addition to the compounds exemplified above, the following compounds recited below in Tables 1A-1E, which comprise various substituted amides of this invention, are prepared or can be prepared using the procedure and synthetic schemes described above, or some modification thereof, and the corresponding starting materials, appropriate reagents, and purification methods known to those skilled in the art. Modifications of the methods described herein are within the scope of the invention and will be obvious to one of skill in the art.

TABLE 1A

Adamantane Substituted Amide Compounds

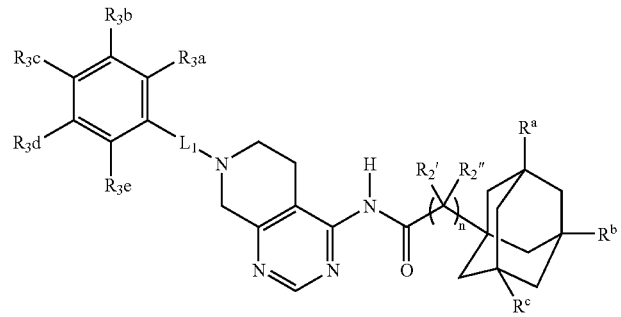

| ID | L$^1$ | R$^{3a}$ | R$^{3b}$ | R$^{3c}$ | R$^{3d}$ | R$^{3e}$ | n | R$^{2\prime}$ | R$^{2\prime\prime}$ | R$^a$ | R$^b$ | R$^c$ |
|---|---|---|---|---|---|---|---|---|---|---|---|---|
| 5  | CH$_2$ | H   | H | H      | H  | H | 1 | H | H | H | H | H |
| 15 | CH$_2$ | H   | H | MeO$_2$S | H  | H | 1 | H | H | H | H | H |
| 27 | CH$_2$ | Cl  | H | H      | H  | H | 1 | H | H | H | H | H |
| 28 | CH$_2$ | F   | H | H      | H  | H | 1 | H | H | H | H | H |
| 29 | CH$_2$ | MeO | H | H      | H  | H | 1 | H | H | H | H | H |
| 30 | CH$_2$ | MeO | H | MeO    | H  | H | 1 | H | H | H | H | H |
| 31 | CH$_2$ | Me  | H | H      | H  | H | 1 | H | H | H | H | H |
| 32 | CH$_2$ | Me  | H | H      | Me | H | 1 | H | H | H | H | H |
| 33 | CH$_2$ | H   | F | H      | H  | H | 1 | H | H | H | H | H |
| 34 | CH$_2$ | H   | Cl| H      | H  | H | 1 | H | H | H | H | H |
| 35 | CH$_2$ | H   | MeO| H     | H  | H | 1 | H | H | H | H | H |

TABLE 1A-continued

Adamantane Substituted Amide Compounds

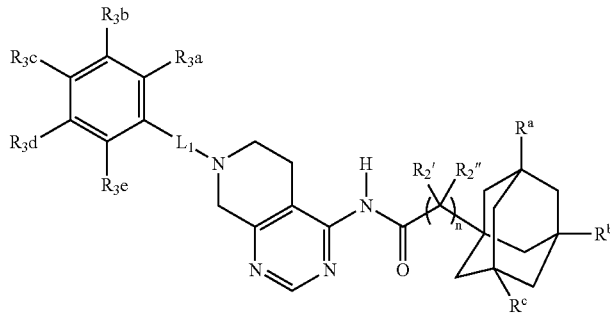

| ID | L¹ | R³ᵃ | R³ᵇ | R³ᶜ | R³ᵈ | R³ᵉ | n | R²' | R²" | Rᵃ | Rᵇ | Rᶜ |
|---|---|---|---|---|---|---|---|---|---|---|---|---|
| 36 | CH₂ | H | MeO | MeO | H | H | 1 | H | H | H | H | H |
| 37 | CH₂ | H | MeO | H | MeO | H | 1 | H | H | H | H | H |
| 38 | CH₂ | H | Me | H | H | H | 1 | H | H | H | H | H |
| 39 | CH₂ | H | Me | MeO | H | H | 1 | H | H | H | H | H |
| 40 | CH₂ | H | H | MeO | H | H | 1 | H | H | H | H | H |
| 41 | CH₂ | H | H | Cl | H | H | 1 | H | H | H | H | H |
| 42 | CH₂ | H | H | CN | H | H | 1 | H | H | H | H | H |
| 44 | CH₂ | H | H | Me | H | H | 1 | H | H | H | H | H |
| 45 | CH₂ | H | H | C₂H₅ | H | H | 1 | H | H | H | H | H |
| 47 | CH₂ | F | H | F | H | H | 1 | H | H | H | H | H |
| 62 | CH₂ | H | H | AcNH | H | H | 1 | H | H | H | H | H |
| 65 | CH₂ | H | H | 2-Pyridyl | H | H | 1 | H | H | H | H | H |
| 68 | CH₂ | H | PhO | H | H | H | 1 | H | H | H | H | H |
| 70 | CH₂ | H | CF₃ | H | H | H | 1 | H | H | H | H | H |
| 71 | CH₂ | H | H | t-Bu | H | H | 1 | H | H | H | H | H |
| 72 | CH₂ | H | H | CF₃ | H | H | 1 | H | H | H | H | H |
| 74 | CH₂ | H | H | CF₃O | H | H | 1 | H | H | H | H | H |
| 75 | CH₂ | H | H | PhO | H | H | 1 | H | H | H | H | H |
| 76 | CH₂ | CF₃O | H | H | H | H | 1 | H | H | H | H | H |
| 77 | CH₂ | OCHF₂ | H | H | H | H | 1 | H | H | H | H | H |
| 78 | CH₂ | H | H | OCHF₂ | H | H | 1 | H | H | H | H | H |
| 84 | CH₂ | H | CN | F | H | H | 1 | H | H | H | H | H |
| 85 | CH₂ | H | F | Me | H | H | 1 | H | H | H | H | H |
| 86 | CH₂ | H | Me | F | H | H | 1 | H | H | H | H | H |
| 87 | CH₂ | F | Me | H | H | Cl | 1 | H | H | H | H | H |
| 88 | CH₂ | Cl | Me | H | H | F | 1 | H | H | H | H | H |
| 89 | CH₂ | H | H | N(Me)—CH₂CH₂OH | H | H | 1 | H | H | H | H | H |
| 91 | CH₂ | H | H | OCH₂CONH₂ | H | H | 1 | H | H | H | H | H |
| 92 | CH₂ | H | H | H | H | C₂H₄NO₂ | 1 | H | H | H | H | H |
| 95 | CH₂ | F | H | MeO | H | H | 1 | H | H | H | H | H |
| 96 | CH₂ | CF₃ | H | H | F | H | 1 | H | H | H | H | H |
| 97 | CH₂ | H | F | CF₃ | H | H | 1 | H | H | H | H | H |
| 98 | CH₂ | H | H | 1-imidazolyl | H | H | 1 | H | H | H | H | H |
| 99 | CH₂ | H | H | OCH₂CH₂OH | H | H | 1 | H | H | H | H | H |
| 100 | CH₂ | OCH₂CH₂OH | H | H | H | H | 1 | H | H | H | H | H |
| 101 | CH₂ | H | OCH₂CH₂OH | H | H | H | 1 | H | H | H | H | H |
| 102 | CH₂ | MeO | H | H | F | H | 1 | H | H | H | H | H |
| 103 | CH₂ | H | MeO | F | H | H | 1 | H | H | H | H | H |
| 104 | CH₂ | F | H | H | MeO | H | 1 | H | H | H | H | H |
| 106 | CH₂ | H | CF₃ | F | H | H | 1 | H | H | H | H | H |
| 107 | CH₂ | CF₃ | H | F | H | H | 1 | H | H | H | H | H |
| 108 | CH₂ | H | CF₃ | H | F | H | 1 | H | H | H | H | H |
| 109 | CH₂ | H | CF₃ | H | H | F | 1 | H | H | H | H | H |
| 110 | CH₂ | F | H | CF₃ | H | H | 1 | H | H | H | H | H |
| 111 | CH₂ | CF₃ | H | H | F | H | 1 | H | H | H | H | H |
| 113 | CH₂ | H | H | O-isoPr | H | H | 1 | H | H | H | H | H |
| 114 | CH₂ | H | CF₃O | H | H | H | 1 | H | H | H | H | H |
| 115 | CH₂ | H | H | CH=CHCO₂H | H | H | 1 | H | H | H | H | H |
| 116 | CH₂ | H | H | MeS | H | H | 1 | H | H | H | H | H |
| 117 | CH₂ | H | MeO | HO | H | H | 1 | H | H | H | H | H |
| 119 | CH₂ | H | F | MeO | H | H | 1 | H | H | H | H | H |
| 120 | CH₂ | CF₃ | H | H | H | H | 1 | H | H | H | H | H |
| 123 | CH₂ | H | H | F | H | H | 1 | H | H | H | H | H |
| 131 | CH₂ | F | CF₃ | H | H | H | 1 | H | H | H | H | H |
| 140 | CH₂ | H | H | OCH₂CO₂H | H | H | 1 | H | H | H | H | H |
| 141 | CH₂ | H | H | H | H | OCH₂CO₂H | 1 | H | H | H | H | H |
| 143 | SO₂ | H | H | H | H | H | 1 | H | H | H | H | H |
| 144 | SO₂ | H | H | Me | H | H | 1 | H | H | H | H | H |
| 149 | SO₂ | H | H | MeO | H | H | 1 | H | H | H | H | H |

TABLE 1A-continued

Adamantane Substituted Amide Compounds

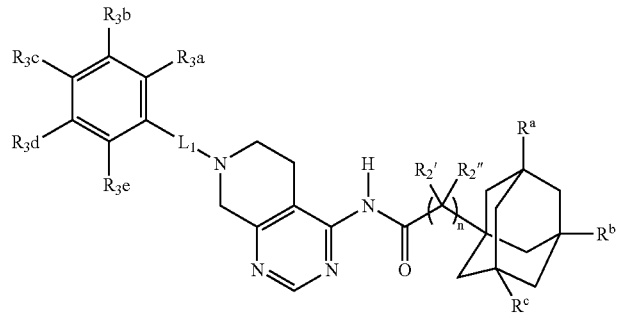

| ID | L¹ | R³ᵃ | R³ᵇ | R³ᶜ | R³ᵈ | R³ᵉ | n | R²' | R²" | Rᵃ | Rᵇ | Rᶜ |
|---|---|---|---|---|---|---|---|---|---|---|---|---|
| 150 | SO₃ | H | H | Cl | H | H | 1 | H | H | H | H | H |
| 151 | SO₂ | H | H | MeO | MeO | H | 1 | H | H | H | H | H |
| 152 | SO₂ | H | H | F | H | H | 1 | H | H | H | H | H |
| 154 | SO₂ | H | H | H | CF₃ | H | 1 | H | H | H | H | H |
| 155 | SO₂ | H | H | Cl | Cl | H | 1 | H | H | H | H | H |
| 156 | SO₂ | H | H | CF₃O | H | H | 1 | H | H | H | H | H |
| 161 | SO₂ | H | H | H | CF₃O | H | 1 | H | H | H | H | H |
| 162 | SO₂ | H | H | H | MeO | H | 1 | H | H | H | H | H |
| 165 | SO₂ | H | H | CN | H | Cl | 1 | H | H | H | H | H |
| 166 | SO₂ | H | H | H | H | F | 1 | H | H | H | H | H |
| 167 | SO₂ | H | H | CN | H | H | 1 | H | H | H | H | H |
| 168 | SO₂ | H | H | H | Cl | H | 1 | H | H | H | H | H |
| 172 | SO₂ | H | H | O-2-pyridyl | H | H | 1 | H | H | H | H | H |
| 173 | SO₂ | H | H | O-3-pyridyl | H | H | 1 | H | H | H | H | H |
| 174 | SO₂ | H | H | O-3-pyridyl | H | H | 1 | H | H | H | H | H |
| 175 | SO₂ | H | H | O-(4-MeOPh) | H | H | 1 | H | H | H | H | H |
| 176 | SO₂ | H | H | O-(3,4-di Cl Ph) | H | H | 1 | H | H | H | H | H |
| 177 | SO₂ | H | H | O-(4-CF₃Ph) | H | H | 1 | H | H | H | H | H |
| 178 | SO₂ | H | H | H | (3,4-di Cl Ph)O | H | 1 | H | H | H | H | H |
| 179 | SO₂ | H | H | 4-MeOPh | H | H | 1 | H | H | H | H | H |
| 181 | SO₂ | Cl | H | H | CF₃ | H | 1 | H | H | H | H | H |
| 190 | SO₂ | H | H | OCHF₂ | H | H | 1 | H | H | H | H | H |
| 191 | SO₂ | H | H | PhO | H | H | 1 | H | H | H | H | H |
| 192 | SO₂ | H | H | H | H | Cl | 1 | H | H | H | H | H |
| 193 | SO₂ | H | H | F | Cl | H | 1 | H | H | H | H | H |
| 194 | SO₂ | H | H | H | H | C₆H₅ | 1 | H | H | H | H | H |
| 195 | SO₂ | H | H | H | H | CF₃ | 1 | H | H | H | H | H |
| 196 | SO₂ | H | H | 1-pyrazolyl | H | H | 1 | H | H | H | H | H |
| 197 | SO₂ | H | H | MeO | H | MeO | 1 | H | H | H | H | H |
| 199 | SO₂ | H | H | H | H | Me | 1 | H | H | H | H | H |
| 201 | SO₂ | H | H | CF₃ | H | H | 1 | H | H | H | H | H |
| 202 | SO₂ | H | H | Cl | H | F | 1 | H | H | H | H | H |
| 203 | SO₂ | F | H | H | F | H | 1 | H | H | H | H | H |
| 204 | SO₂ | Cl | H | H | Cl | H | 1 | H | H | H | H | H |
| 205 | SO₂ | F | H | H | Cl | H | 1 | H | H | H | H | H |
| 206 | SO₂ | F | H | H | H | F | 1 | H | H | H | H | H |
| 207 | SO₂ | H | H | Me | Cl | H | 1 | H | H | H | H | H |
| 208 | SO₂ | H | Cl | H | Cl | H | 1 | H | H | H | H | H |
| 209 | SO₂ | H | H | F | H | F | 1 | H | H | H | H | H |
| 210 | SO₂ | Cl | H | H | H | Cl | 1 | H | H | H | H | H |
| 211 | SO₂ | H | H | F | H | Cl | 1 | H | H | H | H | H |
| 212 | SO₂ | Me | H | H | F | H | 1 | H | H | H | H | H |
| 214 | SO₂ | H | Me | H | H | MeO | 1 | H | H | H | H | H |
| 215 | SO₂ | H | H | H | F | H | 1 | H | H | H | H | H |
| 216 | SO₂ | MeO | H | H | MeO | H | 1 | H | H | H | H | H |
| 217 | SO₂ | H | Me | H | Me | H | 1 | H | H | H | H | H |
| 218 | CO | Cl | H | H | H | Cl | 1 | H | H | H | H | H |
| 220 | CO | H | H | H | H | H | 1 | H | H | H | H | H |
| 221 | CO | H | H | C₆H₅ | H | H | 1 | H | H | H | H | H |
| 226 | CO | H | H | Cl | H | H | 1 | H | H | H | H | H |
| 227 | CO | H | F | H | H | H | 1 | H | H | H | H | H |
| 228 | CO | H | H | CF₃O | H | H | 1 | H | H | H | H | H |
| 229 | CO | H | H | C₂H₅ | H | H | 1 | H | H | H | H | H |
| 230 | CO | H | Me | H | H | H | 1 | H | H | H | H | H |
| 232 | CO | H | F | F | H | H | 1 | H | H | H | H | H |
| 233 | CO | H | CF₃ | H | H | H | 1 | H | H | H | H | H |
| 234 | CO | H | H | MeO | H | H | 1 | H | H | H | H | H |
| 242 | CO | H | CN | H | H | H | 1 | H | H | H | H | H |
| 243 | CO | H | H | CF₃ | H | H | 1 | H | H | H | H | H |

TABLE 1A-continued

Adamantane Substituted Amide Compounds

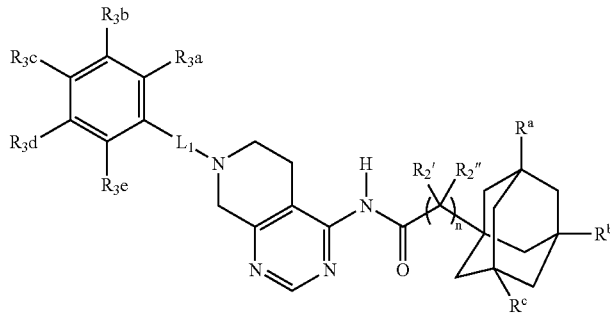

| ID | L¹ | R³ᵃ | R³ᵇ | R³ᶜ | R³ᵈ | R³ᵉ | n | R²' | R²" | Rᵃ | Rᵇ | Rᶜ |
|---|---|---|---|---|---|---|---|---|---|---|---|---|
| 245 | CO | H | Cl | Cl | H | H | 1 | H | H | H | H | H |
| 246 | CO | H | MeO | H | MeO | H | 1 | H | H | H | H | H |
| 247 | CO | F | H | H | H | F | 1 | H | H | H | H | H |
| 250 | CO | H | MeO | H | H | H | 1 | H | H | H | H | H |
| 251 | CO | H | H | F | H | H | 1 | H | H | H | H | H |
| 253 | CO | H | Cl | H | H | H | 1 | H | H | H | H | H |
| 257 | CO | H | H | CN | H | H | 1 | H | H | H | H | H |
| 258 | CO | Cl | H | Cl | H | H | 1 | H | H | H | H | H |
| 266 | CO | F | H | CF₃ | H | H | 1 | H | H | H | H | H |
| 267 | CO | H | CF₃ | H | F | H | 1 | H | H | H | H | H |
| 268 | CO | CF₃O | H | H | H | H | 1 | H | H | H | H | H |
| 269 | CO | H | CF₃O | H | H | H | 1 | H | H | H | H | H |
| 270 | CO | CF₃ | H | H | H | H | 1 | H | H | H | H | H |
| 271 | CO | H | CF₃ | H | H | Cl | 1 | H | H | H | H | H |
| 272 | CO | F | H | H | H | Cl | 1 | H | H | H | H | H |
| 275 | CO | MeO | H | MeO | H | H | 1 | H | H | H | H | H |
| 277 | CO | F | H | F | H | H | 1 | H | H | H | H | H |
| 278 | CO | Me | H | H | H | H | 1 | H | H | H | H | H |
| 279 | CO | F | H | H | F | H | 1 | H | H | H | H | H |
| 280 | CO | F | H | H | H | H | 1 | H | H | H | H | H |
| 282 | CO | Cl | Cl | H | H | H | 1 | H | H | H | H | H |
| 291 | CO | H | H | Me | H | H | 1 | H | H | H | H | H |
| 292 | CO | MeO | H | H | H | H | 1 | H | H | H | H | H |
| 294 | CO | Cl | H | H | H | H | 1 | H | H | H | H | H |
| 301 | CO | H | H | t-Bu | H | H | 1 | H | H | H | H | H |
| 310 | CO | H | F | MeO | H | H | 1 | H | H | H | H | H |
| 312 | CO | H | MeO | MeO | H | H | 1 | H | H | H | H | H |
| 314 | CO | Cl | H | H | F | H | 1 | H | H | H | H | H |
| 315 | CO | H | Cl | H | Cl | H | 1 | H | H | H | H | H |
| 319 | CH₂ | H | H | Cl | H | Cl | 1 | H | H | H | H | H |
| 320 | CH₂ | H | H | Me | H | Me | 1 | H | H | H | H | H |
| 322 | CH₂ | H | H | F | F | H | 1 | H | H | H | H | H |
| 323 | CH₂ | H | H | F | Cl | H | 1 | H | H | H | H | H |
| 324 | CH₂ | H | H | MeO | Cl | H | 1 | H | H | H | H | H |
| 325 | CH₂ | H | H | Cl | CF₃ | H | 1 | H | H | H | H | H |
| 326 | CH₂ | H | H | F | H | Cl | 1 | H | H | H | H | H |
| 327 | CH₂ | H | H | CF₃ | H | CF₃ | 1 | H | H | H | H | H |
| 328 | CH₂ | H | H | Cl | H | F | 1 | H | H | H | H | H |
| 329 | CH₂ | H | H | Cl | F | H | 1 | H | H | H | H | H |
| 330 | CH₂ | H | H | OCH₂Ph | H | MeO | 1 | H | H | H | H | H |
| 331 | CH₂ | H | H | OCH₂CH₂CO₂H | H | MeO | 1 | H | H | H | H | H |
| 334 | CH₂ | H | H | H | H | H | 0 | — | — | H | H | H |
| 339 | CH₂ | H | H | H | H | H | 1 | Me | Me | H | H | H |
| 341 | CH₂ | H | H | H | H | H | 1 | H | H | Me | Me | H |
| 343 | CH₂ | H | H | H | H | H | 1 | Me | Me | Me | Me | H |
| 344 | CH₂ | H | H | H | H | H | 1 | H | H | Me | Me | Me |
| 345 | CH₂ | H | H | H | H | H | 1 | Me | Me | Me | Me | Me |
| 346 | CH₂ | H | H | H | H | H | 0 | — | — | Me | Me | Me |
| 347 | CH₂ | F | H | F | H | H | 1 | Me | Me | H | H | H |
| 348 | CH₂ | Cl | H | H | H | H | 1 | Me | Me | H | H | H |
| 349 | CH₂ | Me | H | H | H | H | 1 | Me | Me | H | H | H |
| 352 | CH₂ | H | H | F | H | H | 1 | Me | Me | H | H | H |
| 354 | SO₂ | H | Cl | H | H | H | 1 | Me | Me | H | H | H |
| 355 | SO₂ | H | H | F | F | H | 1 | Me | Me | H | H | H |
| 358 | CO | H | Me | H | H | H | 1 | Me | Me | H | H | H |
| 359 | CO | H | H | H | CF₃ | H | 1 | Me | Me | H | H | H |
| 360 | CO | H | H | Cl | Cl | H | 1 | Me | Me | H | H | H |
| 361 | CO | F | H | H | H | F | 1 | Me | Me | H | H | H |
| 362 | CO | F | H | H | H | Cl | 1 | Me | Me | H | H | H |

TABLE 1A-continued

Adamantane Substituted Amide Compounds

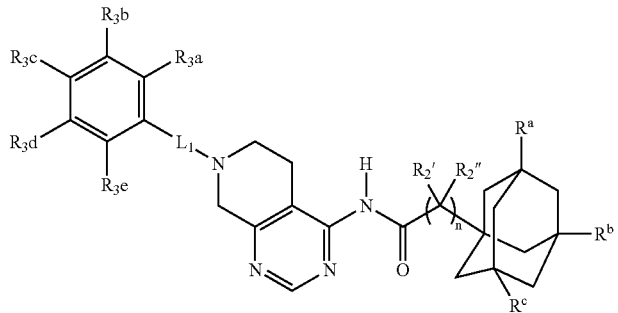

| ID | L¹ | R³ᵃ | R³ᵇ | R³ᶜ | R³ᵈ | R³ᵉ | n | R²' | R²'' | Rᵃ | Rᵇ | Rᶜ |
|---|---|---|---|---|---|---|---|---|---|---|---|---|
| 363 | CO | F | H | H | F | H | 1 | Me | Me | H | H | H |
| 364 | CO | Cl | Cl | H | H | H | 1 | Me | Me | H | H | H |
| 369 | CH₂ | F | H | H | H | H | 1 | Me | Me | H | H | H |
| 370 | CH₂ | H | H | H | H | Cl | 1 | H | H | H | Me | Me |
| 371 | CH₂ | H | H | H | H | F | 1 | H | H | H | Me | Me |
| 372 | CH₂ | H | H | H | H | Me | 1 | H | H | H | Me | Me |
| 374 | CH₂ | H | H | F | H | F | 1 | H | H | H | Me | Me |
| 376 | CH₂ | H | H | F | H | H | 1 | H | H | H | Me | Me |
| 380 | SO₂ | H | H | H | Cl | H | 1 | H | H | H | Me | Me |
| 381 | SO₂ | H | H | H | F | F | 1 | H | H | H | Me | Me |
| 382 | CO | H | H | H | Me | H | 1 | H | H | Me | H | Me |
| 383 | CO | H | CF₃ | H | H | H | 1 | H | H | Me | H | Me |
| 385 | CO | H | Cl | Cl | H | H | 1 | H | H | Me | H | Me |
| 387 | CO | F | H | H | H | F | 1 | H | H | Me | H | Me |
| 389 | CO | F | H | H | H | Cl | 1 | H | H | Me | H | Me |
| 390 | CO | F | H | H | F | H | 1 | H | H | Me | H | Me |
| 391 | CO | Cl | Cl | H | H | H | 1 | H | H | Me | H | Me |
| 392 | CO | Cl | H | H | H | Cl | 0 | — | — | H | H | H |
| 394 | CO | H | H | H | H | H | 0 | — | — | H | H | H |
| 399 | CO | H | H | Cl | H | H | 0 | — | — | H | H | H |
| 400 | CO | H | H | H | F | H | 0 | — | — | H | H | H |
| 401 | CO | H | H | CF₃O | H | H | 0 | — | — | H | H | H |
| 402 | CO | H | H | C₂H₅ | H | H | 0 | — | — | H | H | H |
| 403 | CO | H | H | H | Me | H | 0 | — | — | H | H | H |
| 405 | CO | H | H | F | F | H | 0 | — | — | H | H | H |
| 406 | CO | H | H | H | CF₃ | H | 0 | — | — | H | H | H |
| 407 | CO | H | H | MeO | H | H | 0 | — | — | H | H | H |
| 414 | CO | H | H | H | CN | H | 0 | — | — | H | H | H |
| 415 | CO | H | H | CF₃ | H | H | 0 | — | — | H | H | H |
| 417 | CO | H | H | Cl | Cl | H | 0 | — | — | H | H | H |
| 418 | CO | H | MeO | H | MeO | H | 0 | — | — | H | H | H |
| 419 | CO | F | H | H | H | F | 0 | — | — | H | H | H |
| 422 | CO | H | H | H | MeO | H | 0 | — | — | H | H | H |
| 423 | CO | H | H | F | H | H | 0 | — | — | H | H | H |
| 425 | CO | H | H | H | Cl | H | 0 | — | — | H | H | H |
| 429 | CO | H | H | CN | H | H | 0 | — | — | H | H | H |
| 430 | CO | H | H | Cl | H | Cl | 0 | — | — | H | H | H |
| 438 | CO | H | H | H | CF₃ | F | 0 | — | — | H | H | H |
| 439 | CO | H | F | H | CF₃ | H | 0 | — | — | H | H | H |
| 440 | CO | H | H | H | H | CF₃O | 0 | — | — | H | H | H |
| 441 | CO | H | H | H | CF₃O | H | 0 | — | — | H | H | H |
| 442 | CO | H | H | H | H | CF₃ | 0 | — | — | H | H | H |
| 443 | CO | Cl | H | H | CF₃ | H | 0 | — | — | H | H | H |
| 444 | CO | Cl | H | H | H | F | 0 | — | — | H | H | H |
| 447 | CO | H | H | MeO | H | MeO | 0 | — | — | H | H | H |
| 449 | CO | H | H | F | H | F | 0 | — | — | H | H | H |
| 450 | CO | H | H | H | H | Me | 0 | — | — | H | H | H |
| 451 | CO | H | F | H | H | F | 0 | — | — | H | H | H |
| 452 | CO | H | H | H | H | F | 0 | — | — | H | H | H |
| 454 | CO | H | H | H | Cl | Cl | 0 | — | — | H | H | H |
| 461 | CO | H | H | Me | H | H | 0 | — | — | H | H | H |
| 462 | CO | H | H | H | H | MeO | 0 | — | — | H | H | H |
| 464 | CO | H | H | H | H | Cl | 0 | — | — | H | H | H |
| 469 | CO | H | H | t-Bu | H | H | 0 | — | — | H | H | H |
| 475 | CO | H | H | MeO | F | H | 0 | — | — | H | H | H |
| 476 | CO | H | H | MeO | MeO | H | 0 | — | — | H | H | H |
| 478 | CO | H | F | H | H | Cl | 0 | — | — | H | H | H |
| 479 | CO | H | Cl | H | Cl | H | 0 | — | — | H | H | H |
| 481 | SO₂ | H | H | H | H | H | 0 | — | — | H | H | H |

TABLE 1A-continued

Adamantane Substituted Amide Compounds

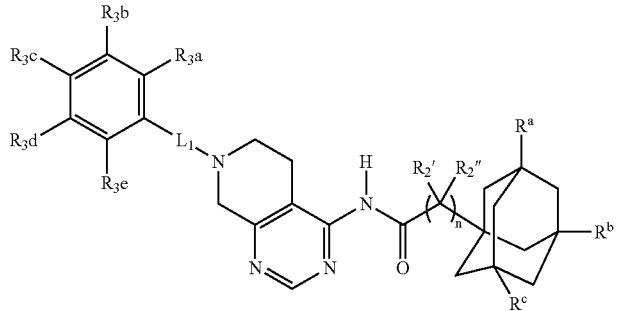

| ID | L¹ | R$^{3a}$ | R$^{3b}$ | R$^{3c}$ | R$^{3d}$ | R$^{3e}$ | n | R$^{2'}$ | R$^{2''}$ | R$^a$ | R$^b$ | R$^c$ |
|---|---|---|---|---|---|---|---|---|---|---|---|---|
| 482 | SO$_2$ | H | H | Me | H | H | 0 | — | — | H | H | H |
| 487 | SO$_2$ | H | H | MeO | H | H | 0 | — | — | H | H | H |
| 488 | SO$_2$ | H | H | Cl | H | H | 0 | — | — | H | H | H |
| 489 | SO$_2$ | H | MeO | MeO | H | H | 0 | — | — | H | H | H |
| 490 | SO$_2$ | H | H | F | H | H | 0 | — | — | H | H | H |
| 492 | SO$_2$ | H | CF$_3$ | H | H | H | 0 | — | — | H | H | H |
| 493 | SO$_2$ | H | H | CF$_3$O | H | H | 0 | — | — | H | H | H |
| 497 | SO$_2$ | H | CF$_3$O | H | H | H | 0 | — | — | H | H | H |
| 498 | SO$_2$ | H | MeO | H | H | H | 0 | — | — | H | H | H |
| 500 | SO$_2$ | Cl | H | CN | H | H | 0 | — | — | H | H | H |
| 501 | SO$_2$ | F | H | H | H | H | 0 | — | — | H | H | H |
| 502 | SO$_2$ | H | H | CN | H | H | 0 | — | — | H | H | H |
| 506 | SO$_2$ | H | H | O-2-pyridyl | H | H | 0 | — | — | H | H | H |
| 507 | SO$_2$ | H | H | O-3-pyridyl | H | H | 0 | — | — | H | H | H |
| 508 | SO$_2$ | H | H | O-4-pyridyl | H | H | 0 | — | — | H | H | H |
| 509 | SO$_2$ | H | H | O-(4-MeOPh) | H | H | 0 | — | — | H | H | H |
| 510 | SO$_2$ | H | H | O-(4-CF3Ph) | H | H | 0 | — | — | H | H | H |
| 511 | SO$_2$ | H | O-(3,4-di Cl Ph) | H | H | H | 0 | — | — | H | H | H |
| 512 | SO$_2$ | H | H | 4-MeOPh | H | H | 0 | — | — | H | H | H |
| 514 | SO$_2$ | H | CF$_3$ | H | H | Cl | 0 | — | — | H | H | H |
| 523 | SO$_2$ | H | H | CHF$_2$O | H | H | 0 | — | — | H | H | H |
| 524 | SO$_2$ | H | H | C$_6$H$_5$O | H | H | 0 | — | — | H | H | H |
| 525 | SO$_2$ | Cl | H | H | H | H | 0 | — | — | H | H | H |
| 526 | SO$_2$ | H | Cl | F | H | H | 0 | — | — | H | H | H |
| 527 | SO$_2$ | C$_6$H$_5$ | H | H | H | H | 0 | — | — | H | H | H |
| 528 | SO$_2$ | CF$_3$ | H | H | H | H | 0 | — | — | H | H | H |
| 529 | SO$_2$ | H | H | 1-pyrazolyl | H | H | 0 | — | — | H | H | H |
| 530 | SO$_2$ | MeO | H | MeO | H | H | 0 | — | — | H | H | H |
| 532 | SO$_2$ | CF$_3$O | H | H | H | H | 0 | — | — | H | H | H |
| 533 | SO$_2$ | Me | H | H | H | H | 0 | — | — | H | H | H |
| 535 | SO$_2$ | H | H | CF$_3$ | H | H | 0 | — | — | H | H | H |
| 536 | SO$_2$ | F | H | Cl | H | H | 0 | — | — | H | H | H |
| 537 | SO$_2$ | H | F | H | H | F | 0 | — | — | H | H | H |
| 538 | SO$_2$ | H | Cl | H | H | Cl | 0 | — | — | H | H | H |
| 539 | SO$_2$ | H | Cl | H | H | F | 0 | — | — | H | H | H |
| 540 | SO$_2$ | F | H | H | H | F | 0 | — | — | H | H | H |
| 541 | SO$_2$ | H | Cl | Me | H | H | 0 | — | — | H | H | H |
| 542 | SO$_2$ | H | Cl | H | Cl | H | 0 | — | — | H | H | H |
| 543 | SO$_2$ | F | H | F | H | H | 0 | — | — | H | H | H |
| 544 | SO$_2$ | Cl | H | H | H | Cl | 0 | — | — | H | H | H |
| 545 | SO$_2$ | Cl | H | F | H | H | 0 | — | — | H | H | H |
| 546 | SO$_2$ | H | F | H | H | Me | 0 | — | — | H | H | H |
| 548 | SO$_2$ | MeO | H | H | Me | H | 0 | — | — | H | H | H |
| 549 | SO$_2$ | H | MeO | H | H | MeO | 0 | — | — | H | H | H |
| 550 | SO$_2$ | H | Me | H | Me | H | 0 | — | — | H | H | H |
| 551 | SO$_2$ | CN | H | H | H | H | 0 | — | — | H | H | H |
| 562 | CH$_2$ | H | H | MeO | H | H | 0 | — | — | H | H | H |
| 566 | CH$_2$ | H | H | MeO | MeO | H | 0 | — | — | H | H | H |
| 568 | CH$_2$ | H | H | H | C$_6$H$_5$O | H | 0 | — | — | H | H | H |
| 569 | CH$_2$ | H | Br | H | H | MeO | 0 | — | — | H | H | H |
| 570 | CH$_2$ | H | H | Cl | H | Cl | 0 | — | — | H | H | H |
| 571 | CH$_2$ | H | H | H | CN | H | 0 | — | — | H | H | H |
| 572 | CH$_2$ | H | H | t-Bu | H | H | 0 | — | — | H | H | H |
| 574 | CH$_2$ | H | H | H | CF$_3$ | H | 0 | — | — | H | H | H |
| 575 | CH$_2$ | H | H | NMe$_2$ | H | H | 0 | — | — | H | H | H |
| 576 | CH$_2$ | H | H | C$_6$H$_5$O | H | H | 0 | — | — | H | H | H |
| 577 | CH$_2$ | Cl | H | H | H | F | 0 | — | — | H | H | H |
| 584 | CH$_2$ | H | H | H | MeO | H | 0 | — | — | H | H | H |
| 585 | CH$_2$ | H | H | Me | Me | H | 0 | — | — | H | H | H |

TABLE 1A-continued

Adamantane Substituted Amide Compounds

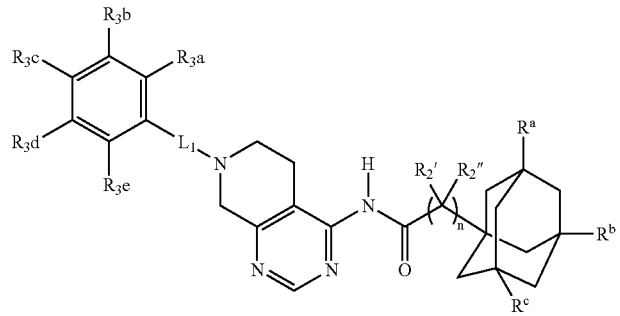

| ID | L¹ | R$^{3a}$ | R$^{3b}$ | R$^{3c}$ | R$^{3d}$ | R$^{3e}$ | n | R$^{2'}$ | R$^{2''}$ | R$^a$ | R$^b$ | R$^c$ |
|---|---|---|---|---|---|---|---|---|---|---|---|---|
| 586 | CH$_2$ | H | H | MeO | MeO | Cl | 0 | — | — | H | H | H |
| 588 | CH$_2$ | H | H | OCH$_2$Ph | MeO | H | 0 | — | — | H | H | H |
| 590 | CH$_2$ | H | H | Cl | Cl | H | 0 | — | — | H | H | H |
| 591 | CH$_2$ | H | H | H | MeO | MeO | 0 | — | — | H | H | H |
| 592 | CH$_2$ | H | H | MeO | OCH$_2$Ph | H | 0 | — | — | H | H | H |
| 593 | CH$_2$ | H | H | MeO | HO | H | 0 | — | — | H | H | H |
| 594 | CH$_2$ | H | MeO | MeO | Br | H | 0 | — | — | H | H | H |
| 595 | CH$_2$ | H | H | F | CN | H | 0 | — | — | H | H | H |
| 597 | CH$_2$ | H | H | Br | H | H | 0 | — | — | H | H | H |
| 598 | CH$_2$ | H | H | H | Cl | H | 0 | — | — | H | H | H |
| 601 | CH$_2$ | H | H | Cl | H | H | 0 | — | — | H | H | H |
| 602 | CH$_2$ | H | H | Me | H | H | 0 | — | — | H | H | H |
| 603 | CH$_2$ | H | H | CN | H | H | 0 | — | — | H | H | H |
| 604 | CH$_2$ | H | H | CF$_3$ | H | H | 0 | — | — | H | H | H |
| 605 | CH$_2$ | H | H | H | F | H | 0 | — | — | H | H | H |
| 606 | CH$_2$ | H | H | H | Me | H | 0 | — | — | H | H | H |
| 607 | CH$_2$ | H | H | F | H | H | 0 | — | — | H | H | H |
| 608 | CH$_2$ | H | H | MeO | H | MeO | 0 | — | — | H | H | H |
| 609 | CH$_2$ | H | H | F | H | F | 0 | — | — | H | H | H |
| 611 | CH$_2$ | H | H | Cl | F | H | 0 | — | — | H | H | H |
| 612 | CH$_2$ | H | H | CF$_3$ | H | F | 0 | — | — | H | H | H |
| 614 | CH$_2$ | H | H | H | Br | H | 0 | — | — | H | H | H |
| 615 | CH$_2$ | H | H | H | H | MeO | 0 | — | — | H | H | H |
| 616 | CH$_2$ | H | H | NHAc | H | H | 0 | — | — | H | H | H |
| 617 | CH$_2$ | H | H | H | H | Br | 0 | — | — | H | H | H |
| 618 | CH$_2$ | H | Br | H | H | F | 0 | — | — | H | H | H |
| 620 | CH$_2$ | H | H | CF$_3$O | H | H | 0 | — | — | H | H | H |
| 621 | CH$_2$ | H | H | CHF$_2$O | H | H | 0 | — | — | H | H | H |
| 622 | CH$_2$ | H | H | OCH$_2$-(4-F-Ph) | H | H | 0 | — | — | H | H | H |
| 623 | CH$_2$ | H | MeO | MeO | H | F | 0 | — | — | H | H | H |
| 624 | CH$_2$ | F | H | MeO | H | F | 0 | — | — | H | H | H |
| 625 | CH$_2$ | H | H | H | C$_2$H$_5$O | H | 0 | — | — | H | H | H |
| 626 | CH$_2$ | H | H | H | (3-CF3Ph)O | H | 0 | — | — | H | H | H |
| 628 | CH$_2$ | H | MeO | H | H | F | 0 | — | — | H | H | H |
| 629 | CH$_2$ | H | H | F | MeO | H | 0 | — | — | H | H | H |
| 630 | CH$_2$ | H | H | C$_2$H$_5$O | H | H | 0 | — | — | H | H | H |
| 631 | CH$_2$ | H | MeO | H | H | MeO | 0 | — | — | H | H | H |
| 632 | CH$_2$ | H | H | H | CF$_3$O | H | 0 | — | — | H | H | H |
| 633 | CH$_2$ | H | MeO | H | MeO | H | 0 | — | — | H | H | H |
| 635 | CH$_2$ | H | H | Cl | H | F | 0 | — | — | H | H | H |

TABLE 1B

Adamantane Substituted Amide Compounds

| ID | L¹—R³ | n | R²' | R²" | Rᵃ | Rᵇ | Rᶜ |
|---|---|---|---|---|---|---|---|
| 6 | H | 1 | H | H | H | H | H |
| 7 | methyl | 1 | H | H | H | H | H |
| 8 | ethyl | 1 | H | H | H | H | H |
| 13 | 2-hydroxy-3-methoxy-propyl | 1 | H | H | H | H | H |
| 14 | phenethyl | 1 | H | H | H | H | H |
| 16 | 3-pyridylmethyl | 1 | H | H | H | H | H |
| 18 | 2-hydroxyethyl | 1 | H | H | H | H | H |
| 19 | 3-hydroxypropyl | 1 | H | H | H | H | H |
| 23 | 2,3-dihydroxypropyl | 1 | H | H | H | H | H |
| 43 | 4-pyridylmethyl | 1 | H | H | H | H | H |
| 46 | 2,5-dioxabicyclo[4.4.0deca-6,8,10-trien-9-ylmethyl | 1 | H | H | H | H | H |
| 61 | 2-pyridylmethyl | 1 | H | H | H | H | H |
| 63 | 3-phenylpropyl | 1 | H | H | H | H | H |
| 64 | 1H-indol-5-ylmethyl | 1 | H | H | H | H | H |
| 66 | [(5-methyl-2-thienyl)methyl | 1 | H | H | H | H | H |
| 67 | (1-methylimidazol-2-yl)methyl | 1 | H | H | H | H | H |
| 69 | 4-quinolylmethyl | 1 | H | H | H | H | H |
| 73 | 2-quinolylmethyl | 1 | H | H | H | H | H |
| 79 | (5-phenyl-2-thienyl)methyl | 1 | H | H | H | H | H |
| 80 | (2-butyl-1H-imidazol-4-yl)methyl | 1 | H | H | H | H | H |
| 81 | (5-methyl-3H-imidazol-4-yl)methyl | 1 | H | H | H | H | H |
| 82 | 1H-imidazol-4-ylmethyl | 1 | H | H | H | H | H |
| 83 | (5-chloro-2-thienyl)methyl | 1 | H | H | H | H | H |
| 90 | (2,2-difluorobenzo[1,3dioxol-4-yl)methyl | 1 | H | H | H | H | H |
| 105 | 2,3-dihydrobenzofuran-5-ylmethyl | 1 | H | H | H | H | H |
| 112 | (4-methyl-1-naphthyl)methyl | 1 | H | H | H | H | H |
| 118 | (6-methyl-2-pyridyl)methyl | 1 | H | H | H | H | H |
| 121 | cyclopentylmethyl | 1 | H | H | H | H | H |
| 122 | cyclohexylmethyl | 1 | H | H | H | H | H |
| 142 | methylsulfonyl | 1 | H | H | H | H | H |
| 145 | 2-naphthylsulfonyl | 1 | H | H | H | H | H |
| 146 | 8-quinolylsulfonyl | 1 | H | H | H | H | H |
| 147 | propylsulfonyl | 1 | H | H | H | H | H |
| 148 | ethylsulfonyl | 1 | H | H | H | H | H |
| 153 | benzylsulfonyl | 1 | H | H | H | H | H |
| 157 | (5-methyl-2-oxa-5-azabicyclo[4.4.0deca-7,9,11-trien-9-yl)sulfonyl | 1 | H | H | H | H | H |
| 158 | 5-chloro-1,3-dimethyl-pyrazol-4-yl)sulfonyl | 1 | H | H | H | H | H |
| 159 | [5-methyl-2-(trifluoromethyl)-3-furylsulfonyl | 1 | H | H | H | H | H |
| 160 | 5-methyl-1-phenyl-pyrazol-4-yl)sulfonyl | 1 | H | H | H | H | H |
| 163 |  | 1 | H | H | H | H | H |
| 164 | 1,2-dimethylimidazol-4-yl)sulfonyl | 1 | H | H | H | H | H |
| 169 | 3,5-dimethylisoxazol-4-yl)sulfonyl | 1 | H | H | H | H | H |
| 170 | methylsulfonylmethylsulfonyl | 1 | H | H | H | H | H |
| 171 | (2-oxochromen-6-yl)sulfonyl | 1 | H | H | H | H | H |
| 180 | 3-pyridylsulfonyl | 1 | H | H | H | H | H |
| 182 | [3,5-bis(trifluoromethyl)phenylmethylsulfonyl | 1 | H | H | H | H | H |
| 183 | [4-(trifluoromethyl)phenylmethylsulfonyl | 1 | H | H | H | H | H |
| 184 | (4-fluorophenyl)methylsulfonyl | 1 | H | H | H | H | H |
| 185 | (3,4-dichlorophenyl)methylsulfonyl | 1 | H | H | H | H | H |
| 186 | (3,5-dichlorophenyl)methylsulfonyl | 1 | H | H | H | H | H |
| 187 | [3-(trifluoromethyl)phenylmethylsulfonyl | 1 | H | H | H | H | H |
| 188 |  | 1 | H | H | H | H | H |
| 189 | (4-chlorophenyl)methylsulfonyl | 1 | H | H | H | H | H |
| 198 | 1,3,5-trimethylpyrazol-4-yl)sulfonyl | 1 | H | H | H | H | H |
| 200 | 2,5-dioxabicyclo[4.4.0deca-7,9,11-trien-9-ylsulfonyl) | 1 | H | H | H | H | H |
| 213 | isopropylsulfonyl | 1 | H | H | H | H | H |
| 219 | acetyl | I | H | H | H | H | H |
| 222 | 2-chloropyridine-3-carbonyl | 1 | H | H | H | H | H |
| 223 | propanoyl | 1 | H | H | H | H | H |
| 224 | 2-(4-methoxyphenyl)acetyl | 1 | H | H | H | H | H |
| 225 | 2-phenylacetyl | 1 | H | H | H | H | H |

TABLE 1B-continued

Adamantane Substituted Amide Compounds

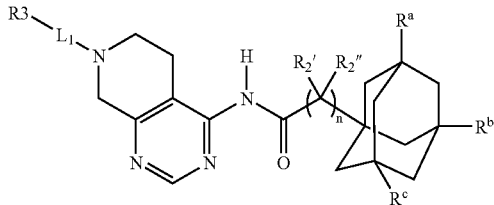

| ID | L¹—R³ | n | R²' | R²" | Rᵃ | Rᵇ | Rᶜ |
|---|---|---|---|---|---|---|---|
| 231 | 3-cyclopentylpropanoyl | 1 | H | H | H | H | H |
| 235 | 3,5,5-trimethylhexanoyl | 1 | H | H | H | H | H |
| 236 | 2,2-diphenylacetyl | 1 | H | H | H | H | H |
| 237 | pyridine-3-carbonyl | 1 | H | H | H | H | H |
| 238 | cyclopentanecarbonyl | 1 | H | H | H | H | H |
| 239 | 2-(2,5-dimethoxyphenyl)acetyl | 1 | H | H | H | H | H |
| 240 | 2-methoxyacetyl | 1 | H | H | H | H | H |
| 241 | 2-(4-fluorophenyl)acetyl | 1 | H | H | H | H | H |
| 244 | cyclohexanecarbonyl | 1 | H | H | H | H | H |
| 248 | 3-phenylpropanoyl | 1 | H | H | H | H | H |
| 249 | 2-phenoxyacetyl | 1 | H | H | H | H | H |
| 252 | 2,2-dimethylpropanoyl | 1 | H | H | H | H | H |
| 254 | 2-(3,4-dimethoxyphenyl)acetyl | 1 | H | H | H | H | H |
| 255 | 3-methylbutanoyl | 1 | H | H | H | H | H |
| 256 | 2-benzyloxyacetyl | 1 | H | H | H | H | H |
| 259 | quinoxaline-2-carbonyl | 1 | H | H | H | H | H |
| 260 | cyclopropanecarbonyl | 1 | H | H | H | H | H |
| 261 | 2-(3-methoxyphenyl)acetyl | 1 | H | H | H | H | H |
| 262 | 3,3-dimethylbutanoyl | 1 | H | H | H | H | H |
| 263 | 2-cyclopentylacetyl | 1 | H | H | H | H | H |
| 264 | 2-(4-chlorophenoxy)acetyl | 1 | H | H | H | H | H |
| 265 | 2-(4-chlorophenyl)acetyl | 1 | H | H | H | H | H |
| 273 | 5-methyl-2-phenyl-triazole-4-carbonyl | 1 | H | H | H | H | H |
| 274 | 2-phenoxypyridine-3-carbonyl | 1 | H | H | H | H | H |
| 276 | 7,10-dioxabicyclo[4.4.0deca-2,4,11-triene-9-carbonyl) | 1 | H | H | H | H | H |
| 281 | 6-chloropyridine-3-carbonyl | 1 | H | H | H | H | H |
| 283 | 5-methylisoxazole-3-carbonyl | 1 | H | H | H | H | H |
| 284 | 1,5-dimethylpyrazole-3-carbonyl | 1 | H | H | H | H | H |
| 285 | 2,5-dimethylpyrazole-3-carbonyl | 1 | H | H | H | H | H |
| 286 | 1-phenyl-5-(trifluoromethyl)pyrazole-4-carbonyl | 1 | H | H | H | H | H |
| 287 | | 1 | H | H | H | H | H |
| 288 | 5-methyl-1-phenyl-pyrazole-4-carbonyl | 1 | H | H | H | H | H |
| 289 | 5-(4-chlorophenyl)-2-methyl-furan-3-carbonyl | 1 | H | H | H | H | H |
| 290 | naphthalene-2-carbonyl | 1 | H | H | H | H | H |
| 293 | 2,5-dimethylfuran-3-carbonyl | 1 | H | H | H | H | H |
| 295 | 1-acetylpiperidine-4-carbonyl | 1 | H | H | H | H | H |
| 296 | isoxazole-5-carbonyl | 1 | H | H | H | H | H |
| 297 | 3,5-dimethylisoxazole-4-carbonyl | 1 | H | H | H | H | H |
| 298 | 2-chloropyridine-4-carbonyl | 1 | H | H | H | H | H |
| 299 | 5-methylisoxazole-4-carbonyl | 1 | H | H | H | H | H |
| 300 | 5-methyl-2-tert-butyl-pyrazole-3-carbonyl | 1 | H | H | H | H | H |
| 302 | 2-(2-bromophenyl)acetyl | 1 | H | H | H | H | H |
| 303 | quinoline-2-carbonyl | 1 | H | H | H | H | H |
| 304 | pyridine-4-carbonyl | 1 | H | H | H | H | H |
| 305 | pyridme-2-carbonyl | 1 | H | H | H | H | H |
| 306 | 1-(2,2,2-trifluoroacetyl)pyrrolidine-2-carbonyl | 1 | H | H | H | H | H |
| 307 | 3-methoxypropanoyl | 1 | H | H | H | H | H |
| 308 | pyrazine-2-carbonyl | 1 | H | H | H | H | H |
| 309 | 2,3-dihydrobenzofuran-5-carbonyl | 1 | H | H | H | H | H |
| 311 | quinoxaline-6-carbonyl | 1 | H | H | H | H | H |
| 313 | chroman-3-carbonyl | 1 | H | H | H | H | H |
| 317 | 1-(2,5-dioxabicyclo[4.4.0deca-6,8,10-trien-9-yl)ethyl | 1 | H | H | H | H | H |
| 318 | 9H-fluoren-2-ylmethyl | 1 | H | H | H | H | H |
| 321 | benzo[1,3dioxol-5-ylmethyl | 1 | H | H | H | H | H |
| 332 | 1H-indol-6-ylmethyl | 1 | H | H | H | H | H |
| 333 | 2,6-dioxabicyclo[5.4.0undeca-7,9,11-trien-9-ylmethyl | 1 | H | H | H | H | H |
| 350 | (7,10-dioxabicyclo[4.4.0deca-1,3,5-trien-4-ylmethyl) | 1 | $CH_3$ | $CH_3$ | H | H | H |
| 351 | (1H-indol-6-ylmethyl) | 1 | $CH_3$ | $CH_3$ | H | H | H |
| 353 | benzylsulfonyl | 1 | $CH_3$ | $CH_3$ | H | H | H |

TABLE 1B-continued

Adamantane Substituted Amide Compounds

| ID | L¹—R³ | n | R²' | R²" | Rᵃ | Rᵇ | Rᶜ |
|---|---|---|---|---|---|---|---|
| 356 | (3,4-dichlorophenyl)methylsulfonyl | 1 | $CH_3$ | $CH_3$ | H | H | H |
| 357 | (4-chlorophenyl)methylsulfonyl | 1 | $CH_3$ | $CH_3$ | H | H | H |
| 365 | (2-cyclopentylacetyl) | 1 | $CH_3$ | $CH_3$ | H | H | H |
| 366 | (cyclohexanecarbonyl) | 1 | $CH_3$ | $CH_3$ | H | H | H |
| 367 | (3,3-dimethylbutanoyl) | 1 | $CH_3$ | $CH_3$ | H | H | H |
| 373 | 7,10-dioxabicyclo[4.4.0deca- 1,3,5-trien-4-ylmethyl) | 1 | H | H | $CH_3$ | $CH_3$ | H |
| 375 | 2-(3,5-dimethyl-1-adamantyl)-1H-indol-6-ylmethyl) | 1 | H | H | $CH_3$ | $CH_3$ | H |
| 377 | benzylsulfonyl | 1 | H | H | H | $CH_3$ | $CH_3$ |
| 378 | (3,4-dichlorophenyl)methylsulfonyl | 1 | H | H | H | $CH_3$ | $CH_3$ |
| 379 | (4-chlorophenyl)methylsulfonyl | 1 | H | H | H | $CH_3$ | $CH_3$ |
| 384 | (2-cyclopentylacetyl) | 1 | H | H | H | $CH_3$ | $CH_3$ |
| 386 | (cyclohexanecarbonyl) | 1 | H | H | H | $CH_3$ | $CH_3$ |
| 388 | (3,3-dimethylbutanoyl) | 1 | H | H | H | $CH_3$ | $CH_3$ |
| 393 | acetyl | 0 | — | — | H | H | H |
| 397 | [2-(4-methoxyphenyl)acetyl] | 0 | — | — | H | H | H |
| 398 | (2-phenylacetyl) | 0 | — | — | H | H | H |
| 409 | (2,2-diphenylacetyl) | 0 | — | — | H | H | H |
| 411 | [2-(2,5-dimethoxyphenyl)acetyl] | 0 | — | — | H | H | H |
| 412 | (2-methoxyacetyl) | 0 | — | — | H | H | H |
| 413 | [2-(4-fluorophenyl)acetyl] | 0 | — | — | H | H | H |
| 420 | (3-phenylpropanoyl) | 0 | — | — | H | H | H |
| 421 | (2-phenoxyacetyl) | 0 | — | — | H | H | H |
| 424 | (2,2-dimethylpropanoyl) | 0 | — | — | H | H | H |
| 428 | (2-benzyloxyacetyl) | 0 | — | — | H | H | H |
| 431 | (quinoxaline-2-carbonyl) | 0 | — | — | H | H | H |
| 432 | (cyclopropanecarbonyl) | 0 | — | — | H | H | H |
| 433 | [2-(3-methoxyphenyl)acetyl] | 0 | — | — | H | H | H |
| 436 | [2-(4-chlorophenoxy)acetyl] | 0 | — | — | H | H | H |
| 437 | [2-(4-chlorophenyl)acetyl] | 0 | — | — | H | H | H |
| 445 | (5-methyl-2-phenyl-triazole-4-carbonyl) | 0 | — | — | H | H | H |
| 446 | (2-phenoxypyridine-3-carbonyl) | 0 | — | — | H | H | H |
| 453 | (6-chloropyridine-3-carbonyl) | 0 | — | — | H | H | H |
| 455 | (5-methylisoxazole-3-carbonyl) | 0 | — | — | H | H | H |
| 456 | (1,5-dimethylpyrazole-3-carbonyl) | 0 | — | — | H | H | H |
| 458 | (5-methyl-1-phenyl-pyrazole-4-carbonyl) | 0 | — | — | H | H | H |
| 459 | [5-(4-chlorophenyl)-2-methyl-furan-3-carbonyl] | 0 | — | — | H | H | H |
| 460 | (naphthalene-2-carbonyl) | 0 | — | — | H | H | H |
| 463 | (2,5-dimethylfuran-3-carbonyl) | 0 | — | — | H | H | H |
| 465 | (1-acetylpiperidine-4-carbonyl) | 0 | — | — | H | H | H |
| 466 | (isoxazole-5-carbonyl) | 0 | — | — | H | H | H |
| 468 | (5-methyl-2-tert-butyl-pyrazole-3-carbonyl) | 0 | — | — | H | H | H |
| 470 | [2-(2-bromophenyl)acetyl] | 0 | — | — | H | H | H |
| 471 | (quinoline-2-carbonyl) | 0 | — | — | H | H | H |
| 472 | [1-(2,2,2-trifluoroacetyl)pyrrolidine-2-carbonyl] | 0 | — | — | H | H | H |
| 474 | (2,3-dihydrobenzofuran-5-carbonyl) | 0 | — | — | H | H | H |
| 477 | (chroman-3-carbonyl) | 0 | — | — | H | H | H |
| 480 | methylsulfonyl | 0 | — | — | H | H | H |
| 483 | (2-naphthylsulfonyl) | 0 | — | — | H | H | H |
| 484 | (8-quinolylsulfonyl) | 0 | — | — | H | H | H |
| 485 | propylsulfonyl | 0 | — | — | H | H | H |
| 486 | ethylsulfonyl | 0 | — | — | H | H | H |
| 491 | benzylsulfonyl | 0 | — | — | H | H | H |
| 494 | [(5-methyl-2-oxa-5-azabicyclo[4.4.0]deca-7,9,11-trien-9-yl)sulfonyl] | 0 | — | — | H | H | H |
| 495 | (5-chloro-1,3-dimethyl-pyrazol-4-yl)sulfonyl | 0 | — | — | H | H | H |
| 496 | (5-methyl-1-phenyl-pyrazol-4-yl)sulfonyl | 0 | — | — | H | H | H |
| 499 | (1,2-dimethylimidazol-4-yl)sulfonyl | 0 | — | — | H | H | H |
| 503 | (3,5-dimethylisoxazol-4-yl)sulfonyl | 0 | — | — | H | H | H |
| 505 | (2-oxochromen-6-yl)sulfonyl | 0 | — | — | H | H | H |
| 515 | [[3,5-bis(trifluoromethyl)phenyl]methylsulfonyl] | 0 | — | — | H | H | H |
| 516 | [[4-(trifluoromethyl)phenyl]methylsulfonyl] | 0 | — | — | H | H | H |

TABLE 1B-continued

Adamantane Substituted Amide Compounds

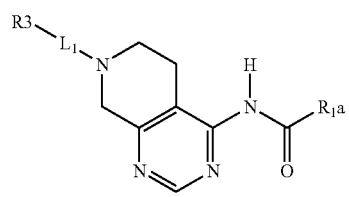

| ID | L¹—R³ | n | R²′ | R²″ | Rᵃ | Rᵇ | Rᶜ |
|---|---|---|---|---|---|---|---|
| 517 | [(4-fluorophenyl)methylsulfonyl] | 0 | — | — | H | H | H |
| 518 | [(3,4-dichlorophenyl)methylsulfonyl] | 0 | — | — | H | H | H |
| 519 | [(3,5-dichlorophenyl)methylsulfonyl] | 0 | — | — | H | H | H |
| 520 | [[3-(trifluoromethyl)phenyl]methylsulfonyl] | 0 | — | — | H | H | H |
| 522 | [(4-chlorophenyl)methylsulfonyl] | 0 | — | — | H | H | H |
| 531 | (1,3,5-trimethylpyrazol-4-yl)sulfonyl | 0 | — | — | H | H | H |
| 534 | (2,5-dioxabicyclo[4.4.0]deca-7,9,11-trien-9-ylsulfonyl) | 0 | — | — | H | H | H |
| 547 | isopropylsulfonyl | 0 | — | — | H | H | H |
| 552 | (3,5,5-trimethylhexyl) | 0 | — | — | H | H | H |
| 553 | (2,2-diphenylethyl) | 0 | — | — | H | H | H |
| 554 | (2-phenylpropyl) | 0 | — | — | H | H | H |
| 555 | propyl | 0 | — | — | H | H | H |
| 556 | (cyclohexylmethyl) | 0 | — | — | H | H | H |
| 557 | (cyclopropylmethyl) | 0 | — | — | H | H | H |
| 558 | pentyl | 0 | — | — | H | H | H |
| 559 | (3-phenylpropyl) | 0 | — | — | H | H | H |
| 560 | (3-pyridylmethyl) | 0 | — | — | H | H | H |
| 564 | (benzo[1,3]dioxol-5-ylmethyl) | 0 | — | — | H | H | H |
| 565 | (2-naphthylmethyl) | 0 | — | — | H | H | H |
| 567 | [(6-methyl-4-oxo-chromen-3-yl)methyl] | 0 | — | — | H | H | H |
| 580 | [(1-methylindol-3-yl)methyl] | 0 | — | — | H | H | H |
| 581 | (2-ethylbutyl) | 0 | — | — | H | H | H |
| 582 | (2-methylpentyl) | 0 | — | — | H | H | H |
| 583 | isopentyl | 0 | — | — | H | H | H |
| 589 | (2,5-dioxabicyclo[4.4.0]deca-6,8,10-trien-9-ylmethyl) | 0 | — | — | H | H | H |
| 596 | (benzo[1,3]dioxol-4-ylmethyl) | 0 | — | — | H | H | H |
| 599 | [(6-chlorobenzo[1,3]dioxol-5-yl)methyl] | 0 | — | — | H | H | H |
| 600 | neopentyl | 0 | — | — | H | H | H |
| 610 | (4-pyridylmethyl) | 0 | — | — | H | H | H |
| 613 | [(6-bromo-3-pyridyl)methyl] | 0 | — | — | H | H | H |
| 619 | (cyclopentylmethyl) | 0 | — | — | H | H | H |
| 627 | [(2,2-difluorobenzo[1,3]dioxol-5-yl)methyl] | 0 | — | — | H | H | H |
| 634 | [(6-chloro-3-pyridyl)methyl] | 0 | — | — | H | H | H |

TABLE 1C

Substituted Amide Compounds

| ID | L¹—R³ | R¹ᵃ |
|---|---|---|
| 9 | 4-benzyl | cyclohexylmethyl |
| 10 | 4-benzyl | cycloheptylmethyl |
| 11 | H | cyclohexylmethyl |
| 12 | H | cycloheptylmethyl |
| 20 | ethyl | cyclohexylmethyl |
| 21 | (3-hydroxypropyl) | cyclohexylmethyl |
| 22 | (2-hydroxyethyl) | cyclohexylmethyl |
| 24 | benzyl | (2-methoxyphenyl)ethyl |

TABLE 1C-continued

Substituted Amide Compounds

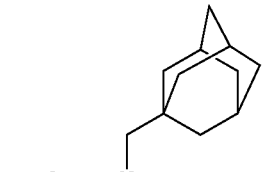

| ID | L¹—R³ | R¹ᵃ |
|---|---|---|
| 25 | H | (2-methoxyphenyl)ethyl |
| 26 | methyl | cyclohexylmethyl |
| 93 | (3-pyridylmethyl) | cycloheptylmethyl |
| 94 | (2-pyridylmethyl) | cycloheptylmethyl |
| 124 | (3-phenylpropyl) | (3-phenylpropyl) |
| 125 | (5-methyl-2-thienyl)methyl | cycloheptylmethyl |
| 126 | (1H-imidazol-4-ylmethyl) | cycloheptylmethyl |
| 127 | (cyclohexylmethyl) | cycloheptylmethyl |
| 128 | (cyclopentylmethyl) | cycloheptylmethyl |
| 129 | phenethyl | cycloheptylmethyl |
| 130 | (4-fluorophenyl)methyl | cycloheptylmethyl |
| 132 | (3-pyridylmethyl) | (2-methoxyphenyl)ethyl |
| 133 | (4-pyridyl)methyl | (2-methoxyphenyl)ethyl |
| 134 | (2-pyridylmethyl) | (2-methoxyphenyl)ethyl |
| 135 | (1H-imidazol-4-ylmethyl) | (2-methoxyphenyl)ethyl |
| 136 | (cyclohexylmethyl) | (2-methoxyphenyl)ethyl |

TABLE 1D

Substituted Amide Compounds

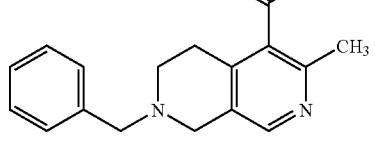

| ID | L¹—R³ | R¹ᵃ |
|---|---|---|
| 1 | benzyl | 2-(2-chlorophenyl)ethyl] |
| 2 | H | (cyclohexylmethyl) |
| 3 | H | phenethyl |
| 4 | benzyl | (cyclohexylmethyl) |
| 17 | benzyl | (1-adamantylmethyl) |
| 48 | (3-pyridylmethyl) | (cyclohexylmethyl) |
| 49 | (4-pyridylmethyl) | (cyclohexylmethyl) |
| 50 | (2-chlorophenyl)methyl | (cyclohexylmethyl) |
| 51 | (4-chlorophenyl)methyl | (cyclohexylmethyl) |
| 52 | (2-pyridylmethyl) | (cyclohexylmethyl) |
| 53 | (3-chlorophenyl)methyl | (cyclohexylmethyl) |
| 54 | (4-methoxyphenyl)methyl | (cyclohexylmethyl) |
| 55 | (p-tolylmethyl) | (cyclohexylmethyl) |
| 56 | (4-methylsulfonylphenyl)methyl | (cyclohexylmethyl) |
| 57 | (4-acetamidophenyl)methyl | 4-[(4-acetamidophenyl)methyl]-(cyclohexylmethyl) |
| 58 | benzyl | [(1-hydroxycycloheptyl)methyl] |
| 59 | benzyl | [(1-hydroxy-3,3-dimethyl-cyclohexyl)methyl] |
| 60 | benzyl | [[1-(p-tolyl)cyclohexyl]methyl] |
| 137 | (2,4-difluorophenyl)methyl | (1-adamantylmethyl) |
| 138 | (7,10-dioxabicyclo[4.4.0]deca-1,3,5-trien-4-ylmethyl) | (1-adamantylmethyl) |

TABLE 1D-continued

Substituted Amide Compounds

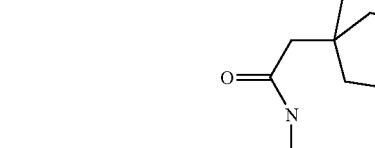

| ID | L¹—R³ | R¹ᵃ |
|---|---|---|
| 139 | [(2-fluorophenyl)methyl] | (1-adamantylmethyl) |
| 316 | [(3-fluorophenyl)methyl] | (1-adamantylmethyl) |
| 335 | [(3-methoxyphenyl)methyl] | (1-adamantylmethyl) |
| 336 | (o-tolylmethyl) | (1-adamantylmethyl) |
| 337 | [(2-chlorophenyl)methyl] | (1-adamantylmethyl) |
| 338 | (4-fluorophenyl)methyl | (1-adamantylmethyl) |
| 340 | benzo[1,3]dioxol-5-ylmethyl | (1-adamantylmethyl) |

TABLE 1E

Misc. Amide Compounds

| ID | STRUCTURE |
|---|---|
| 368 | 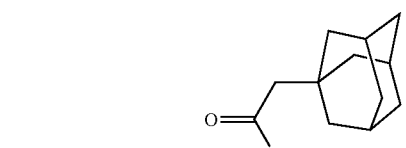 |
| 342 | 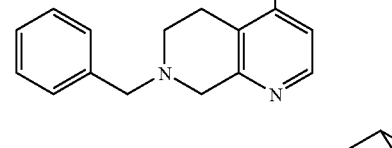 |
| 636 | 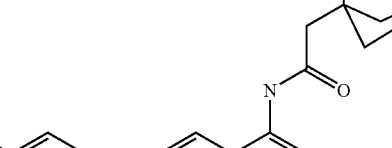 |

TABLE 2

NMR Data for Exemplary Compounds of the Invention.

| ID | NMR Data |
|---|---|
| 5 | (CDCl$_3$) 'δ' 8.68(s, 1H), 7.50(s, 1H), 7.30(m, 5H), 3.70(s, 4H), 2.74(s, 4H), 2.30(s, 2H), 1.98(br 's', 3H), 1.65(m, 12H). |
| 6 | (CDCl$_3$) 'δ' 8.70(s, 1H), 7.73(s, 1H), 4.06(s, 2H), 3.13(t, J=5.7Hz, 2H), 2.66(t, J=5.7Hz, 2H), 2.29(s, 2H), 1.99(br's', 3H), 1. |
| 7 | (CDCl3) δ 8.71(s, 1H), 7.60(s, 1H), 3.63(s, 3H), 2.91-2.83(m, 6H), 2.48(s, 2H), 2.33(s, 2H), 2.04-1.55(m, 1H). |
| 8 | (CDCl3) δ 8.71(s, 1H), 7.60(s, 1H), 3.68(s, 2H), 2.76(brs, 4H), 2.62(q, 2H), 2.34(brs, 2H), 1.99(brs, 3H), 1.80-1.48(m, 12H), 1.18(t, 3H). |
| 9 | (CD3OD) δ 8.64(s, 1H), 7.42-7.21(m, 5H), 3.73(s, 2H), 3.64(s, 2H), 2.83-2.65(m, 4H), 2.36(d, 2H), 1.95-1.50(m, 6H), 1.40-0.95(m, 5H). |
| 10 | (CD3OD) δ 8.64(s, 1H), 7.40-7.20(m, 5H), 3.73(s, 2H), 3.64(s, 2H), 2.75-2.66(m, 4H), 2.40(d, 2H), 2.10-2.0(m, 1H), 1.94-1.90(m, 12H). |
| 11 | (CD3OD) δ 8.66(s, 1H), 3.95(brs, 2H), 3.09(t, 2H), 2.67(t, 2H), 2.36(d, 2H), 1.95-0.98(m, 11H). |
| 13 | (CDCl3) δ 8.71(s, 1H), 7.89(s, 1H), 4.05-3.66(m, 3H), 3.55-3.39(m, 5H), 2.98-2.55(m, 5H), 2.28(brs, 2H), 1.99(brs, 4H), 1.75-1.60(m, 14H). |
| 17 | CD$_3$OD 'δ' 8.91(s, 1H), 7.4-7.3(m, 5H), 3.75(s, 2H), 3.7(s, 2H), 3.25(t, J=5.8, 2H), 3.08(s, 2H), 2.81(1, J=5.8, 2H), 1.98(s, 4H), 1.78-1.6(m, 16H). |
| 26 | (CD3OD) δ 8.67(s, 1H), 2.83(s, 2H), 2.72(s, 3H), 2.47(brs, 4H), 2.36(d, 2H), 1.98-1.59(m, 6H), 1.40-0.95(m, 5H). |
| 27 | (CD3OD) δ 8.65(s, 1H), 7.54-7.24(m, 4H), 3.86(s, 2H), 3.57(s, 2H), 2.84(t, 2H), 2.76(t, 2H), 2.22(s, 2H), 2.0-1.60(m, 15H). |
| 28 | (DMSO-d6) δ 10.16(s, 1H), 8.70(s, 1H), 7.32-7.27(m, 1H), 7.48(dt, 1H) 7.39-7.32(m, 1H), 7.24-7.17(m, 2H) 3.76(s, 2H), 3.61(s, 2H), 2.70(t, 2H), 2.62(t, 2H), 2.15(s, 2H) 1.93(br s, 3H) 1.70-1.53(m, 12H) |
| 30 | (CD3OD) δ 8.64(s, 1H), 7.22(d, 1H), 6.59-6.44(m, 2H), 3.81(s, 3H), 3.78(s, 3H), 3.72(s, 2H), 3.66(s, 2H), 2.81(t, 2H), 2.76(t, 2H), 2.20(s, 2H), 2.05-1.60(m, 15H). |
| 31 | (DMSO-d6) δ 10.16(s, 1H), 8.70(s, 1H), 7.32-7.27(m, 1H), 7.21-7.15(m, 3H), 3.65(s, 2H), 3.58(s, 2H), 2.68(t, 2H), 2.60(t, 2H), 2.34(s, 3H), 2.15(s, 2H) 1.93(br s, 3H) 1.70-1.53(m, 12H) |
| 39 | (CD3OD) δ 8.64(s, 1H), 7.14-7.12(m, 2H), 6.85(d, 1H), 3.81(s, 3H), 3.64(s, 2H), 3.62(s, 2H), 2.77(brs, 4H), 2.22(s, 2H), 2.17(s, 3H), 2.0-1.56(m, 15H). |
| 41 | (CD3OD) δ 8.65(s, 1H), 7.37(d, 2H), 7.33(d, 2H), 3.72(s, 2H), 3.64(s, 2H), 2.77(brs, 4H), 2.22(s, 2H), 2.0-1.48(m, 15H). |
| 46 | (CD3OD) δ 8.65(s, 1H), 6.84-6.65(m, 3H), 4.21(brs, 4H), 3.63(brs, 4H), 2.78(brs, 4H), 2.22(s, 2H), 2.04-1.60(m, 15H). |
| 47 | (CD3OD) δ 8.65(s, 1H), 7.29-7.21(m, 1H), 7.0-6.84(m, 2H), 3.79(s, 2H), 3.68(s, 2H), 2.82-2.65(m, 4H), 2.21(s, 2H), 2.05-1.60(m, 15H). |
| 58 | (CD3OD) 8.92(s, 1H), 7.41-7.25(m, 5H), 3.75(s, 2H), 3.71(s, 2H), 3.38-3.30(m, 3H), 2.81(t, 2H), 1.70-1.45(m, 13H). |
| 60 | (CD3OD) δ 8.82(s, 1H), 8.53(s, 1H), 7.20-7.05(m, 9H), 3.89-3.19(m, 8H), 3.05(t, 2H), 2.74(t, 2H), 2.20-2.05(m, 5H), 1.85-1.10(m, 7H). |
| 71 | (CD3OD) δ 8.65(s, 1H), 7.38(d, 2H), 7.29(d, 2H), 3.71(s, 2H), 3.64(s, 2H), 2.79(brs, 4H), 2.22(s, 2H), 2.0-1.60(m, 15H), 1.32(s, 9H). |
| 90 | (CD3OD) δ 8.65(s, 1H), 7.23-7.10(m, 3H), 3.85(s, 2H), 3.70(s, 2H), 2.83-2.65(m, 4H), 2.22(s, 2H), 2.01-1.60(m, 15H). |
| 107 | (CD3OD) δ 8.65(s, 1H), 7.86(dd, 1H), 7.43-7.25(m, 2H), 3.86(s, 2H), 3.69(s, 2H), 2.77(brs, 4H), 2.22(s, 2H), 2.10-1.58(m, 15H). |
| 137 | (CD3OD) δ 8.65(s, 1H), 7.60-7.41(m, 1H), 7.02-6.95(m, 2H), 3.81(s, 2H), 3.70(s, 2H), 3.03(s, 2H), 2.80(brt, 4H), 2.06-1.56(m, 15H). |
| 140 | (CD3OD) δ 8.66(s, 1H), 7.30(d, 2H), 6.90(d, 2H), 4.45(s, 2H), 3.79(s, 2H), 3.76(s, 2H), 2.96-2.70(m, 4H), 2.21(s, 2H), 2.0-1.60(m, 15H). |
| 168 | (DMSO-d6) δ 10.28(s, 1H), 8.76(s, 1H), 7.90(t, 1H), 7.86-7.78(m, 2H), 7.67(t, 1H), 4.27(s, 2H), 3.39(t, 2H), 2.66(t, 2H), 2.16(s, 2H), 1.94(br s, 3H), 1.71-1.56(m, 12H) |
| 316 | (CD3OD) δ 8.92(s, 1H), 7.36-6.90(m, 4H), 3.79(s, 2H), 3.75(s, 2H), 3.03(brs, 2H), 2.80(brs, 2H), 2.62(s, 2H), 2.10-1.56(m, 15H). |
| 321 | (DMSO-d6) δ 10.15(s, 1H), 8.70(s, 1H), 6.93-6.79(m, 3H), 6.0(s, 2H), 3.59(s, 2H), 3.55(s, 2H), 2.68-2.58(m, 4H), 2.15(s, 2H) 1.93(br s, 3H), 1.71-1.52(m, 12H) |
| 334 | (d6-DMSO) δ 9.77(s, 1H), 8.72(s, 1H), 7.20-7.10(m, 5H), 3.68(s, 2H), 3.59(s, 2H), 2.64(brs, 4H), 2.05-1.80(m, 15H). |
| 338 | (CDCl3) δ 8.89(s, 1H), 7.39-7.28(m, 2H), 7.20-6.90(m, 2H), 3.68(d, 2H), 3.46(t, 2H), 3.10(d, 2H), 2.76(t, 2H), 2.15(s, 2H), 2.0-1.20(m, 15H). |
| 339 | (CDCl3) δ 8.66(s, 1H), 7.39-7.24(m, 5H), 3.71(brs, 4H), 2.74(brs, 4H), 2.01(brs, 2H), 1.78-1.46(m, 13H), 1.25(s, 6H). |
| 368 | (CDCl3) δ 8.13(s, 1H), 7.40-7.20(m, 5H), 3.68(s, 2H), 3.58(s, 2H), 3.14(d, 2H), 2.88(t, 2H), 2.74(t, 2H), 2.51(s, 3H), 2.0(brs, 3H), 1.80-1.52(m, 12H). |
| 535 | (CDCl$_3$) δ 8.33(d, 1H), 7.97(d, 1H), 7.49(t, 1H), 7.33-7.28(m, 2H), 7.13-7.08(m, 2H), 7.02(t, 2H), 6.45(d, 1H), 5.18(s, 2H), 2.20(s, 2H), 2.02(brs, 3H), 1.75-1.54(m, 12H) |

The following biological examples, Examples 1-9, are offered to illustrate the present invention and are not to be construed in any way as limiting its scope. In the examples below, all temperatures are in degrees Celsius (unless otherwise indicated).

EXAMPLE 1

The P2X$_7$ receptor is strongly expressed in macrophage-derived cell lines, including, but not limited to, J774 (mouse macrophage line, American Type Culture Collection (ATCC), Rockville, Md., ATCC TIB-67), P388.(mouse cell line, ATCC CCL-46), P815 (mouse mast cell mastocytoma-derived line, ATCC TIB-64), THP-1 (Human monocyte-derived cell line, ATCC TIB202) and U937 (human cell line derived from histiocytic lymphoma, induceable to monocyte differentiation, ATCC CRL-1593.2) and in isolated macrophage cultures. Human or non-human animal macrophages are isolated using the procedure noted below.

The P2Z/P2X$_7$ receptor can be characterized by measuring channel opening, for instance ion flux, and/or by assessing pore formation, including by monitoring dye uptake or cell lysis in cells naturally expressing this receptor. Compounds such as ATP, 2' and 3'-(O)-(4-benzoyl benzoyl) ATP (BzATP) effect the formation of pores in the plasma membrane of these cells, particularly at low extracellular divalent ion concentrations (Buisman et al, Proc. Natl. Acad. Sci. USA 85:7988 (1988); Zambon et al, Cell. Immunol 156:458 (1994); Hickman et al Blood 84:2452 (1994)). Large molecular size dyes, including propidium dye YO-PRO-1, can be seen entering macrophage-derived cell lines during cell recordings (Hickman et al, Blood 84:2452 (1994); Wiley et al, Br J Pharmacol 112:946 (1994); Steinberg et al, J Biol Chem 262:8884 (1987)). Ethidium bromide (a fluorescent DNA probe) can also be monitored, where an increase in the fluorescence of intracellular DNA-bound ethidium bromide is observed. Expression of recombinant rat or human rP2X$_7$ in cells, including HEK293 cells, and in *Xenopus oocytes* demonstrates influx and pore formation by whole cell recordings and YO-PRO-1 fluorescence (Suprenant et al, Science 272:735 (1996); Rassendren et al, J Biol Chem 272:5482 (1997)).

The compounds of the invention may be tested for antagonist activity at the P2X$_7$ receptor. Tests that may be performed include and are selected from: (i) electrophysiological experiments; (ii) YO-PRO1 fluorescence; (iii) ethidium bromide fluorescence; and (iv) IL-1β release from stimulated macrophages, including as described below. Compounds can be tested in vivo in animal models including for inflammation models (e.g paw edema model, collagen-induced arthritis, EAE model of MS).

Isolation of Human Macrophages

Monocyte-derived human or non-human animal macrophage cultures are prepared as described by Blanchard et al (Blanchard et al, J Cell Biochem 57:452 (1995); Blanchard et al, J Immunol 147:2579 (1991)). Briefly, monocytes are isolated from leukocyte concentrates obtained from a healthy volunteer. Leukocytes are suspended in RPMI 1460 medium (Life Techologies, Inc.) with 20% serum (human for human cells), 2 mM glutamine, 5 mM HEPES, and 100 μg/ml streptomycin. Cells are allowed to adhere to culture flasks for 1-2 h, after which nonadherent cells are washed away. Adherent cells are cultured for 7-14 d in this medium plus interferon-y (human for human cells) (1000 units/ml). Macrophages are recovered from the culture flask by pipetting with cold phosphate-buffered saline and plated onto glass coverslips for electrophysiological or other experiments carried out 12-24 h later.

EXAMPLE 2

Electrophysiological Experiments

Whole cell recordings are made using the EPC9 patch-clamp amplifier and Pulse acquisition programs (HEKA, Lambrecht, Germany). Whole-cell recordings are obtained from cells, e.g. J774A.1 cells (American Type Culture Collection, Rockville, Md., ATCC TIB-67)); agonists are applied for periods of 1 to 3 s by a fast-flow U-tube delivery system [E. M. Fenwick, A. Marty, E. Neher, J. Physiol, (London) 331, 577 (1982)]. The internal pipette solution is 140 mM cesium-aspartate or potassium-aspartate, 20 mM NaCl, 10 mM EGTA, and 5 mM Hepes; normal external solution is 145 mM NaCl, 2 mM KCl, 2 mM CaCl$_2$, 1 mM MgCl$_2$, 10 mM Hepes, and 12 mM glucose. Low divalent external solution is nominally magnesium-free with 0.3 mM CaCl$_2$. Concentration-response curves are constructed in low divalent solution by recording currents in response to 1 s applications of agonist at 8 min intervals with normal external solution present for 6 min before each application. This protocol is necessary to prevent the development of sustained inward currents.

Reversal potentials (E$_{rev}$) are obtained by application of ATP (300 μM) or BzATP (30 μM)(controls), or the compound being tested, while the membrane is held at various potentials or by application of voltage ramps from −120 to 30 or 50 mV. Permeability ratios are calculated from E$_{rev}$ by first computing α (=P$_{Na}$/P$_K$, where P is permeability) for internal (i) and external (o) concentrations [Na]$_i$=20 mM, [Na]$_o$=145 mM, [K]$_o$=0 mM, and [K]$_i$=140 mM from α=([145/exp(E$_{rev}$FIRT)]−20)/140 (where F is the Faraday, R is the gas constant, and T is the absolute temperature). Other P$_x$/P$_{Na}$ values, when [X]$_o$=145 mM, [Na]$_i$=20 mM, [K]$_i$=140 mM, and [Na]$_o$=[K]$_o$=[X]$_i$=0 mM, are computed from P$_x$/P$_{Na}$=[(exp)E$_{rev}$F/RT)] (20+140α))/145. In order of size, X is cesium, methylamine, tris(hydroxymethyl)-aminomethane, tetraethylammonium, and N-methyl-D-glucamine. The internal solution also contains 10 mM EGTA and 5 mM Hepes. External solutions also contain 10 mM glucose and normal or low concentrations of divalent cations; pH is maintained at 7.3 with HCl, histidine, or Hepes as required, and the osmolarity of all solutions is 295 to 315.

EXAMPLE 3

YO-PRO1 Fluorescence

The Photonics Imaging (IDEA) system for microscopic fluorescence measurements (Photonics, Planegg, Germany) is used. Coverslips are placed at the stage of a Zeiss Axiovert 100 or equivalent inverted microscope and viewed under oil immersion with a 40× Fluor objective. YO-PRO-1 (10 μM; Molecular Probes, Eugene, Oreg.) is added to the superfusion fluid during electrophysiological recordings 3 to 6 min before switching to low divalent solution and washed out upon switching back to normal divalent solution, after which the fluorescent lamp is turned on and cells are examined with a fluorescein isothiocyanate filter. YO-PRO1 fluorescence is measured using 491/509 nm excitation/emission wavelengths. Images are obtained at 5-20 s intervals during continuous superfusion (2 ml/min) with YO-PRO1 and varying concentrations of control ATP, BzATP or compound to be tested. For each experiment, the time course of YO-PRO1 fluorescence is obtained for 10-20 individual cells and then averaged to obtain the mean fluorescence signal. Results are expressed as mean signal at 3 min for rP2X$_7$, and the signal at 10 min is used for P2X$_7$ and human macrophage cells. All experiments are carried out at room temperature.

EXAMPLE 4

Ethidium Bromide

Compounds of the invention are tested for antagonist activity at the P2X$_7$ receptor by monitoring Ethidium Bromide entering P2X$_7$ receptor-expressing cells on pore formation. The test is performed in 96-well flat bottomed microtitre plates, the wells being filled with 250 μl of test solution comprising 200 μl of a suspension of P2X$_7$-expressing cells (e.g. THP-1 cells, J774 cells, etc.)(2.5×10$^6$ cells/ml) containing 10$^{-4}$M ethidium bromide, 25 μl of a high potassium buffer solution containing 10$^{-5}$M BzATP, and 25 μl of a high potassium buffer solution containing test compound. The plate is covered with a plastic sheet and incubated at 37° C. for one hour. The plate is then read in a Perkin-Elmer fluorescent plate reader, excitation 520 nm, emission 595 nm, slit widths: Ex 15 nm, EM 20 nm. For the purposes of comparison, BzATP (a P2X$_7$ receptor agonist) and pyridoxal 5-phosphate (a P2X$_7$ receptor agonist) are used separately in the test as controls. From the readings obtained, a pIC$_{50}$ figure is calculated for each test compound. This figure is the negative logarithm of the concentration of test compound necessary to reduce the BzATP agonist activity by 50%.

EXAMPLE 5

IL-1β Release

This Example demonstrates the testing of the compounds of this invention for efficacy as inhibitors of P2X$_7$-mediated release of IL-1β from human macrophages activated by the Alzheimer's beta amyloid peptide 1-42.

Cell Isolation

Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (generally, 5 to 6 washes). Monocytes are then purified from the PBMCs by negative selection using a monocyte isolation kit (Miltenyi Biotec, Inc.) that contains antibodies to non-monocytic cells, running the cells over a magnetic column to remove antibody-bound cells, and collecting the flow through volume of monocytes. Monocytes are washed once with wash buffer and seeded at 10E5 cells per well in 100 μl serum-free RPMI 1640 in 96-well plates and incubated for 1 hour at 37° C. in a 5% CO$_2$/95% humidified tissue culture incubator. After 1 hour, the medium is replaced with 100 μl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing Regimen

The next day, the culture medium is replaced with 100 μl fresh complete culture medium in the absence or presence of human beta amyloid 142 peptide (5 μM) and incubated at 37° C. in a 5% CO$_2$/95% humidified tissue culture incubator for 5 hours. Medium is then removed and discarded. Each well is washed once with Hanks buffered saline (HBSS) containing 1 mM CaCl$_2$ followed by the addition of 80 μl of HBSS/CaCl$_2$-inhibiting compound of the present invention (10× stock in HBSS/CaCl$_2$ for a final concentration of 23 nM and 206 nM) and incubated 15 minutes in the tissue culture incubator followed by the addition of either 10 μl of HBSS/CaCl$_2$ or 10 μl of benzoyl ATP (BzATP; 3 mM stock in HBSS/CaCl$_2$ for a 300 μM final concentration) and incubated for a further 30 minutes in the tissue culture incubator. Medium is then removed to new 96-well plates for storage at −70° C. until the IL-1β content is quantitated by ELISA (from R&D Systems). The cells are washed once with HBSS/CaCl$_2$ followed by lysing the cells with 100 μl ice cold lysis buffer (100 mM Tris, pH 7.6, 1% Triton X-100, and 1 tablet per 30 ml Complete TM protease inhibitor from Roche Biochemicals, Inc). Cell lysates are stored at −70° C. until the IL-1β is quantitated by ELISA.

EXAMPLE 6

In Vivo Animal Models

A. This example illustrates the efficacy of the compounds of this invention in the treatment of multiple sclerosis. As described herein, an experimental autoimmune encephalomyelitis (EAE) model is used to show such efficacy. The following procedures are employed in this model.

Animals

SJL/J female mice, 8 wks. old, are obtained from Jackson Laboratories.

Antigens

Myelin Proteolipid Protein (PLP 139-151) (HSLGK-WLGHPDKF) (Cat #H-2478) is obtained from BACHEM, Bioscience, Inc., King of Prussia, Pa.

Complete Freund's Adjuvant H37 Ra [1 mg/ml Mycobacterium Tuberculosis H37 Ra] is obtained from Difco (Cat #3114-60-5, 6×10 ml).

Mycobacterium Tuberculosis is also obtained from Difco, (Cat #3114-33-8, 6.times 100 mg).

Pertussis Toxin

Bordetella Pertussis, (Lyophilized powder containing PBS and lactose) is obtained from List Biological Laboratories, (Product #180, 50 ug).

Induction of EAE in Mice

PLP139-151 peptide is dissolved in H$_2$O:PBS (1:1) solution to a concentration 7.5 mg/10 ml (for 75 μg PLP per group) and emulsified with an equal volume of CFA supplemented with 40 mg/10 ml heated-killed mycobacterium tuberculosis H37Ra. Mice are injected s.c. with 0.2 ml of peptide emulsion in the abdominal flank (0.1 ml on each side). On the same day and 72 hours later, mice are injected i.v. with 100% of 35 ng and 50 ng of Bordetella Pertussis toxin in saline respectively.

Clinical Assessment

STAGE 0: Normal

STAGE 0.5: Partial limp tail

STAGE 1: Complete Limp Tail

STAGE 2: Impaired righting reflex

STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE Clinical Courses of EAE Acute phase: First clinical episode (Day 10-18)

Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

B. This Example illustrates a protocol for determining the efficacy of the compounds of the present invention for the treatment of stroke using an animal model.

Male Sprague Dawley rats (Charles River) weighing 280-320 g are given free access to food and water and acclimatized for a minimum of 4 days before use in experiments. All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.

Surgical Procedure

A temporalis muscle probe is placed into the right temporalis muscle and "brain" temperature" is monitored. A midline neck incision is made in the upper thorax of the rat. Careful dissection, isolation and retraction of the sternomastoideus, digastricus, and sternohyoideus muscles is made to expose the right common, internal and external carotid arteries. The right common carotid artery is isolated with a 5-0 silk suture. During surgery the suture is released allowing reperfusion every 2-4 minutes. The right external carotid and superior thyroid arteries are also isolated and the superior thyroid is cauterized, while the external carotid is ligated distally with a 5-0 silk suture. Another 5-0 silk suture is loosely tied around the external carotid artery. The occipital artery is isolated, ligated and incised. The internal carotid is isolated.

With the common and external carotid arteries immobilized, an aneurysm clip is placed onto the internal carotid artery. A small incision is made at the distal end of the external carotid. A 3-0 nylon suture coated with poly-L-lysine is then inserted into the external carotid and up into the common carotid artery. The loosely tied 5-0 silk suture around the external carotid is now gently tightened around the filament. The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing<300 gm,19 mm for rats weighing 300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture. The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%. The neck incision is reopened to expose the external carotid artery. The restoration of blood flow is accomplished by completely withdrawing the intraluminal suture from the carotid arteries. The incision is then closed with 3-0 silk in an interrupted stitch.

Compound Administration

Five groups of 15 animals are subjected to the above methodology. Compounds are infused (I.V.) at various doses (dose response) over different time periods post MCAo.

A pre-determined concentration is infused over a pre-selected time period beginning at various intervals post MCAo. Vehicle-treated controls receive an infusion of normally 0.9 ml/hr. A positive control compound is run at the same time.

Neurological Tests

Prior to surgery, 2 hours following the onset of ischaemia and 24 hours after ischaemia, a battery of neurological tests are performed. The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation.

The rats' response to a gentle lateral push with a finger behind the shoulders is observed and noted. A normal rat would resist such a push, whereas a rat with an infarction will not. The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

C. This Example illustrates the anti-inflammatory activity of the compounds of this invention using a model of 2,4-dinitrobenzenesulfonic acid (DNBS) induced distal colitis (a model of inflammatory bowel disease).

Test Substance and Dosing Pattern

A compound of this invention is dissolved in vehicle of 2% Tween 80 in distilled water for oral administration at a dose of 50 mg/kg or dissolved in vehicle of 2% Tween 80 and 0.9% NaCl for intraperitoneal injection at 30 mg/kg. The dose is given once daily for 7 consecutive days. Dosing volume was 10 ml/kg. DNBS is challenged 2 hours after dosing on the second day.

Animals

In these studies, male Wistar, Long Evans rats provided by the animal breeding center of MDS Panlabs Taiwan, Ltd. and Balb/cByJ derived male mice (weighing 20±2 gms), provided by National Laboratory Animals Breeding Research center (NALBRC, Taiwan), may be used. Space allocation of 6 animals may be 45×23×15 cm. Animals are housed in APEC® cages (Allentown Caging, Allentown, N.J. 08501, USA) in a positive pressure isolator (NuAire®, Mode: Nu-605, airflow velocity 50±5 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water is granted. All aspects of this work including housing, experimentation and disposal of animals would be performed in general accordance with the International Guiding Principles for Biomedical Research Involving Animals (CIOMS Publication No. ISBN 92 90360194, 1985).

Chemicals

DNBS is obtained from TCI, Tokyo, Japan, ethanol is from Merck, Germany and Sulfasalazine is purchased from Sigma, USA.

Equipment

Electriconic scale (Tanita, Model 1140, Japan), Electriconic scale (Sartorius, R160P, Germany), Glass syringe (2 ml, Mitsuba, Japan), Rat oral needle, Hypodermic needle (25G×1 " TOP Corporation, Japan), Stainless Scissors (Klappenclear, Germany), Stainless Forceps (Klappenclear, Germany).

Method

Groups of 3 Wistar derived male rats weighing 180±20 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instillated into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon is removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW×100%. The "Net" increase in ratio of Vehicle-control+DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

D. This Example illustrates the anti-inflammatory activity of the present compounds using a model of carrageenan induced paw edema (a model of inflammation, carrageenan).

Test Substance and Dosing Pattern

A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.

Animals

Animals are conditioned in accordance with the procedures set forth in the previous Example.

Chemicals

Carrageenan is obtained from TCI, Japan; Pyrogen free saline is from Astar, Taiwan; and Aspirin is purchased from ICN BioMedicals, USA.

Equipment

Glass syringe (1 ml and 2 ml Mitsuba, Japan), Hypodermic needle 24G×1" (Top Corporation, Japan), Plethysmometer #7150 (Ugo Basile, Italy), and Water cell 25 mm Diameter, #7157 (UGO Basile, Italy).

Method

Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. #7150) with water cell (25 mm diameter, Cat. #7157). Reduction of hind paw edema by 30 percent or more (30%) indicated significant acute anti-inflammatory activity.

E. This Example illustrates the anti-inflammatory activity of the present compounds using a model of Balb/c mice subjected to monoclonal antibody (mAb) type II collagen induced arthritis.

Test Substance and Dosing Pattern

A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen is injected. Dosing volume is 20 ml/kg.

Animals

Animals are conditioned in accordance with the procedures set forth in the previous Example.

Chemicals

Lipopolysaccharide is obtained from Sigma, USA; Indomethacin is from Sigma, USA; Arthrogen-CIA.™. Monoclonal Antibodies D8, F10, DI-2G and A2 are obtained from IBL, Japan; Phosphated-Buffer Saline is purchased from Sigma, USA; and Tween 80 is from Wako, Japan.

Equipment

Plethysmometer (Ugo Basile, Italy) and Water Cell (Ugo Basile, Italy).

Method

Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mAbs in a total of 4 mg/mouse at day 0, and followed by intravenous 25 µg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administrated once daily for 3 consecutive days. A plethysmometer (Ugo Basile Cat #7150) with water cell (12 mm diameter) is used for the measurement of increase in volume of the two hind paws at day 0, 5, 7, 10, 14, and 17. The percent inhibition of increase in volume is calculated by the following formula:

Inhibition (%): $[1-(Tn-To)/(Cn-Co)] \times 100$

Where:
Co (Cn): volume of day 0 (day n) in vehicle control
To (Tn): volume of day 0 (day n) in test compound-treated group The reduction of both of two hind paws edema by more than 30% is considered significant.

EXAMPLE 7

Neuropathic Pain Model

This example illustrates the analgesic activity of the compounds of this invention using a Sciatic Nerve ligation model of mononeuropathic pain.

Test System
Adult male Sprague Dawley (SD) rats weighing 250-300 gm (Charles River Laboratories, San Diego, Calif.) are used. The animal room is lighted artificially at a 12-hr light-dark cycle (e.g. from 7:00 A.M. to 7:00 P.M) with water and food supply ad libitum. Animals are allocated randomly into groups.

Model Induction
Sciatic nerve ligation (SNL, Seltzer's model):
Under anesthesia with pentobarbital (50 mg/kg, i.p.) and aseptic techniques, the selective nerve injury is created by tightly ligating the selective portion of the common sciatic nerve according to the method of Seltzer (1990). Briefly, the high-thigh level of the left sciatic nerve is exposed after skin incision and blunt separation of muscles at a site near the trochanter just distal to the point at which the posterior biceps semitendious nerve nerve branches from the common sciatic nerve. The nerve is then fixed in this position with fine forceps by pinching the epineurium on its dorsal aspect, taking care not to press the nerve against underlying structures. An 8-0 silicon-treated silk suture is inserted into the nerve with a ⅜ curved, reversed-cutting mini-needle, and tightly ligated so that the dorsal ⅓-½ of the nerve is trapped in the ligature. The muscles are sutured in layers, and the skin closed with wound clips. Animals are then returned to their home cages. Rats exhibiting postoperative neurological deficits or poor grooming are excluded from the experiments.

Equipment
The following equipment is used in the current studies: von Frey filament set (Touch-test Sensory Evaluator, North Coast Medical Inc., Morgan Hill, Calif.).

Statistical Methods:
Within each experiment mean, standard error of the mean (SEM) and statistical significance are calculated using the average, standard error of the mean and unpaired, two-tailed t-Test functions, respectively, using Microsoft Excel. Statistical significance of effects observed between individual experiments is determined, using Prism (GraphPad Software Inc., San Diego, Calif.). for the one-way or two-way analysis of variance (ANOVA) function. Statistical analyses are performed with a confidence limit of 0.95 and a significance level of 0.05.

EXAMPLE 8

Pore Formation

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 IU/mL penicillin, 100 ug/mL streptomycin, 100 ng/mL LPS and 100 ng/mL IFN-γ for 16 hours. Following differentiation, the cells are pre-treated with the compound of interest at the appropriate concentration for 30 minutes in RPMI-1640 media containing 100 IU/mL penicillin, 100 ug/mL streptomycin. The pretreatment media is then replaced with assay buffer (20 mM HEPES, 10 mM D-glucose, 118 mM NMDG, 5 mM KCl, 0.4 mM $CaCl_2$) containing 5 uM Yo-Pro 1 (Molecular Probes Cat #Y3603) and the compound of interest at the appropriate concentration and the cells are incubated for an additional 10 minutes. 2', 3'-O-(4-benzoylbenzoyl)-adenosine 5'-triphosphate (Sigma Aldrich Cat#B6396) is then added to a final concentration of 40 uM and fluorescence readings measured at 491/509 excitation/emission every minute for 50 minutes using a Tecan Safire plate reader. During this time temperature is maintained at of 37° C. Background adjusted fluorescence levels between drug treated and non-treated cells are used to calculate the percent inhibition.

EXAMPLE 9

IL-1β Release Assay (Alternate Method)

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 IU/mL penicillin, 100 ug/mL streptomycin, 100 ng/mL LPS and 100 ng/mL IFN-γ for 16 hours. Following differentiation, the cells are treated for an additional 2 hours in RPMI-1640 media containing 100 IU/mL penicillin, 100 ug/mL streptomycin and fresh LPS at 100 ng/mL. The cells are then pretreated for 30 minutes with the compound of interest at the appropriate concentration in RPMI media containing 100 IU/mL penicillin, 100 ug/mL streptomycin. Following the pretreatment 2', 3'-O-(4-benzoylbenzoyl)-adenosine 5'-triphosphate (Sigma Aldrich Cat#B6396) is added to a final concentration of 250 uM and the cells incubated for an additional 45 minutes. 30 uL of cell supernatant is then collected and IL-1β levels determined via ELISA (R&D systems Cat. #HSLB50) according to manufacturer's recommendations using the Tecan Safire plate reader. Background adjusted IL-1β levels of drug treated and non-treated cells are used to calculate the percent inhibition.

The synthetic and biological examples described in this application are offered to illustrate this invention and are not to be construed in any way as limiting the scope of this invention. In the examples, all temperatures are in degrees Celsius (unless otherwise indicated). The compounds that have been prepared in accordance with the invention along with their biological activity data are presented in the following Table (Table 3). The syntheses of compounds of this invention are carried out in accordance with the methods set forth above.

Activity of Compounds of the Invention
The % Inhibition data for the representative compounds of the inventions are given in Table 3 below. For purposes of Table 3, activity of each compound is expressed as follows:

"+" compound exhibited 0-25% inhibition at 0.3 μM
"++" compound exhibited 25-50% inhibition at 0.3 μM
"+++" compound exhibited 50-75% inhibition at 0.3 μM "++++" compound exhibited 75% or greater inhibition at 0.3 μM Compounds with a percent inhibition represented by "++++" are of particular interest.

TABLE 3

Amide Compounds

| ID | Method of Synthesis | MW (calcd) | MS (obs) | IL-1β % inhibition |
|---|---|---|---|---|
| 1 | A | 406.91 | | + |
| 2 | A | 274.37 | | + |
| 3 | A | 282.35 | | + |
| 4 | A | 364.49 | | + |
| 5 | A | 416.57 | 417.78 | ++ |
| 6 | A | 326.44 | 327.58 | + |
| 7 | C | 340.47 | 341.40 | + |
| 8 | C | 354.50 | 355.72 | + |
| 9 | A | 364.49 | 365.72 | + |
| 10 | A | 378.52 | 379.69 | + |
| 11 | A | 274.37 | 275.22 | + |
| 12 | A | 288.39 | 289.56 | + |
| 13 | | 414.55 | 415.66 | + |
| 14 | C | 430.59 | 431.84 | + |
| 15 | C | 494.66 | 495.77 | + |
| 16 | C | 417.55 | 418.71 | + |
| 17 | A | 416.57 | 417.82 | ++++ |
| 18 | C | 370.49 | 371.59 | + |
| 19 | A | 384.52 | 385.60 | + |
| 20 | C | 302.42 | 303.73 | + |
| 21 | A | 332.45 | 333.72 | + |
| 22 | A | 318.42 | 319.53 | + |
| 23 | A | 400.52 | 401.64 | + |
| 24 | A | 402.50 | 403.75 | + |
| 25 | A | 312.37 | — | + |
| 26 | C | 288.39 | 289.50 | +++ |
| 27 | C | 451.01 | 452.29 | +++ |
| 28 | C | 434.56 | 435.77 | ++++ |
| 29 | C | 446.59 | 447.40 | + |
| 30 | C | 476.62 | 477.43 | ++++ |
| 31 | C | 430.59 | 431.90 | +++ |
| 32 | C | 444.62 | 445.63 | + |
| 33 | C | 434.56 | 435.25 | + |
| 34 | C | 451.01 | 451.31 | + |
| 35 | C | 446.59 | 447.69 | +++ |
| 36 | C | 476.62 | 477.44 | + |
| 37 | C | 476.62 | 477.43 | + |
| 38 | C | 430.59 | 431.82 | + |
| 39 | C | 460.62 | 461.77 | + |
| 40 | C | 446.59 | 447.73 | + |
| 41 | C | 451.01 | 451.40 | + |
| 42 | C | 441.58 | 442.62 | + |
| 43 | C | 417.55 | 418.67 | + |
| 44 | C | 430.59 | 431.69 | + |
| 45 | C | 444.62 | 445.63 | + |
| 46 | C | 474.60 | 475.45 | ++++ |
| 47 | C | 452.55 | 453.26 | ++++ |
| 48 | K | 365.48 | 366.60 | + |
| 49 | K | 365.48 | 366.63 | + |
| 50 | K | 398.94 | 399.32 | + |
| 51 | K | 398.94 | 399.32 | + |
| 52 | K | 365.48 | 366.66 | + |
| 53 | K | 398.94 | 399.34 | + |
| 54 | K | 394.52 | 395.60 | + |
| 55 | K | 378.52 | 379.73 | + |
| 56 | K | 442.58 | 443.64 | + |
| 57 | K | 421.54 | 422.67 | + |
| 58 | A | 394.52 | 395.10 | + |
| 59 | A | 408.54 | 409.41 | + |
| 60 | A | 454.61 | 455.49 | + |
| 61 | C | 417.55 | 418.74 | + |
| 62 | C | 473.62 | 474.72 | +++ |
| 63 | C | 444.62 | 445.88 | + |
| 64 | C | 455.60 | 456.71 | + |
| 65 | C | 493.65 | 494.87 | + |
| 66 | C | 436.62 | 437.43 | + |
| 67 | C | 420.56 | 421.70 | ++ |
| 68 | C | 508.66 | 509.74 | + |
| 69 | C | 467.61 | 468.86 | + |

TABLE 3-continued

Amide Compounds

| ID | Method of Synthesis | MW (calcd) | MS (obs) | IL-1β % inhibition |
|---|---|---|---|---|
| 70 | C | 484.56 | 485.78 | + |
| 71 | C | 472.67 | 473.75 | + |
| 72 | C | 484.56 | 485.77 | + |
| 73 | C | 467.61 | 468.86 | + |
| 74 | C | 500.56 | 501.76 | + |
| 75 | C | 508.66 | 509.76 | + |
| 76 | C | 500.56 | 501.82 | + |
| 77 | C | 482.57 | 483.69 | + |
| 78 | C | 482.57 | 483.70 | + |
| 79 | C | 498.69 | 499.85 | + |
| 80 | C | 462.64 | 463.81 | ++ |
| 81 | C | 420.56 | 421.67 | +++ |
| 82 | C | 406.53 | 407.71 | +++ |
| 83 | C | 457.04 | 457.37 | ++++ |
| 84 | C | 459.57 | 460.72 | + |
| 85 | C | 448.58 | 449.68 | + |
| 86 | C | 448.58 | 449.67 | ++ |
| 87 | C | 483.03 | 483.37 | ++ |
| 88 | C | 483.03 | 483.38 | +++ |
| 89 | C | 489.66 | 490.73 | + |
| 90 | C | 496.56 | 497.98 | + |
| 91 | C | 489.62 | 490.72 | + |
| 92 | C | 489.62 | 490.78 | +++ |
| 93 | C | 379.51 | 380.67 | + |
| 94 | C | 379.51 | 380.74 | + |
| 95 | C | 464.58 | 465.80 | ++++ |
| 96 | C | 502.55 | 503.68 | + |
| 97 | C | 502.55 | 503.67 | ++ |
| 98 | C | 482.63 | 483.72 | ++ |
| 99 | C | 476.62 | 477.63 | + |
| 100 | C | 476.62 | 477.65 | ++ |
| 101 | C | 476.62 | 477.63 | ++ |
| 102 | C | 464.58 | 465.83 | + |
| 103 | C | 464.58 | 465.79 | + |
| 104 | C | 464.58 | 465.81 | +++ |
| 105 | C | 458.60 | 459.75 | + |
| 106 | C | 502.55 | 503.70 | + |
| 107 | C | 502.55 | 503.68 | + |
| 108 | C | 502.55 | 503.68 | + |
| 109 | C | 502.55 | 503.75 | ++ |
| 110 | C | 502.55 | 503.70 | + |
| 111 | C | 502.55 | 503.76 | ++ |
| 112 | C | 480.65 | 481.61 | + |
| 113 | C | 474.65 | 475.72 | + |
| 114 | C | 500.56 | 501.80 | + |
| 115 | C | 486.61 | 487.73 | + |
| 116 | C | 462.66 | 463.75 | + |
| 117 | C | 462.59 | 463.68 | + |
| 118 | C | 431.58 | 432.87 | + |
| 119 | C | 464.58 | 465.80 | ++ |
| 120 | C | 484.56 | 485.78 | + |
| 121 | C | 408.59 | 409.80 | + |
| 122 | C | 422.61 | 423.72 | + |
| 123 | C | 434.56 | 435.69 | + |
| 124 | C | 406.57 | 407.78 | + |
| 125 | C | 398.57 | 399.68 | + |
| 126 | C | 368.48 | 369.61 | + |
| 127 | C | 384.56 | 385.67 | + |
| 128 | C | 370.54 | 371.71 | + |
| 129 | C | 392.54 | 393.76 | + |
| 130 | C | 396.51 | 397.70 | + |
| 131 | C | 502.55 | 503.73 | + |
| 133 | C | 403.48 | 404.68 | + |
| 134 | C | 403.48 | 404.68 | + |
| 135 | C | 392.46 | 393.40 | + |
| 136 | C | 408.54 | 409.70 | + |
| 137 | K | 452.55 | 451.46 | +++ |
| 138 | K | 474.60 | 475.66 | ++++ |
| 139 | K | 434.56 | 435.90 | ++ |
| 140 | K | 490.60 | 491.78 | + |
| 141 | C | 490.60 | 491.82 | + |
| 142 | F | 404.53 | 405.38 | +++ |
| 143 | F | 466.60 | 467.26 | + |
| 144 | F | 480.63 | 481.24 | +++ |

TABLE 3-continued

Amide Compounds

| ID | Method of Synthesis | MW (calcd) | MS (obs) | IL-1β % inhibition |
|---|---|---|---|---|
| 147 | F | 432.59 | 433.30 | ++++ |
| 148 | F | 418.56 | 419.26 | + |
| 149 | F | 496.63 | 497.39 | +++ |
| 150 | F | 501.05 | 501.20 | + |
| 151 | F | 526.65 | 527.26 | + |
| 152 | F | 484.59 | 485.33 | + |
| 153 | F | 480.63 | 481.24 | ++++ |
| 154 | F | 534.60 | 535.18 | ++++ |
| 155 | F | 535.49 | 535.03 | + |
| 157 | F | 537.68 | 538.42 | + |
| 158 | F | 519.07 | 519.30 | + |
| 159 | F | 538.59 | 539.32 | + |
| 160 | F | 546.69 | 547.31 | ++++ |
| 161 | F | 550.60 | 551.34 | ++ |
| 162 | F | 496.63 | 497.40 | + |
| 164 | F | 484.62 | 485.35 | + |
| 165 | F | 526.06 | 526.20 | +++ |
| 166 | F | 484.59 | 485.33 | ++ |
| 167 | F | 491.61 | 492.23 | ++ |
| 168 | F | 501.05 | 501.20 | ++++ |
| 169 | F | 485.61 | 486.30 | ++ |
| 172 | F | 559.69 | 560.15 | +++ |
| 173 | F | 559.69 | 560.16 | |
| 174 | F | 559.69 | 560.15 | ++++ |
| 175 | F | 588.73 | 589.31 | +++ |
| 177 | F | 626.70 | 627.38 | ++ |
| 181 | F | 569.05 | 569.20 | ++ |
| 182 | F | 616.62 | 617.35 | +++ |
| 183 | F | 548.63 | 549.32 | ++ |
| 184 | F | 498.62 | 499.25 | ++++ |
| 185 | F | 549.52 | 549.26 | ++ |
| 186 | F | 549.52 | 549.27 | ++++ |
| 187 | F | 548.63 | 549.33 | ++++ |
| 189 | F | 515.07 | 515.29 | ++++ |
| 190 | F | 532.61 | 533.16 | +++ |
| 191 | F | 558.70 | 559.21 | + |
| 192 | F | 501.05 | 501.21 | +++ |
| 193 | F | 519.04 | 519.29 | + |
| 194 | F | 542.70 | 543.28 | ++++ |
| 195 | F | 534.60 | 535.20 | + |
| 197 | F | 526.65 | 527.28 | ++++ |
| 198 | F | 498.65 | 499.31 | + |
| 199 | F | 480.63 | 481.26 | ++++ |
| 200 | F | 524.64 | 525.34 | + |
| 202 | F | 519.04 | 519.28 | ++ |
| 203 | F | 502.58 | 503.25 | + |
| 204 | F | 535.49 | 535.07 | + |
| 205 | F | 519.04 | 519.27 | + |
| 206 | F | 502.58 | 503.26 | + |
| 207 | F | 515.07 | 515.29 | +++ |
| 208 | F | 535.49 | 535.08 | +++ |
| 209 | F | 502.58 | 503.26 | ++++ |
| 210 | F | 535.49 | 535.08 | + |
| 211 | F | 519.04 | 519.27 | + |
| 212 | F | 498.62 | 499.28 | +++ |
| 214 | F | 510.66 | 511.41 | + |
| 215 | F | 484.59 | 485.34 | +++ |
| 216 | F | 526.65 | 527.28 | +++ |
| 217 | F | 494.66 | 495.35 | + |
| 218 | E | 499.44 | 499.16 | ++++ |
| 219 | E | 368.48 | 369.24 | + |
| 220 | E | 430.55 | 431.50 | ++++ |
| 222 | E | 465.98 | 466.32 | +++ |
| 223 | E | 382.51 | 383.30 | + |
| 224 | E | 474.60 | 475.26 | + |
| 225 | E | 444.58 | 445.36 | ++ |
| 227 | E | 448.54 | 449.15 | + |
| 228 | E | 514.55 | 515.31 | + |
| 229 | E | 458.60 | 459.39 | +++ |
| 230 | E | 444.58 | 445.36 | ++++ |
| 231 | E | 450.62 | 451.27 | ++ |
| 232 | E | 466.53 | 467.27 | +++ |
| 233 | E | 498.55 | 499.29 | ++++ |
| 234 | E | 460.57 | 461.28 | ++ |
| 235 | E | 466.67 | 467.33 | ++++ |
| 236 | E | 520.67 | 521.33 | +++ |
| 237 | E | 431.54 | 432.39 | + |
| 238 | E | 422.57 | 423.26 | ++++ |
| 239 | E | 504.63 | 505.27 | ++ |
| 240 | E | 398.50 | 399.25 | + |
| 241 | E | 462.57 | 463.29 | +++ |
| 242 | E | 455.56 | 456.28 | +++ |
| 243 | E | 498.55 | 499.29 | +++ |
| 244 | E | 436.60 | 437.27 | ++ |
| 245 | E | 499.44 | 499.17 | +++ |
| 246 | E | 490.60 | 491.29 | ++ |
| 247 | E | 466.53 | 467.27 | ++++ |
| 248 | E | 458.60 | 459.38 | + |
| 249 | E | 460.57 | 461.29 | + |
| 250 | E | 460.57 | 461.29 | +++ |
| 251 | E | 448.54 | 449.15 | + |
| 252 | E | 410.56 | 411.30 | ++ |
| 253 | E | 464.99 | 465.22 | +++ |
| 254 | E | 504.63 | 505.27 | + |
| 255 | E | 410.56 | 411.30 | ++ |
| 256 | E | 474.60 | 475.26 | +++ |
| 257 | E | 455.56 | 456.31 | + |
| 258 | E | 499.44 | 499.18 | ++++ |
| 260 | E | 394.52 | 395.18 | +++ |
| 261 | E | 474.60 | 475.27 | + |
| 262 | E | 424.59 | 425.28 | + |
| 263 | E | 436.60 | 437.28 | ++++ |
| 264 | E | 495.02 | 495.34 | +++ |
| 265 | E | 479.02 | 479.13 | ++ |
| 266 | E | 516.54 | 517.29 | + |
| 267 | E | 516.54 | 517.28 | ++ |
| 269 | E | 514.55 | 515.31 | ++ |
| 270 | E | 498.55 | 499.30 | + |
| 271 | E | 532.99 | 533.17 | ++++ |
| 272 | E | 482.98 | 483.30 | ++++ |
| 273 | E | 511.63 | 512.46 | ++++ |
| 274 | E | 523.63 | 524.50 | + |
| 275 | E | 490.60 | 491.29 | +++ |
| 276 | E | 488.58 | 489.33 | ++++ |
| 277 | E | 466.53 | 467.27 | +++ |
| 278 | E | 444.58 | 445.37 | +++ |
| 279 | E | 466.53 | 467.27 | ++++ |
| 280 | E | 448.54 | 449.19 | +++ |
| 281 | E | 465.98 | 466.32 | + |
| 282 | E | 499.44 | 499.19 | ++++ |
| 283 | E | 435.53 | 436.32 | +++ |
| 284 | E | 448.57 | 449.22 | ++ |
| 285 | E | 448.57 | 449.22 | + |
| 286 | E | 564.61 | 565.37 | +++ |
| 288 | E | 510.64 | 511.45 | + |
| 290 | E | 480.61 | 481.29 | ++++ |
| 291 | E | 444.58 | 445.37 | ++++ |
| 292 | E | 460.57 | 461.28 | +++ |
| 293 | E | 448.56 | 449.20 | +++ |
| 294 | E | 464.99 | 465.23 | +++ |
| 295 | E | 479.62 | 480.21 | + |
| 296 | E | 421.50 | 422.09 | +++ |
| 297 | E | 449.55 | 450.19 | + |
| 298 | E | 465.98 | 466.32 | ++++ |
| 299 | E | 435.53 | 436.32 | + |
| 300 | E | 490.65 | 491.32 | + |
| 301 | E | 486.66 | 487.36 | ++++ |
| 302 | E | 523.47 | 523.35 | +++ |
| 303 | E | 481.60 | 482.22 | +++ |
| 304 | E | 431.54 | 432.38 | + |
| 306 | E | 519.56 | 520.28 | + |
| 307 | E | 412.53 | 413.33 | ++ |
| 308 | E | 432.53 | 433.33 | |
| 309 | E | 472.59 | 473.26 | ++++ |
| 310 | E | 478.56 | 479.13 | +++ |
| 311 | E | 482.59 | 483.31 | |
| 312 | E | 490.60 | 491.29 | + |
| 313 | E | 486.61 | 487.33 | ++++ |

TABLE 3-continued

Amide Compounds

| ID | Method of Synthesis | MW (calcd) | MS (obs) | IL-1β % inhibition |
|---|---|---|---|---|
| 316 | K | 434.56 | 435.41 | + |
| 317 | C | 488.63 | 489.69 | + |
| 318 | C | 504.67 | 505.72 | + |
| 319 | C | 485.46 | 485.45 | + |
| 320 | C | 444.62 | 445.88 | + |
| 321 | C | 460.57 | 461.74 | ++++ |
| 322 | C | 452.55 | 453.60 | + |
| 323 | C | 469.00 | 469.60 | + |
| 324 | C | 481.04 | 481.39 | + |
| 325 | C | 519.01 | 519.44 | + |
| 326 | C | 469.00 | 469.61 | ++ |
| 327 | C | 552.56 | 553.75 | + |
| 328 | C | 469.00 | 469.60 | +++ |
| 329 | C | 469.00 | 469.61 | +++ |
| 330 | C | 552.72 | 553.96 | +++ |
| 331 | C | 548.68 | 549.84 | + |
| 332 | C | 455.60 | 456.75 | +++ |
| 333 | C | 488.63 | 489.78 | +++ |
| 334 | B | 402.54 | 403.72 | +++ |
| 335 | K | 446.59 | 447.72 | ++ |
| 336 | K | 430.59 | 431.84 | ++++ |
| 337 | K | 451.01 | 451.37 | ++ |
| 338 | K, B | 434.56 | 435.75 | ++++ |
| 339 | A | 444.62 | 445.89 | + |
| 340 | k | 460.57 | 461.72 | +++ |
| 341 | B | 444.62 | 445.92 | ++ |
| 342 | A | 415.58 | 416.81 | + |
| 343 | B | 472.67 | 473.86 | + |
| 344 | B | 458.65 | 459.60 | + |
| 345 | B | 486.70 | 487.64 | + |
| 346 | B | 444.62 | 445.68 | + |
| 347 | C | 480.60 | 481.32 | + |
| 348 | C | 479.06 | 479.41 | + |
| 349 | C | 458.65 | 459.61 | + |
| 350 | C | 502.66 | 503.48 | + |
| 351 | C | 483.66 | 484.42 | + |
| 352 | C | 462.61 | 463.48 | + |
| 353 | D | 508.68 | 509.78 | + |
| 354 | D | 529.10 | 529.37 | + |
| 355 | D | 530.64 | 531.58 | + |
| 356 | D | 577.57 | 577.60 | + |
| 357 | D | 543.13 | 543.54 | + |
| 358 | D | 472.63 | 473.79 | + |
| 359 | D | 526.60 | 527.74 | + |
| 360 | D | 527.49 | 527.55 | + |
| 361 | D | 494.58 | 495.77 | + |
| 362 | D | 511.04 | 511.57 | + |
| 363 | D | 494.58 | 495.82 | + |
| 364 | D | 527.49 | 527.50 | + |
| 365 | D | 464.65 | 465.74 | + |
| 366 | D | 464.65 | 465.81 | + |
| 367 | D | 452.64 | 453.70 | + |
| 368 | A | 429.60 | 430.78 | + |
| 369 | C | 462.61 | 463.49 | + |
| 370 | C | 479.06 | 479.01 | ++ |
| 371 | C | 462.61 | 463.49 | +++ |
| 372 | C | 458.65 | 459.50 | +++ |
| 373 | C | 502.66 | 503.34 | ++++ |
| 374 | C | 480.60 | 481.34 | ++ |
| 375 | C | 483.66 | 484.34 | ++ |
| 376 | C | 462.61 | 463.47 | ++ |
| 377 | D | 508.68 | 509.31 | ++++ |
| 378 | D | 577.57 | 577.18 | +++ |
| 379 | D | 543.13 | 543.50 | +++ |
| 380 | D | 529.10 | 529.26 | + |
| 381 | D | 530.64 | 531.21 | + |
| 382 | D | 472.63 | 473.40 | ++ |
| 383 | D | 526.60 | 527.41 | + |
| 384 | D | 464.65 | 465.50 | ++ |
| 385 | D | 527.49 | 527.34 | + |
| 386 | D | 464.65 | 465.50 | ++ |
| 387 | D | 494.58 | 495.26 | + |
| 388 | D | 452.64 | 453.34 | + |
| 389 | D | 511.04 | 511.25 | ++ |
| 390 | D | 494.58 | 495.26 | + |
| 391 | D | 527.49 | 527.33 | + |
| 394 | H | 416.52 | 417.34 | ++ |
| 398 | H | 430.55 | 431.33 | +++ |
| 399 | H | 450.97 | 451.08 | + |
| 400 | H | 434.51 | 435.30 | + |
| 401 | H | 500.52 | 501.23 | + |
| 402 | H | 444.58 | 445.32 | + |
| 403 | H | 430.55 | 431.33 | ++ |
| 405 | H | 452.50 | 453.02 | ++ |
| 406 | H | 484.52 | 485.32 | ++ |
| 407 | H | 446.55 | 447.19 | + |
| 409 | H | 506.65 | 507.30 | + |
| 413 | H | 448.54 | 449.02 | ++ |
| 414 | H | 441.53 | 442.31 | ++ |
| 415 | H | 484.52 | 485.32 | + |
| 417 | H | 485.41 | 485.29 | + |
| 418 | H | 476.57 | 477.23 | ++ |
| 419 | H | 452.50 | 453.03 | + |
| 421 | H | 446.55 | 447.19 | + |
| 422 | H | 446.55 | 447.19 | ++ |
| 423 | H | 434.51 | 435.30 | ++ |
| 424 | H | 396.53 | 397.24 | + |
| 425 | H | 450.97 | 451.09 | + |
| 428 | H | 460.57 | 461.28 | + |
| 430 | H | 485.41 | 485.28 | ++ |
| 433 | H | 460.57 | 461.27 | ++ |
| 436 | H | 480.99 | 481.16 | ++ |
| 437 | H | 464.99 | 465.13 | + |
| 438 | H | 502.51 | 503.26 | ++ |
| 439 | H | 502.51 | 503.27 | ++ |
| 442 | H | 484.52 | 485.32 | ++ |
| 443 | H | 518.96 | 519.28 | ++ |
| 444 | H | 468.96 | 469.29 | + |
| 446 | H | 509.61 | 510.36 | ++ |
| 449 | H | 452.50 | 453.03 | ++ |
| 450 | H | 430.55 | 431.33 | + |
| 451 | H | 452.50 | 453.02 | + |
| 452 | H | 434.51 | 435.31 | ++ |
| 453 | H | 451.96 | 452.10 | + |
| 454 | H | 485.41 | 485.29 | ++ |
| 455 | H | 421.50 | 422.02 | |
| 459 | H | 531.05 | 531.09 | |
| 460 | H | 466.58 | 467.26 | + |
| 461 | H | 430.55 | 431.33 | + |
| 463 | H | 434.54 | 435.32 | ++ |
| 464 | H | 450.97 | 451.09 | ++ |
| 466 | H | 407.47 | 408.19 | + |
| 470 | H | 509.45 | 509.21 | + |
| 471 | H | 467.57 | 468.20 | ++ |
| 475 | H | 464.54 | 465.18 | ++ |
| 476 | H | 476.57 | 477.23 | ++ |
| 477 | H | 472.59 | 473.25 | ++ |
| 479 | H | 485.41 | 485.29 | + |
| 480 | H | 390.51 | 391.30 | + |
| 481 | H | 452.58 | 453.02 | ++ |
| 482 | H | 466.60 | 467.24 | ++ |
| 483 | H | 502.64 | 503.26 | +++ |
| 485 | I | 418.56 | 419.24 | + |
| 486 | I | 404.53 | 405.33 | + |
| 487 | I | 482.60 | 483.29 | ++ |
| 488 | I | 487.02 | 487.25 | + |
| 489 | I | 512.63 | 513.33 | +++ |
| 490 | I | 470.57 | 471.35 | +++ |
| 491 | I | 466.60 | 467.25 | + |
| 492 | I | 520.57 | 521.23 | +++ |
| 493 | I | 536.57 | 537.30 | ++ |
| 494 | I | 523.65 | 524.45 | +++ |
| 495 | I | 505.04 | 505.09 | ++ |
| 497 | I | 536.57 | 537.30 | + |

TABLE 3-continued

Amide Compounds

| ID | Method of Synthesis | MW (calcd) | MS (obs) | IL-1β % inhibition |
|---|---|---|---|---|
| 498 | I | 482.60 | 483.30 | + |
| 499 | I | 470.60 | 471.38 | + |
| 500 | I | 512.03 | 512.29 | +++ |
| 501 | I | 470.57 | 471.35 | ++ |
| 503 | I | 471.58 | 472.28 | + |
| 505 | I | 520.61 | 521.23 | + |
| 506 | I | 545.66 | 546.17 | ++++ |
| 509 | I | 574.70 | 575.32 | +++ |
| 510 | I | 612.67 | 613.09 | ++++ |
| 512 | I | 558.70 | 559.19 | ++ |
| 514 | I | 555.02 | 555.07 | + |
| 515 | I | 602.60 | 603.35 | +++ |
| 516 | I | 534.60 | 535.14 | ++ |
| 517 | I | 484.59 | 485.32 | ++ |
| 518 | I | 535.49 | 535.04 | ++++ |
| 519 | I | 535.49 | 535.03 | +++ |
| 520 | I | 534.60 | 535.14 | ++ |
| 522 | I | 501.05 | 501.20 | +++ |
| 523 | I | 518.58 | 519.29 | + |
| 524 | I | 544.67 | 545.25 | ++++ |
| 525 | I | 487.02 | 487.24 | + |
| 526 | I | 505.01 | 505.07 | ++ |
| 527 | I | 528.67 | 529.17 | +++ |
| 528 | I | 520.57 | 521.23 | ++ |
| 531 | I | 484.62 | 485.34 | ++ |
| 532 | I | 536.57 | 537.30 | + |
| 533 | I | 466.60 | 467.25 | +++ |
| 534 | I | 510.61 | 511.35 | +++ |
| 535 | I | 520.57 | 521.23 | ++ |
| 536 | I | 505.01 | 505.06 | ++ |
| 537 | I | 488.56 | 489.26 | ++ |
| 538 | I | 521.47 | 521.11 | ++ |
| 539 | I | 505.01 | 505.05 | ++ |
| 540 | I | 488.56 | 489.25 | + |
| 541 | I | 501.05 | 501.19 | ++++ |
| 542 | I | 521.47 | 521.10 | + |
| 543 | I | 488.56 | 489.26 | ++ |
| 545 | I | 505.01 | 505.03 | ++ |
| 546 | I | 484.59 | 485.32 | + |
| 548 | I | 496.63 | 497.36 | + |
| 549 | I | 512.63 | 513.33 | ++ |
| 550 | I | 480.63 | 481.21 | + |
| 552 | J | 438.66 | 439.43 | ++++ |
| 553 | J | 492.66 | 493.37 | ++ |
| 554 | J | 430.59 | 431.35 | ++++ |
| 555 | J | 354.50 | 355.27 | + |
| 556 | J | 408.59 | 409.36 | + |
| 557 | J | 366.51 | 367.23 | + |
| 558 | J | 382.55 | 383.31 | ++ |
| 559 | J | 430.59 | 431.35 | ++ |
| 560 | J | 403.53 | 404.45 | ++ |
| 562 | J | 432.56 | 433.30 | + |
| 564 | J | 446.55 | 447.20 | ++++ |
| 565 | J | 452.60 | 453.09 | ++++ |
| 566 | J | 462.59 | 463.29 | + |
| 567 | J | 484.60 | 485.34 | ++ |
| 568 | J | 494.64 | 495.34 | + |
| 570 | J | 471.43 | 471.34 | ++ |
| 571 | J | 427.55 | 428.17 | ++++ |
| 572 | J | 458.65 | 459.35 | ++++ |
| 576 | J | 494.64 | 495.35 | +++ |
| 583 | J | 382.55 | 383.31 | + |
| 584 | J | 432.56 | 433.30 | + |
| 585 | J | 430.59 | 431.35 | ++ |
| 586 | J | 497.04 | 497.38 | + |
| 588 | J | 538.69 | 539.37 | ++ |
| 589 | J | 460.57 | 461.27 | +++ |
| 590 | J | 471.43 | 471.33 | + |
| 591 | J | 462.59 | 463.29 | + |
| 592 | J | 538.69 | 539.37 | ++++ |
| 593 | J | 448.56 | 449.09 | + |
| 594 | J | 541.49 | 541.24 | + |
| 595 | J | 445.54 | 446.17 | + |
| 596 | J | 446.55 | 447.20 | +++ |
| 597 | J | 481.44 | 481.05 | +++ |
| 598 | J | 436.98 | 437.12 | + |
| 599 | J | 480.99 | 481.17 | + |
| 601 | J | 436.98 | 437.12 | +++ |
| 602 | J | 416.57 | 417.37 | ++ |
| 603 | J | 427.55 | 428.16 | + |
| 604 | J | 470.54 | 471.38 | ++++ |
| 605 | J | 420.53 | 421.21 | + |
| 606 | J | 416.57 | 417.37 | + |
| 607 | J | 420.53 | 421.21 | ++++ |
| 608 | J | 462.59 | 463.30 | + |
| 610 | J | 403.53 | 404.46 | + |
| 611 | J | 454.97 | 455.21 | +++ |
| 612 | J | 488.53 | 489.30 | ++++ |
| 613 | J | 482.42 | 482.13 | + |
| 614 | J | 481.44 | 481.04 | + |
| 615 | J | 432.56 | 433.30 | +++ |
| 618 | J | 499.43 | 499.13 | + |
| 619 | J | 394.56 | 395.19 | + |
| 620 | J | 486.54 | 487.29 | ++ |
| 621 | JJ | 468.55 | 469.31 | +++ |
| 622 | J | 526.65 | 527.31 | ++ |
| 623 | J | 480.58 | 481.25 | + |
| 624 | J | 468.55 | 469.32 | + |
| 625 | J | 446.59 | 447.23 | + |
| 626 | J | 562.63 | 563.31 | ++ |
| 627 | J | 482.53 | 483.31 | ++++ |
| 628 | J | 450.55 | 451.20 | + |
| 629 | J | 450.55 | 451.20 | + |
| 630 | J | 446.59 | 447.22 | ++++ |
| 631 | J | 462.59 | 463.29 | + |
| 632 | J | 486.54 | 487.29 | ++ |
| 633 | J | 462.59 | 463.29 | + |
| 634 | J | 437.97 | 438.15 | + |
| 635 | J | 454.97 | 455.22 | + |
| 636 | J | 430.56 | | + |

Δ - Method of synthesis described in "Synthetic Methods" section

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. Also, the various groups as recited in Tables 1A-1D may be attached to the core structure in a conventional manner which should occur to those skilled in the art.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A bicycloheteroaryl compound capable of modulating P2X₇ receptor activity, in vivo, having a formula:

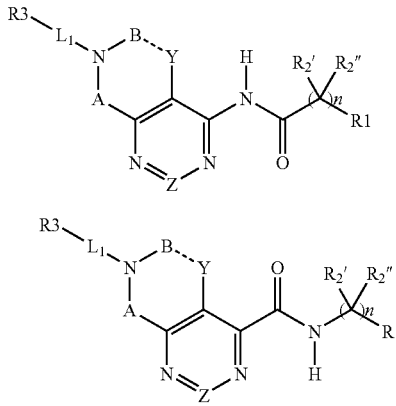

wherein
- A is selected from $CR^{2a}R^{2b}$;
- B and Y are independently selected from $CR^{2a}$ and $CR^{2a}R^{2b}$;
- Z is $CR^4$;
- $L^1$ is a bond, —CO—, —SO₂— or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy;
- n is 0, 1, 2 or 3;
- $R^1$ is selected from a 3-13 membered cycloalkyl, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;
- each of $R^{2a}$, $R^{2b}$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;
- $R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl; provided when $R^3$ is hydrogen, $L^1$ is a bond or a $C_1$-$C_5$ alkylene group;
- $R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
and the dotted bond is a single or a double bond;
or a pharmaceutically acceptable salt thereof;
and stereoisomers and tautomers thereof.

2. A compound according to claim 1 wherein each of A, B, Y is $CR^{2a}R^{2b}$; and the dotted bond is a single bond.

3. A compound according to claim 1 wherein each of A, B, Y is CH₂; and the dotted bond is a single bond.

4. A compound according to claim 1 wherein A is $CR^{2a}R^{2b}$; and each of B and Y is $CR^{2a}$; and the dotted bond is a double bond.

5. A compound according to claim 1 wherein A is CH₂; and each of B and Y is CH; and the dotted bond is a double bond.

6. A compound according to claim 1 wherein each of $R^{2'}$ and $R^{2''}$ of the

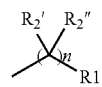

group is H.

7. A compound according to claim 3 wherein one of $R^{2'}$ and $R^{2''}$ of the

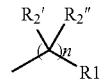

group is Me and the other is H.

8. A compound according to claim 1 wherein each of $R^{2'}$ and $R^{2''}$ of the

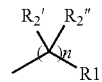

group is Me.

9. A compound according to claim 1 wherein the

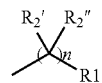

group is selected from substituted or unsubstituted

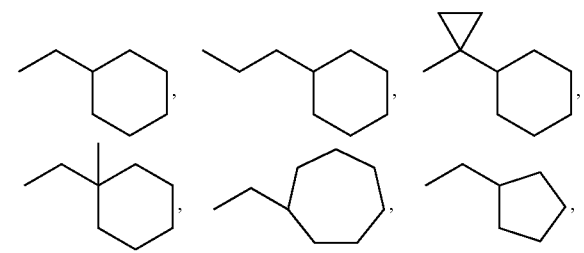

-continued

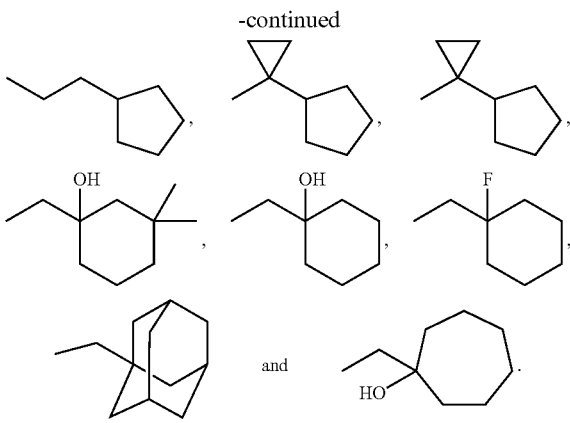

10. A compound according to claim 1 wherein the

group is

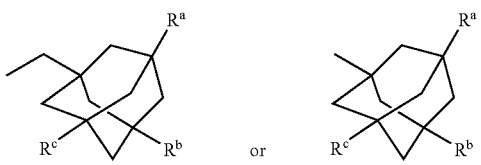

and wherein $R^a$, $R^b$ and $R^c$ are independently selected from H, halo, hydroxyl, substituted hydroxyl, alkyl, substituted alkyl, amino, substituted amino, aryl and substituted aryl.

11. A compound of claim 10 wherein $R^a$, $R^b$ and $R^c$ are independently selected from H, Br, Cl, OH, Me, NHAc, Ph and F.

12. A compound of claim 10 wherein each of $R^a$, $R^b$ and $R^c$ is H.

13. A compound according to claim 1 wherein the compound is depicted by a formula -continued

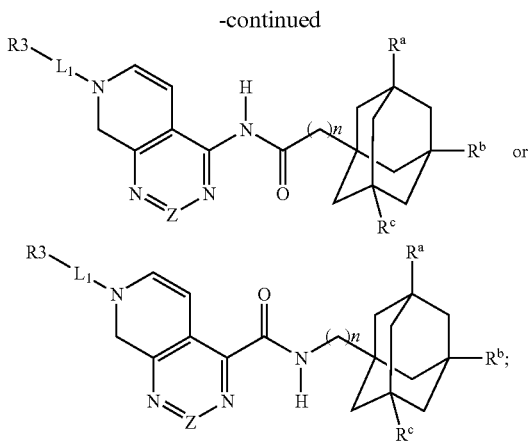

and wherein $L^1$, $R^3$, Z, and n are as described in claim 1; and wherein $R^a$, $R^b$ and $R^c$ are independently selected from H, halo, hydroxyl, substituted hydroxyl, alkyl, substituted alkyl, amino, substituted amino, aryl and substituted aryl.

14. A compound according to claim 13 wherein n is 0.

15. A compound according to claim 13 wherein n is 1.

16. A compound of claim 13 wherein each of $R^a$, $R^b$ and $R^c$ is H.

17. A compound of claim 13 wherein each of $R^a$, $R^b$ and $R^c$ is Me.

18. A compound of claim 13 wherein two of $R^a$, $R^b$ and $R^c$ is Me.

19. A compound of claim 13 wherein one of $R^a$, $R^b$ and $R^c$ is OH.

20. A compound according to either of claims 1 or 13 wherein $L^1$ is a bond and $R^3$ is H.

21. A compound according to either of claims 1 or 13 wherein $L^1$ is a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy; and $R^3$ is H.

22. A compound according to either of claims 1 or 13 wherein $L^1$ is —CO—, or —$SO_2$—.

23. A compound according to either of claims 1 or 13 wherein $L^1$ is a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy.

24. A compound according to either of claims 1 or 13 wherein $L^1$ is a $C_1$-$C_5$ alkylene group, —CO—, or —$SO_2$—; and $R^3$ is substituted or unsubstituted alkyl.

25. A compound according to either of claims 1 or 13 wherein $L^1$ is a $C_1$-$C_5$ alkylene group, —CO—, or —$SO_2$—; and $R^3$ is substituted alkyl and the substitution on alkyl is selected from aryl, heteroaryl, cycloalkyl, heterocycloalkyl, halo, alkoxy, hydroxy, cyano, and aryloxy.

26. A compound according to either of claims 1 or 13 wherein $L^1$ is a $C_1$-$C_5$ alkylene group, —CO—, or —$SO_2$—; and $R^3$ is substituted alkyl and the substitution on alkyl is selected from Ph, Cl, F, Br, CN, OH, OMe, OPh, $CF_3$, $CHF_2$, $OCF_3$, t-Bu, SMe, SOMe, $SO_2Me$, $SO_3H$, $SO_3Me$, pyridyl, cyclopropyl, cyclopentyl and cyclohexyl.

27. A compound according to either of claims 1 or 13 wherein $L^1$ is a $C_1$-$C_5$ alkylene group, —CO—, or —SO$_2$—; and $R^3$ is

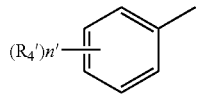

and wherein n' is selected from 1-5 and each of $R^{4'}$ is independently selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

28. A compound according to claim 27 wherein n' is 1, 2 or 3.

29. A compound according to claim 27 wherein each $R^{4'}$ is independently selected from Me, Et, Ph, Cl, F, Br, CN, OH, OMe, OPh, COPh, CF$_3$, CHF$_2$, OCF$_3$, t-Bu, SMe, CH=CH—CO$_2$H, SOMe, SO$_2$Me, SO$_3$H, SO$_3$Me, and pyridyl.

30. A compound according to either of claims 1 or 13 wherein $L^1$ is a $C_1$-$C_5$ alkylene group, —CO—, or —SO$_2$—; $R^3$ is substituted or unsubstituted cycloalkyl, heterocycloalkyl, heteroaryl, bicycloaryl or bicycloheteroaryl.

31. A compound according to either of claims 1 or 13 wherein $L^1$ is a $C_1$-$C_5$ alkylene group, —CO—, or —SO$_2$—; $R^3$ is substituted or unsubstituted naphthalene, furanyl, thiophenyl, pyrrolyl, pyrazolyl, imidazolyl, triazolyl, pyridyl, pyrimidinyl, quinoline, isoquinolinyl, tetrahydroquinolinyl, tetrahydroisoquinolinyl, indolyl, benzopyranyl, benzofuranyl, benzoxazinyl, or benzodioxanyl.

32. A compound according to either one of claims 1 or 13 wherein each of Z is CH.

33. A pharmaceutical composition comprising a pharmaceutically acceptable carrier and a pharmaceutically effective amount of a compound of claim 1.

34. The pharmaceutical composition of claim 33, wherein the carrier is a parenteral carrier.

35. The pharmaceutical composition of claim 33, wherein the carrier is an oral carrier.

36. The pharmaceutical composition of claim 33, wherein the carrier is a topical carrier.

37. A compound according to claim 1 wherein the compound is selected from

| Name |
| --- |
| 5,6,7,8-Tetrahydro-pyrido[3,4-d]pyrimidine-4-carboxylic acid cyclohexylmethyl-amide; |

-continued

| Name |
| --- |
| 7-Benzyl-5,6,7,8-tetrahydro-pyrido[3,4-d]pyrimidine-4-carboxylic acid cyclohexylmethyl-amide; |
| 7-Benzyl-5,6,7,8-tetrahydro-pyrido[3,4-d]pyrimidine-4-carboxylic acid (adamantan-1-ylmethyl)-amide; |
| 7-Pyridin-3-ylmethyl-5,6,7,8-tetrahydro-pyrido[3,4-d]pyrimidine-4-carboxylic acid cyclohexylmethyl-amide; |
| 7-Pyridin-4-ylmethyl-5,6,7,8-tetrahydro-pyrido[3,4-d]pyrimidine-4-carboxylic acid cyclohexylmethyl-amide; |
| 7-(2-Chloro-benzyl)-5,6,7,8-tetrahydro-pyrido[3,4-d]pyrimidine-4-carboxylic acid cyclohexylmethyl-amide; |
| 7-(4-Chloro-benzyl)-5,6,7,8-tetrahydro-pyrido[3,4-d]pyrimidine-4-carboxylic acid cyclohexylmethyl-amide; |
| 7-Pyridin-2-ylmethyl-5,6,7,8-tetrahydro-pyrido[3,4-d]pyrimidine-4-carboxylic acid cyclohexylmethyl-amide; |
| 7-(3-Chloro-benzyl)-5,6,7,8-tetrahydro-pyrido[3,4-d]pyrimidine-4-carboxylic acid cyclohexylmethyl-amide; |
| 7-(4-Methoxy-benzyl)-5,6,7,8-tetrahydro-pyrido[3,4-d]pyrimidine-4-carboxylic acid cyclohexylmethyl-amide; |
| 7-(4-Methyl-benzyl)-5,6,7,8-tetrahydro-pyrido[3,4-d]pyrimidine-4-carboxylic acid cyclohexylmethyl-amide; |
| 7-(4-Methanesulfonyl-benzyl)-5,6,7,8-tetrahydro-pyrido[3,4-d]pyrimidine-4-carboxylic acid cyclohexylmethyl-amide; |
| 7-(4-Acetylamino-benzyl)-5,6,7,8-tetrahydro-pyrido[3,4-d]pyrimidine-4-carboxylic acid cyclohexylmethyl-amide; |
| 7-Benzyl-5,6,7,8-tetrahydro-pyrido[3,4-d]pyrimidine-4-carboxylic acid (1-hydroxy-cycloheptylmethyl)-amide; |
| 7-Benzyl-5,6,7,8-tetrahydro-pyrido[3,4-d]pyrimidine-4-carboxylic acid (1-hydroxy-3,3-dimethyl-cyclohexylmethyl)-amide; |
| 7-Benzyl-5,6,7,8-tetrahydro-pyrido[3,4-d]pyrimidine-4-carboxylic acid (1-p-tolyl-cyclohexylmethyl)-amide; |
| 7-(2-4-Difluoro-benzyl)-5,6,7,8-tetrahydro-pyrido[3,4-d]pyrimidine-4-carboxylic acid (adamantan-1-ylmethyl)-amide; |
| 7-(2,3-Dihydro-benzo[1,4]dioxin-6-ylmethyl)-5,6,7,8-tetrahydro-pyrido[3,4-d]pyrimidine-4-carboxylic acid (adamantan-1-ylmethyl)-amide; |
| 7-(2-Fluoro-benzyl)-5,6,7,8-tetrahydro-pyrido[3,4-d]pyrimidine-4-carboxylic acid (adamantan-1-ylmethyl)-amide; |
| 7-(3-Fluoro-benzyl)-5,6,7,8-tetrahydro-pyrido[3,4-d]pyrimidine-4-carboxylic acid (adamantan-1-ylmethyl)-amide; |
| 7-(3-Methoxy-benzyl)-5,6,7,8-tetrahydro-pyrido[3,4-d]pyrimidine-4-carboxylic acid (adamantan-1-ylmethyl)-amide; |
| 7-(2-Methyl-benzyl)-5,6,7,8-tetrahydro-pyrido[3,4-d]pyrimidine-4-carboxylic acid (adamantan-1-ylmethyl)-amide; |
| 7-(2-Chloro-benzyl)-5,6,7,8-tetrahydro-pyrido[3,4-d]pyrimidine-4-carboxylic acid (adamantan-1-ylmethyl)-amide; |
| 7-(4-Fluoro-benzyl)-5,6,7,8-tetrahydro-pyrido[3,4-d]pyrimidine-4-carboxylic acid (adamantan-1-ylmethyl)-amide; |
| 7-Benzo[1,3]dioxol-5-ylmethyl-5,6,7,8-tetrahydro-pyrido[3,4-d]pyrimidine-4-carboxylic acid (adamantan-1-ylmethyl)-amide; |
| 2-Adamantan-1-yl-N-(7-benzyl-5,6,7,8-tetrahydro-pyrido[3,4-d]pyrimidin-4-yl)-acetamide; |
| 2-Adamantan-1-yl-N-(5,6,7,8-tetrahydro-pyrido[3,4-d]pyrimidin-4-yl)-acetamide; |
| 2-Adamantan-1-yl-N-(7-methyl-5,6,7,8-tetrahydro-pyrido[3,4-d]pyrimidin-4-yl)-acetamide; |
| 2-Adamantan-1-yl-N-(7-ethyl-5,6,7,8-tetrahydro-pyrido[3,4-d]pyrimidin-4-yl)-acetamide; |
| N-(7-Benzyl-5,6,7,8-tetrahydro-pyrido[3,4-d]pyrimidin-4-yl)-2-cyclohexyl-acetamide; |
| N-(7-Benzyl-5,6,7,8-tetrahydro-pyrido[3,4-d]pyrimidin-4-yl)-2-cycloheptyl-acetamide; |
| 2-Cyclohexyl-N-(5,6,7,8-tetrahydro-pyrido[3,4-d]pyrimidin-4-yl)-acetamide; |
| 2-Cycloheptyl-N-(5,6,7,8-tetrahydro-pyrido[3,4-d]pyrimidin-4-yl)-acetamide; |
| 2-Adamantan-1-yl-N-[7-(2-hydroxy-3-methoxy-propyl)-5,6,7,8-tetrahydro-pyrido[3,4-d]pyrimidin-4-yl]-acetamide; |
| 2-Adamantan-1-yl-N-(7-phenethyl-5,6,7,8-tetrahydro-pyrido[3,4-d]pyrimidin-4-yl)-acetamide; |
| 2-Adamantan-1-yl-N-[7-(4-methanesulfonyl-benzyl)-5,6,7,8-tetrahydro-pyrido[3,4-d]pyrimidin-4-yl]-acetamide; |
| 2-Adamantan-1-yl-N-(7-pyridin-3-ylmethyl-5,6,7,8-tetrahydro-pyrido[3,4-d]pyrimidin-4-yl)-acetamide; |
| 2-Adamantan-1-yl-N-[7-(2-hydroxy-ethyl)-5,6,7,8-tetrahydro-pyrido(3,4-d]pyridin-4-yl]-acetamide; |
| 2-Adamantan-1-yl-N-[7-(3-hydroxy-propyl)-5,6,7,8-tetrahydro-pyrido[3,4-d]pyridin-4-yl]-acetamide; |

| Name |
|---|
| 2-Cyclohexyl-N-(7-ethyl-5,6,7,8-tetrahydro-pyrido[3,4-d]pyrimidin-4-yl)-acetamide; |
| 2-Cyclohexyl-N-[7-(3-hydroxy-propyl)-5,6,7,8-tetrahydro-pyrido[3,4-d]pyrimidin-4-yl]-acetamide; |
| 2-Cyclohexyl-N-[7-(2-hydroxy-ethyl)-5,6,7,8-tetrahydro-pyrido[3,4-d]pyrimidin-4-yl]-acetamide; |
| 2-Adamantan-1-yl-N-[7-(2,3-dihydroxy-propyl)-5,6,7,8-tetrahydro-pyrido[3,4-d]pyrimidin-4-yl]-acetamide; |
| 2-Cyclohexyl-N-(7-methyl-5,6,7,8-tetrahydro-pyrido[3,4-d]pyrimidin-4-yl)-acetamide; |
| 2-Adamantan-1-yl-N-[7-(2-chloro-benzyl)-5,6,7,8-tetrahydro-pyrido[3,4-d]pyrimidin-4-yl]-acetamide; |
| 2-Adamantan-1-yl-N-[7-(2-fluoro-benzyl)-5,6,7,8-tetrahydro-pyrido[3,4-d]pyrimidin-4-yl]-acetamide; |
| 2-Adamantan-1-yl-N-[7-(2-methoxy-benzyl)-5,6,7,8-tetrahydro-pyrido[3,4-d]pyrimidin-4-yl]-acetamide; |
| 2-Adamantan-1-yl-N-[7-(2,4-dimethoxy-benzyl)-5,6,7,8-tetrahydro-pyrido[3,4-d]pyrimidin-4-yl]-acetamide; |
| 2-Adamantan-1-yl-N-[7-(2-methyl-benzyl)-5,6,7,8-tetrahydro-pyrido[3,4-d]pyrimidin-4-yl]-acetamide; |
| 2-Adamantan-1-yl-N-[7-(2,5-dimethyl-benzyl)-5,6,7,8-tetrahydro-pyrido[3,4-d]pyrimidin-4-yl]-acetamide; |
| 2-Adamantan-1-yl-N-[7-(3-fluoro-benzyl)-5,6,7,8-tetrahydro-pyrido[3,4-d]pyrimidin-4-yl]-acetamide; |
| 2-Adamantan-1-yl-N-[7-(3-chloro-benzyl)-5,6,7,8-tetrahydro-pyrido[3,4-d]pyrimidin-4-yl]-acetamide; |
| 2-Adamantan-1-yl-N-[7-(3-methoxy-benzyl)-5,6,7,8-tetrahydro-pyrido[3,4-d]pyrimidin-4-yl]-acetamide; |
| 2-Adamantan-1-yl-N-[7-(3,4-dimethoxy-benzyl)-5,6,7,8-tetrahydro-pyrido[3,4-d]pyrimidin-4-yl]-acetamide; |
| 2-Adamantan-1-yl-N-[7-(3,5-dimethoxy-benzyl)-5,6,7,8-tetrahydro-pyrido[3,4-d]pyrimidin-4-yl]-acetamide; |
| 2-Adamantan-1-yl-N-[7-(3-methyl-benzyl)-5,6,7,8-tetrahydro-pyrido[3,4-d]pyrimidin-4-yl]-acetamide; |
| 2-Adamantan-1-yl-N-[7-(4-methoxy-3-methyl-benzyl)-5,6,7,8-tetrahydro-pyrido[3,4-d]pyrimidin-4-yl]-acetamide; |
| 2-Adamantan-1-yl-N-[7-(4-methoxy-benzyl)-5,6,7,8-tetrahydro-pyrido[3,4-d]pyrimidin-4-yl]-acetamide; |
| 2-Adamantan-1-yl-N-[7-(4-chloro-benzyl)-5,6,7,8-tetrahydro-pyrido[3,4-d]pyrimidin-4-yl]-acetamide; |
| 2-Adamantan-1-yl-N-[7-(4-cyano-benzyl)-5,6,7,8-tetrahydro-pyrido[3,4-d]pyrimidin-4-yl]-acetamide; |
| 2-Adamantan-1-yl-N-(7-pyridin-4-ylmethyl-5,6,7,8-tetrahydro-pyrido[3,4-d]pyrimidin-4-yl)-acetamide; |
| 2-Adamantan-1-yl-N-[7-(4-methyl-benzyl)-5,6,7,8-tetrahydro-pyrido[3,4-d]pyrimidin-4-yl]-acetamide; |
| 2-Adamantan-1-yl-N-[7-(4-ethyl-benzyl)-5,6,7,8-tetrahydro-pyrido[3,4-d]pyrimidin-4-yl]-acetamide; |
| 2-Adamantan-1-yl-N-[7-(2,3-dihydro-benzo[1,4]dioxin-6-ylmethyl)-5,6,7,8-tetrahydro-pyrido[3,4-d]pyrimidin-4-yl]-acetamide; |
| 2-Adamantan-1-yl-N-[7-(2,4-difluoro-benzyl)-5,6,7,8-tetrahydro-pyrido[3,4-d]pyrimidin-4-yl]-acetamide; |
| 2-Adamantan-1-yl-N-(7-pyridin-2-ylmethyl-5,6,7,8-tetrahydro-pyrido[3,4-d]pyrimidin-4-yl)-acetamide; |
| N-[7-(4-Acetylamino-benzyl)-5,6,7,8-tetrahydro-pyrido[3,4-d]pyrimidin-4-yl]-2-adamantan-1-yl-acetamide; |
| 2-Adamantan-1-yl-N-[7-(3-phenyl-propyl)-5,6,7,8-tetrahydro-pyrido[3,4-d]pyrimidin-4-yl]-acetamide; |
| 2-Adamantan-1-yl-N-[7-(1H-indol-5-ylmethyl)-5,6,7,8-tetrahydro-pyrido[3,4-d]pyrimidin-4-yl]-acetamide; |
| 2-Adamantan-1-yl-N-[7-(4-pyridin-2-yl-benzyl)-5,6,7,8-tetrahydro-pyrido[3,4-d]pyrimidin-4-yl]-acetamide; |
| 2-Adamantan-1-yl-N-[7-(5-methyl-thiophen-2-ylmethyl)-5,6,7,8-tetrahydro-pyrido[3,4-d]pyrimidin-4-yl]-acetamide; |
| 2-Adamantan-1-yl-N-[7-(1-methyl-1H-imidazol-2-ylmethyl)-5,6,7,8-tetrahydro-pyrido[3,4-d]pyrimidin-4-yl]-acetamide; |
| 2-Adamantan-1-yl-N-[7-(3-phenoxy-benzyl)-5,6,7,8-tetrahydro-pyrido[3,4-d]pyrimidin-4-yl]-acetamide; |
| 2-Adamantan-1-yl-N-(7-quinolin-4-ylmethyl-5,6,7,8-tetrahydro-pyrido[3,4-d]pyrimidin-4-yl)-acetamide; |
| 2-Adamantan-1-yl-N-[7-(3-trifluoromethyl-benzyl)-5,6,7,8-tetrahydro-pyrido[3,4-d]pyrimidin-4-yl]-acetamide; |
| 2-Adamantan-1-yl-N-[7-(4-tert-butyl-benzyl)-5,6,7,8-tetrahydro-pyrido[3,4-d]pyrimidin-4-yl]-acetamide; |
| 2-Adamantan-1-yl-N-[7-(4-trifluoromethyl-benzyl)-5,6,7,8-tetrahydro-pyrido[3,4-d]pyrimidin-4-yl]-acetamide; |
| 2-Adamantan-1-yl-N-(7-quinolin-2-ylmethyl-5,6,7,8-tetrahydro-pyrido[3,4-d]pyrimidin-4-yl)-acetamide; |
| 2-Adamantan-1-yl-N-[7-(4-trifluoromethoxy-benzyl)-5,6,7,8-tetrahydro-pyrido[3,4-d]pyrimidin-4-yl]-acetamide; |
| 2-Adamantan-1-yl-N-[7-(4-phenoxy-benzyl)-5,6,7,8-tetrahydro-pyrido[3,4-d]pyrimidin-4-yl]-acetamide; |
| 2-Adamantan-1-yl-N-[7-(2-trifluoromethoxy-benzyl)-5,6,7,8-tetrahydro-pyrido[3,4-d]pyrimidin-4-yl]-acetamide; |
| 2-Adamantan-1-yl-N-[7-(2-difluoromethoxy-benzyl)-5,6,7,8-tetrahydro-pyrido[3,4-d]pyrimidin-4-yl]-acetamide; |
| 2-Adamantan-1-yl-N-[7-(4-difluoromethoxy-benzyl)-5,6,7,8-tetrahydro-pyrido[3,4-d]pyrimidin-4-yl]-acetamide; |
| 2-Adamantan-1-yl-N-[7-(5-phenyl-thiophen-2-ylmethyl)-5,6,7,8-tetrahydro-pyrido[3,4-d]pyrimidin-4-yl]-acetamide; |
| 2-Adamantan-1-yl-N-[7-(2-butyl-1H-imidazol-4-ylmethyl)-5,6,7,8-tetrahydro-pyrido[3,4-d]pyrimidin-4-yl]-acetamide; |
| 2-Adamantan-1-yl-N-[7-(5-methyl-3H-imidazol-4-ylmethyl)-5,6,7,8-tetrahydro-pyrido[3,4-d]pyrimidin-4-yl]-acetamide; |
| 2-Adamantan-1-yl-N-[7-(1H-imidazol-4-ylmethyl)-5,6,7,8-tetrahydro-pyrido[3,4-d]pyrimidin-4-yl]-acetamide; |
| 2-Adamantan-1-yl-N-[7-(5-chloro-thiophen-2-ylmethyl)-5,6,7,8-tetrahydro-pyrido[3,4-d]pyrimidin-4-yl]-acetamide; |
| 2-Adamantan-1-yl-N-[7-(3-cyano-4-fluoro-benzyl)-5,6,7,8-tetrahydro-pyrido[3,4-d]pyrimidin-4-yl]-acetamide; |
| 2-Adamantan-1-yl-N-[7-(3-fluoro-4-methyl-benzyl)-5,6,7,8-tetrahydro-pyrido[3,4-d]pyrimidin-4-yl]-acetamide; |
| 2-Adamantan-1-yl-N-[7-(4-fluoro-3-methyl-benzyl)-5,6,7,8-tetrahydro-pyrido[3,4-d]pyrimidin-4-yl]-acetamide; |
| 2-Adamantan-1-yl-N-[7-(6-chloro-2-fluoro-3-methyl-benzyl)-5,6,7,8-tetrahydro-pyrido[3,4-d]pyrimidin-4-yl]-acetamide; |
| 2-Adamantan-1-yl-N-[7-(2-chloro-6-fluoro-3-methyl-benzyl)-5,6,7,8-tetrahydro-pyrido[3,4-d]pyrimidin-4-yl]-acetamide; |
| 2-Adamantan-1-yl-N-(7-{4-[(2-hydroxy-ethyl)-methyl-amino]-benzyl}-5,6,7,8-tetrahydro-pyrido[3,4-d]pyrimidin-4-yl)-acetamide; |
| 2-Adamantan-1-yl-N-[7-(2,2-difluoro-benzo[1,3]dioxol-4-ylmethyl)-5,6,7,8-tetrahydro-pyrido[3,4-d]pyrimidin-4-yl]-acetamide; |
| 2-{4-[4-(2-Adamantan-1-yl-acetylamino)-5,8-dihydro-6H-pyrido[3,4 d]pyrimidin-7-ylmethyl]-phenoxy}-acetamide; |
| 2-{2-[4-(2-Adamantan-1-yl-acetylamino)-5,8-dihydro-6H-pyrido[3,4-d]pyrimidin-7-ylmethyl]-phenoxy}-acetamide; |
| 2-Cycloheptyl-N-(7-pyridin-3-ylmethyl-5,6,7,8-tetrahydro-pyrido(3,4-d]pyrimidin-4-yl)-acetamide; |
| 2-Cycloheptyl-N-(7-pyridin-2-ylmethyl-5,6,7,8-tetrahydro-pyrido[3,4-d]pyrimidin-4-yl)-acetamide; |
| 2-Adamantan-1-yl-N-[7-(2-fluoro-4-methoxy-benzyl)-5,6,7,8-tetrahydro-pyrido[3,4-d]pyrimidin-4-yl]-acetamide; |
| 2-Adamantan-1-yl-N-[7-(5-fluoro-2-trifluoromethyl-benzyl)-5,6,7,8-tetrahydro-pyrido[3,4-d]pyrimidin-4-yl]-acetamide; |
| 2-Adamantan-1-yl-N-[7-(3-fluoro-4-trifluoromethyl-benzyl)-5,6,7,8-tetrahydro-pyrido[3,4-d]pyrimidin-4-yl]-acetamide; |
| 2-Adamantan-1-yl-N-[7-(4-imidazol-1-yl-benzyl)-5,6,7,8-tetrahydro-pyrido[3,4-d]pyrimidin-4-yl]-acetamide; |
| 2-Adamantan-1-yl-N-{7-[4-(2-hydroxy-ethoxy)-benzyl]-5,6,7,8-tetrahydro-pyrido[3,4-d]pyrimidin-4-yl}-acetamide; |
| 2-Adamantan-1-yl-N-{7-[2-(2-hydroxy-ethoxy)-benzyl]-5,6,7,8-tetrahydro-pyrido[3,4-d]pyrimidin-4-yl}-acetamide; |
| 2-Adamantan-1-yl-N-{7-[3-(2-hydroxy-ethoxy)-benzyl]-5,6,7,8-tetrahydro-pyrido[3,4-d]pyrimidin-4-yl}-acetamide; |
| 2-Adamantan-1-yl-N-[7-(5-fluoro-2-methoxy-benzyl)-5,6,7,8-tetrahydro-pyrido[3,4-d]pyrimidin-4-yl]-acetamide; |
| 2-Adamantan-1-yl-N-[7-(4-fluoro-3-methoxy-benzyl)-5,6,7,8-tetrahydro-pyrido[3,4-d]pyrimidin-4-yl]-acetamide; |
| 2-Adamantan-1-yl-N-[7-(2-fluoro-5-methoxy-benzyl)-5,6,7,8-tetrahydro-pyrido[3,4-d]pyrimidin-4-yl]-acetamide; |
| 2-Adamantan-1-yl-N-[7-(2,3-dihydro-benzofuran-5-ylmethyl)-5,6,7,8-tetrahydro-pyrido[3,4-d]pyrimidin-4-yl]-acetamide |
| 2-Adamantan-1-yl-N-[7-(4-fluoro-3-trifluoromethyl-benzyl)-5,6,7,8-tetrahydro-pyrido[3,4-d]pyrimidin-4-yl]-acetamide; |
| 2-Adamantan-1-yl-N-[7-(4-fluoro-2-trifluoromethyl-benzyl)-5,6,7,8-tetrahydro-pyrido[3,4-d]pyrimidin-4-yl]-acetamide; |
| 2-Adamantan-1-yl-N-[7-(3-fluoro-5-trifluoromethyl-benzyl)-5,6,7,8-tetrahydro-pyrido[3,4-d]pyrimidin-4-yl]-acetamide; |
| 2-Adamantan-1-yl-N-[7-(2-fluoro-5-trifluoromethyl-benzyl)-5,6,7,8-tetrahydro-pyrido[3,4-d]pyrimidin-4-yl]-acetamide; |
| 2-Adamantan-1-yl-N-[7-(2-fluoro-4-trifluoromethyl-benzyl)-5,6,7,8-tetrahydro-pyrido[3,4-d]pyrimidin-4-yl]-acetamide; |

| Name |
|---|
| 2-Adamantan-1-yl-N-[7-(2-fluoro-6-trifluoromethyl-benzyl)-5,6,7,8-tetrahydro-pyrido[3,4-d]pyrimidin-4-yl]-acetamide; |
| 2-Adamantan-1-yl-N-[7-(4-methyl-naphthalen-1-ylmethyl)-5,6,7,8-tetrahydro-pyrido[3,4-d]pyrimidin-4-yl]-acetamide; |
| 2-Adamantan-1-yl-N-[7-(4-isopropoxy-benzyl)-5,6,7,8-tetrahydro-pyrido[3,4-d]pyrimidin-4-yl]-acetamide; |
| 2-Adamantan-1-yl-N-[7-(3-trifluoromethoxy-benzyl)-5,6,7,8-tetrahydro-pyrido[3,4-d]pyrimidin-4-yl]-acetamide; |
| (E)-3-{4-[4-(2-Adamantan-1-yl-acetylamino)-5,8-dihydro-6H-pyrido[3,4-d]pyrimidin-7-ylmethyl]-phenyl}-acrylic acid; |
| 2-Adamantan-1-yl-N-[7-(4-methylsulfanyl-benzyl)-5,6,7,8-tetrahydro-pyrido[3,4-d]pyrimidin-4-yl]-acetamide; |
| 2-Adamantan-1-yl-N-[7-(4-hydroxy-3-methoxy-benzyl)-5,6,7,8-tetrahydro-pyrido[3,4-d]pyrimidin-4-yl]-acetamide; |
| 2-Adamantan-1-yl-N-[7-(6-methyl-pyridin-2-ylmethyl)-5,6,7,8-tetrahydro-pyrido[3,4-d]pyrimidin-4-yl]-acetamide; |
| 2-Adamantan-1-yl-N-[7-(3-fluoro-4-methoxy-benzyl)-5,6,7,8-tetrahydro-pyrido[3,4-d]pyrimidin-4-yl]-acetamide; |
| 2-Adamantan-1-yl-N-[7-(2-trifluoromethyl-benzyl)-5,6,7,8-tetrahydro-pyrido[3,4-d]pyrimidin-4-yl]-acetamide; |
| 2-Adamantan-1-yl-N-(7-cyclopentylmethyl-5,6,7,8-tetrahydro-pyrido[3,4-d]pyrimidin-4-yl)-acetamide; |
| 2-Adamantan-1-yl-N-(7-cyclohexylmethyl-5,6,7,8-tetrahydro-pyrido[3-4-d]pyrimidin-4-yl)-acetamide; |
| 2-Adamantan-1-yl-N-[7-(4-fluoro-benzyl)-5,6,7,8-tetrahydro-pyrido[3,4-d]pyrimidin-4-yl]-acetamide; |
| 2-Cycloheptyl-N-[7-(3-phenyl-propyl)-5,6,7,8-tetrahydro-pyrido[3,4-d]pyrimidin-4-yl]-acetamide; |
| 2-Cycloheptyl-N-[7-(5-methyl-thiophen-2-ylmethyl)-5,6,7,8-tetrahydro-pyrido[3,4-d]pyrimidin-4-yl]-acetamide; |
| 2-Cycloheptyl-N-[7-(1H-imidazol-4-ylmethyl)-5,6,7,8-tetrahydro-pyrido[3,4-d]pyrimidin-4-yl]-acetamide; |
| 2-Cycloheptyl-N-(7-cyclohexylmethyl-5,6,7,8-tetrahydro-pyrido(3-4-d]pyrimidin-4-yl)-acetamide; |
| 2-Cycloheptyl-N-(7-cyclopentylmethyl-5,6,7,8-tetrahydro-pyrido[3,4-d]pyrimidin-4-yl)-acetamide; |
| 2-Cycloheptyl-N-(7-phenethyl-5,6,7,8-tetrahydro-pyrido(3,4-d]pyrimidin-4-yl)-acetamide; |
| 2-Cycloheptyl-N-[7-(4-fluoro-benzyl)-5,6,7,8-tetrahydro-pyrido[3,4-d]pyrimidin-4-yl]-acetamide; |
| 2-Adamantan-1-yl-N-[7-(2-fluoro-3-trifluoromethyl-benzyl)-5,6,7,8-tetrahydro-pyrido[3,4-d]pyrimidin-4-yl]-acetamide; |
| {4-[4-(2-Adamantan-1-yl-acetylamino)-5,8-dihydro-6H-pyrido[3,4-d]pyrimidin-7-ylmethyl]-phenoxy}-acetic acid; |
| {2-[4-(2-Adamantan-1-yl-acetylamino)-5,8-dihydro-6H-pyrido[3,4-d]pyrimidin-7-ylmethyl]-phenoxy}-acetic acid; |
| 2-Adamantan-1-yl-N-(7-methanesulfonyl-5,6,7,8-tetrahydro-pyrido[3,4-d]pyrimidin-4-yl)-acetamide; |
| 2-Adamantan-1-yl-N-(7-benzenesulfonyl-5,6,7,8-tetrahydro-pyrido[3,4-d]pyrimidin-4-yl)-acetamide; |
| 2-Adamantan-1-yl-N-[7-(toluene-4-sulfonyl)-5,6,7,8-tetrahydro-pyrido[3,4-d]pyrimidin-4-yl]-acetamide; |
| 2-Adamantan-1-yl-N-[7-(naphthalene-2-sulfonyl)-5,6,7,8-tetrahydro-pyrido[3,4-d]pyrimidin-4-yl]-acetamide; |
| 2-Adamantan-1-yl-N-[7-(quinoline-8-sulfonyl)-5,6,7,8-tetrahydro-pyrido[3,4-d]pyrimidin-4-yl]-acetamide; |
| 2-Adamantan-1-yl-N-[7-(propane-1-sulfonyl)-5,6,7,8-tetrahydro-pyrido[3,4-d]pyrimidin-4-yl]-acetamide; |
| 2-Adamantan-1-yl-N-(7-ethanesulfonyl-5,6,7,8-tetrahydro-pyrido[3,4-d]pyrimidin-4-yl)-acetamide; |
| 2-Adamantan-1-yl-N-[7-(4-methoxy-benzenesulfonyl)-5,6,7,8-tetrahydro-pyrido[3,4-d]pyrimidin-4-yl]-acetamide; |
| 2-Adamantan-1-yl-N-[7-(4-chloro-benzenesulfonyl)-5,6,7,8-tetrahydro-pyrido[3,4-d]pyrimidin-4-yl]-acetamide; |
| 2-Adamantan-1-yl-N-[7-(3,4-dimethoxy-benzenesulfonyl)-5,6,7,8-tetrahydro-pyrido[3,4-d]pyrimidin-4-yl]-acetamide; |
| 2-Adamantan-1-yl-N-[7-(4-fluoro-benzenesulfonyl)-5,6,7,8-tetrahydro-pyrido[3,4-d]pyrimidin-4-yl]-acetamide; |
| 2-Adamantan-1-yl-N-(7-phenylmethanesulfonyl-5,6,7,8-tetrahydro-pyrido[3,4-d]pyrimidin-4-yl)-acetamide; |
| 2-Adamantan-1-yl-N-[7-(3-trifluoromethyl-benzenesulfonyl)-5,6,7,8-tetrahydro-pyrido[3,4-d]pyrimidin-4-yl]-acetamide; |
| 2-Adamantan-1-yl-N-[7-(3,4-dichloro-benzenesulfonyl)-5,6,7,8-tetrahydro-pyrido[3,4-d]pyrimidin-4-yl]-acetamide; |
| 2-Adamantan-1-yl-N-[7-(4-trifluoromethoxy-benzenesulfonyl)-5,6,7,8-tetrahydro-pyrido[3,4-d]pyrimidin-4-yl]-acetamide; |
| 2-Adamantan-1-yl-N-[7-(4-methyl-3,4-dihydro-2H-benzo[1,4]oxazine-7-sulfonyl)-5,6,7,8-tetrahydro-pyrido[3,4-d]pyrimidin-4-yl]-acetamide; |
| 2-Adamantan-1-yl-N-[7-(5-chloro-1,3-dimethyl-1H-pyrazole-4-sulfonyl)-5,6,7,8-tetrahydro-pyrido[3,4-d]pyrimidin-4-yl]-acetamide; |
| 2-Adamantan-1-yl-N-[7-(5-methyl-2-trifluoromethyl-furan-3-sulfonyl)-5,6,7,8-tetrahydro-pyrido[3,4-d]pyrimidin-4-yl]-acetamide; |
| 2-Adamantan-1-yl-N-[7-(5-methyl-1-phenyl-1H-pyrazole-4-sulfonyl)-5,6,7,8-tetrahydro-pyrido[3,4-d]pyrimidin-4-yl]-acetamide; |
| 2-Adamantan-1-yl-N-[7-(3-trifluoromethoxy-benzenesulfonyl)-5,6,7,8-tetrahydro-pyrido[3,4-d]pyrimidin-4-yl]-acetamide; |
| 2-Adamantan-1-yl-N-[7-(3-methoxy-benzenesulfonyl)-5,6,7,8-tetrahydro-pyrido[3,4-d]pyrimidin-4-yl]-acetamide; |
| 2-Adamantan-1-yl-N-[7-(1-methyl-1H-imidazole-4-sulfonyl)-5,6,7,8-tetrahydro-pyrido[3,4-d]pyrimidin-4-yl]-acetamide; |
| 2-Adamantan-1-yl-N-[7-(1,2-dimethyl-1H-imidazole-4-sulfonyl)-5,6,7,8-tetrahydro-pyrido[3,4-d]pyrimidin-4-yl]-acetamide; |
| 2-Adamantan-1-yl-N-[7-(2-chloro-4-cyano-benzenesulfonyl)-5,6,7,8-tetrahydro-pyrido[3,4-d]pyrimidin-4-yl]-acetamide; |
| 2-Adamantan-1-yl-N-[7-(2-fluoro-benzenesulfonyl)-5,6,7,8-tetrahydro-pyrido[3,4-d]pyrimidin-4-yl]-acetamide; |
| 2-Adamantan-1-yl-N-[7-(4-cyano-benzenesulfonyl)-5,6,7,8-tetrahydro-pyrido[3,4-d]pyrimidin-4-yl]-acetamide; |
| 2-Adamantan-1-yl-N-[7-(3-chloro-benzenesulfonyl)-5,6,7,8-tetrahydro-pyrido[3,4-d]pyrimidin-4-yl]-acetamide; |
| 2-Adamantan-1-yl-N-[7-(3,5-dimethyl-isoxazole-4-sulfonyl)-5,6,7,8-tetrahydro-pyrido[3,4-d]pyrimidin-4-yl]-acetamide; |
| 2-Adamantan-1-yl-N-(7-methanesulfonylmethanesulfonyl-5,6,7,8-tetrahydro-pyrido[3,4-d]pyrimidin-4-yl)-acetamide; |
| 2-Adamantan-1-yl-N-[7-(2-oxo-2H-chromene-6-sulfonyl)-5,6,7,8-tetrahydro-pyrido[3,4-d]pyrimidin-4-yl]-acetamide; |
| 2-Adamantan-1-yl-N-{7-[4-(pyridin-2-yloxy)-benzenesulfonyl]-5,6,7,8-tetrahydro-pyrido[3,4-d]pyrimidin-4-yl}-acetamide; |
| 2-Adamantan-1-yl-N-{7-[4-(pyridin-3-yloxy)-benzenesulfonyl]-5,6,7,8-tetrahydro-pyrido[3,4-d]pyrimidin-4-yl}-acetamide; |
| 2-Adamantan-1-yl-N-{7-[4-(pyridin-4-yloxy)-benzenesulfonyl]-5,6,7,8-tetrahydro-pyrido[3,4-d]pyrimidin-4-yl}-acetamide; |
| 2-Adamantan-1-yl-N-{7-[4-(4-methoxy-phenoxy)-benzenesulfonyl]-5,6,7,8-tetrahydro-pyrido[3,4-d]pyrimidin-4-yl}-acetamide; |
| 2-Adamantan-1-yl-N-{7-[4-(3,4-dichloro-phenoxy)-benzenesulfonyl]-5,6,7,8-tetrahydro-pyrido[3,4-d]pyrimidin-4-yl}-acetamide; |
| 2-Adamantan-1-yl-N-{7-[4-(4-trifluoromethyl-phenoxy)-benzenesulfonyl]-5,6,7,8-tetrahydro-pyrido[3,4-d]pyrimidin-4-yl}-acetamide; |
| 2-Adamantan-1-yl-N-{7-[3-(3,4-dichloro-phenoxy)-benzenesulfonyl]-5,6,7,8-tetrahydro-pyrido[3,4-d]pyrimidin-4-yl}-acetamide; |
| 2-Adamantan-1-yl-N-[7-(4[40 -methoxy-biphenyl-4-sulfonyl)-5,6,7,8-tetrahydro-pyrido[3,4-d]pyrimidin-4-yl]-acetamide; |
| 2-Adamantan-1-yl-N-[7-(pyridine-3-sulfonyl)-5,6,7,8-tetrahydro-pyrido[3,4-d]pyrimidin-4-yl]-acetamide; |
| 2-Adamantan-1-yl-N-[7-(2-chloro-5-trifluoromethyl-benzenesulfonyl)-5,6,7,8-tetrahydro-pyrido[3,4-d]pyrimidin-4-yl]-acetamide; |
| 2-Adamantan-1-yl-N-[7-(3,5-bis-trifluoromethyl-phenylmethanesulfonyl)-5,6,7,8-tetrahydro-pyrido[3,4-d]pyrimidin-4-yl]-acetamide; |
| 2-Adamantan-1-yl-N-[7-(4-trifluoromethyl-phenylmethanesulfonyl)-5,6,7,8-tetrahydro-pyrido[3,4-d]pyrimidin-4-yl]-acetamide; |
| 2-Adamantan-1-yl-N-[7-(4-fluoro-phenylmethanesulfonyl)-5,6,7,8-tetrahydro-pyrido[3,4-d]pyrimidin-4-yl]-acetamide; |
| 2-Adamantan-1-yl-N-[7-(3,4-dichloro-phenylmethanesulfonyl)-5,6,7,8-tetrahydro-pyrido[3,4-d]pyrimidin-4-yl]-acetamide; |
| 2-Adamantan-1-yl-N-[7-(3,5-dichloro-phenylmethanesulfonyl)-5,6,7,8-tetrahydro-pyrido[3,4-d]pyrimidin-4-yl]-acetamide; |
| 2-Adamantan-1-yl-N-[7-(3-trifluoromethyl-phenylmethanesulfonyl)-5,6,7,8-tetrahydro-pyrido[3,4-d]pyrimidin-4-yl]-acetamide; |
| 2-Adamantan-1-yl-N-(7-p-tolylmethanesulfonyl-5,6,7,8-tetrahydro-pyrido[3,4-d]pyrimidin-4-yl)-acetamide; |
| 2-Adamantan-1-yl-N-[7-(4-chloro-phenylmethanesulfonyl)-5,6,7,8-tetrahydro-pyrido[3,4-d]pyrimidin-4-yl]-acetamide; |
| 2-Adamantan-1-yl-N-[7-(4-difluoromethoxy-benzenesulfonyl)-5,6,7,8-tetrahydro-pyrido[3,4-d]pyrimidin-4-yl]-acetamide; |
| 2-Adamantan-1-yl-N-[7-(4-phenoxy-benzenesulfonyl)-5,6,7,8-tetrahydro-pyrido[3,4-d]pyrimidin-4-yl]-acetamide; |

| Name |
|---|
| 2-Adamantan-1-yl-N-[7-(2-chloro-benzenesulfonyl)-5,6,7,8-tetrahydro-pyrido[3,4-d]pyrimidin-4-yl]-acetamide;
2-Adamantan-1-yl-N-[7-(3-chloro-4-fluoro-benzenesulfonyl)-5,6,7,8-tetrahydro-pyrido[3,4-d]pyrimidin-4-yl]-acetamide;
2-Adamantan-1-yl-N-[7-(biphenyl-2-sulfonyl)-5,6,7,8-tetrahydro-pyrido[3,4-d]pyrimidin-4-yl]-acetamide;
2-Adamantan-1-yl-N-[7-(2-trifluoromethyl-benzenesulfonyl)-5,6,7,8-tetrahydro-pyrido[3,4-d]pyrimidin-4-yl]-acetamide;
2-Adamantan-1-yl-N-[7-(4-pyrazol-1-yl-benzenesulfonyl)-5,6,7,8-tetrahydro-pyrido[3,4-d]pyrimidin-4-yl]-acetamide;
2-Adamantan-1-yl-N-[7-(2,4-dimethoxy-benzenesulfonyl)-5,6,7,8-tetrahydro-pyrido[3,4-d]pyrimidin-4-yl]-acetamide;
2-Adamantan-1-yl-N-[7-(1,3,5-trimethyl-1H-pyrazole-4-sulfonyl)-5,6,7,8-tetrahydro-pyrido[3,4-d]pyrimidin-4-yl]-acetamide;
2-Adamantan-1-yl-N-[7-(toluene-2-sulfonyl)-5,6,7,8-tetrahydro-pyrido[3,4-d]pyrimidin-4-yl]-acetamide;
2-Adamantan-1-yl-N-[7-(2,3-dihydro-benzo[1,4]dioxine-6-sulfonyl)-5,6,7,8-tetrahydro-pyrido[3,4-d]pyrimidin-4-yl]-acetamide;
2-Adamantan-1-yl-N-[7-(4-trifluoromethyl-benzenesulfonyl)-5,6,7,8-tetrahydro-pyrido[3,4-d]pyrimidin-4-yl]-acetamide;
2-Adamantan-1-yl-N-[7-(4-chloro-2-fluoro-benzenesulfonyl)-5,6,7,8-tetrahydro-pyrido[3,4-d]pyrimidin-4-yl]-acetamide;
2-Adamantan-1-yl-N-[7-(2,5-difluoro-benzenesulfonyl)-5,6,7,8-tetrahydro-pyrido[3,4-d]pyrimidin-4-yl]-acetamide;
2-Adamantan-1-yl-N-[7-(2,5-dichloro-benzenesulfonyl)-5,6,7,8-tetrahydro-pyrido[3,4-d]pyrimidin-4-yl]-acetamide;
2-Adamantan-1-yl-N-[7-(5-chloro-2-fluoro-benzenesulfonyl)-5,6,7,8-tetrahydro-pyrido[3,4-d]pyrimidin-4-yl]-acetamide;
2-Adamantan-1-yl-N-[7-(2,6-difluoro-benzenesulfonyl)-5,6,7,8-tetrahydro-pyrido[3,4-d]pyrimidin-4-yl]-acetamide;
2-Adamantan-1-yl-N-[7-(3-chloro-4-methyl-benzenesulfonyl)-5,6,7,8-tetrahydro-pyrido[3,4-d]pyrimidin-4-yl]-acetamide;
2-Adamantan-1-yl-N-[7-(3,5-dichloro-benzenesulfonyl)-5,6,7,8-tetrahydro-pyrido[3,4-d]pyrimidin-4-yl]-acetamide;
2-Adamantan-1-yl-N-[7-(2,4-difluoro-benzenesulfonyl)-5,6,7,8-tetrahydro-pyrido[3,4-d]pyrimidin-4-yl]-acetamide;
2-Adamantan-1-yl-N-[7-(2,6-dichloro-benzenesulfonyl)-5,6,7,8-tetrahydro-pyrido[3,4-d]pyrimidin-4-yl]-acetamide;
2-Adamantan-1-yl-N-[7-(2-chloro-4-fluoro-benzenesulfonyl)-5,6,7,8-tetrahydro-pyrido[3,4-d]pyrimidin-4-yl]-acetamide;
2-Adamantan-1-yl-N-[7-(5-fluoro-2-methyl-benzenesulfonyl)-5,6,7,8-tetrahydro-pyrido[3,4-d]pyrimidin-4-yl]-acetamide;
2-Adamantan-1-yl-N-[7-(propane-2-sulfonyl)-5,6,7,8-tetrahydro-pyrido[3,4-d]pyrimidin-4-yl]-acetamide;
2-Adamantan-1-yl-N-[7-(2-methoxy-5-methyl-benzenesulfonyl)-5,6,7,8-tetrahydro-pyrido[3,4-d]pyrimidin-4-yl]-acetamide;
2-Adamantan-1-yl-N-[7-(3-fluoro-benzenesulfonyl)-5,6,7,8-tetrahydro-pyrido[3,4-d]pyrimidin-4-yl]-acetamide;
2-Adamantan-1-yl-N-[7-(2,5-dimethoxy-benzenesulfonyl)-5,6,7,8-tetrahydro-pyrido[3,4-d]pyrimidin-4-yl]-acetamide;
2-Adamantan-1-yl-N-[7-(3,5-dimethyl-benzenesulfonyl)-5,6,7,8-tetrahydro-pyrido[3,4-d]pyrimidin-4-yl]-acetamide;
2-Adamantan-1-yl-N-[7-(2,6-dichlorobenzoyl)-5,6,7,8-tetrahydro-pyrido[3,4-d]pyrimidin-4-yl]-acetamide;
N-(7-Acetyl-5,6,7,8-tetrahydro-pyrido[3,4-d]pyrimidin-4-yl)-2-adamantan-1-yl-acetamide;
2-Adamantan-1-yl-N-(7-benzoyl-5,6,7,8-tetrahydro-pyrido[3,4-d]pyrimidin-4-yl)-acetamide;
2-Adamantan-1-yl-N-[7-(biphenyl-4-carbonyl)-5,6,7,8-tetrahydro-pyrido[3-4-d]pyrimidin-4-yl]-acetamide;
2-Adamantan-1-yl-N-[7-(2-chloro-pyridine-3-carbonyl)-5,6,7,8-tetrahydro-pyrido[3,4-d]pyrimidin-4-yl]-acetamide;
2-Adamantan-1-yl-N-(7-propionyl-5,6,7,8-tetrahydro-pyrido[3,4-d]pyrimidin-4-yl)-acetamide;
2-Adamantan-1-yl-N-{7-[2-(4-methoxy-phenyl)-acetyl]-5,6,7,8-tetrahydro-pyrido[3,4-d]pyrimidin-4-yl -acetamide;
2-Adamantan-1-yl-N-(7-phenylacetyl-5,6,7,8-tetrahydro-pyrido[3,4-d]pyrimidin-4-yl)-acetamide;
2-Adamantan-1-yl-N-[7-(4-chloro-benzoyl)-5,6,7,8-tetrahydro-pyrido[3,4-d]pyrimidin-4-yl]-acetamide;
2-Adamantan-1-yl-N-[7-(3-fluoro-benzoyl)-5,6,7,8-tetrahydro-pyrido[3,4-d]pyrimidin-4-yl]-acetamide;
2-Adamantan-1-yl-N-[7-(4-trifluoromethoxy-benzoyl)-5,6,7,8-tetrahydro-pyrido[3,4-d]pyrimidin-4-yl]-acetamide;
2-Adamantan-1-yl-N-[7-(4-ethyl-benzoyl)-5,6,7,8-tetrahydro-pyrido[3,4-d]pyrimidin-4-yl]-acetamide; |

| Name |
|---|
| 2-Adamantan-1-yl-N-[7-(3-methyl-benzoyl)-5,6,7,8-tetrahydro-pyrido[3,4-d]pyrimidin-4-yl]-acetamide;
2-Adamantan-1-yl-N-[7-(3-cyclopentyl-propionyl)-5,6,7,8-tetrahydro-pyrido[3,4-d]pyrimidin-4-yl]-acetamide;
2-Adamantan-1-yl-N-[7-(3,4-difluoro-benzoyl)-5,6,7,8-tetrahydro-pyrido[3,4-d]pyrimidin-4-yl]-acetamide;
2-Adamantan-1-yl-N-[7-(3-trifluoromethyl-benzoyl)-5,6,7,8-tetrahydro-pyrido[3,4-d]pyrimidin-4-yl]-acetamide;
2-Adamantan-1-yl-N-[7-(4-methoxy-benzoyl)-5,6,7,8-tetrahydro-pyrido[3,4-d]pyrimidin-4-yl]-acetamide;
2-Adamantan-1-yl-N-[7-(3,5,5-trimethyl-hexanoyl)-5,6,7,8-tetrahydro-pyrido[3,4-d]pyrimidin-4-yl]-acetamide;
2-Adamantan-1-yl-N-(7-diphenylacetyl-5,6,7,8-tetrahydro-pyrido[3,4-d]pyrimidin-4-yl)-acetamide;
2-Adamantan-1-yl-N-[7-(pyridine-3-carbonyl)-5,6,7,8-tetrahydro-pyrido[3,4-d]pyrimidin-4-yl]-acetamide;
2-Adamantan-1-yl-N-(7-cyclopentanecarbonyl-5,6,7,8-tetrahydro-pyrido[3,4-d]pyrimidin-4-yl)-acetamide;
2-Adamantan-1-yl-N-{7-[2-(2-5-dimethoxy-phenyl)-acetyl]-5,6,7,8-tetrahydro-pyrido[3,4-d]pyrimidin-4-yl}-acetamide;
2-Adamantan-1-yl-N-[7-(2-methoxy-acetyl)-5,6,7,8-tetrahydro-pyrido[3,4-d]pyrimidin-4-yl]-acetamide;
2-Adamantan-1-yl-N-{7-[2-(4-fluoro-phenyl)-acetyl]-5,6,7,8-tetrahydro-pyrido[3,4-d]pyrimidin-4-yl}-acetamide;
2-Adamantan-1-yl-N-[7-(3-cyano-benzoyl)-5,6,7,8-tetrahydro-pyrido[3,4-d]pyrimidin-4-yl]-acetamide;
2-Adamantan-1-yl-N-[7-(4-trifluoromethyl-benzoyl)-5,6,7,8-tetrahydro-pyrido[3,4-d]pyrimidin-4-yl]-acetamide;
2-Adamantan-1-yl-N-(7-cyclohexanecarbonyl-5,6,7,8-tetrahydro-pyrido[3,4-d]pyrimidin-4-yl)-acetamide;
2-Adamantan-1-yl-N-[7-(3,4-dichloro-benzoyl)-5,6,7,8-tetrahydro-pyrido[3,4-d]pyrimidin-4-yl]-acetamide;
2-Adamantan-1-yl-N-[7-(3,5-dimethoxy-benzoyl)-5,6,7,8-tetrahydro-pyrido[3,4-d]pyrimidin-4-yl]-acetamide;
2-Adamantan-1-yl-N-[7-(2,6-difluoro-benzoyl)-5,6,7,8-tetrahydro-pyrido[3,4-d]pyrimidin-4-yl]-acetamide;
2-Adamantan-1-yl-N-[7-(3-phenyl-propionyl)-5,6,7,8-tetrahydro-pyrido[3,4-d]pyrimidin-4-yl]-acetamide;
2-Adamantan-1-yl-N-[7-(2-phenoxy-acetyl)-5,6,7,8-tetrahydro-pyrido[3,4-d]pyrimidin-4-yl]-acetamide;
2-Adamantan-1-yl-N-[7-(3-methoxy-benzoyl)-5,6,7,8-tetrahydro-pyrido[3,4-d]pyrimidin-4-yl]-acetamide;
2-Adamantan-1-yl-N-[7-(4-fluoro-benzoyl)-5,6,7,8-tetrahydro-pyrido[3,4-d]pyrimidin-4-yl]-acetamide;
2-Adamantan-1-yl-N-[7-(2,2-dimethyl-propionyl)-5,6,7,8-tetrahydro-pyrido[3,4-d]pyrimidin-4-yl]-acetamide;
2-Adamantan-1-yl-N-[7-(3-chloro-benzoyl)-5,6,7,8-tetrahydro-pyrido[3,4-d]pyrimidin-4-yl]-acetamide;
2-Adamantan-1-yl-N-{7-[2-(3-4-dimethoxy-phenyl)-acetyl]-5,6,7,8-tetrahydro-pyrido[3,4-d]pyrimidin-4-yl}-acetamide;
2-Adamantan-1-yl-N-[7-(3-methyl-butyryl)-5,6,7,8-tetrahydro-pyrido[3,4-d]pyrimidin-4-yl]-acetamide;
2-Adamantan-1-yl-N-[7-(2-benzyloxy-acetyl)-5,6,7,8-tetrahydro-pyrido[3,4-d]pyrimidin-4-yl]-acetamide;
2-Adamantan-1-yl-N-[7-(4-cyano-benzoyl)-5,6,7,8-tetrahydro-pyrido[3,4-d]pyrimidin-4-yl]-acetamide;
2-Adamantan-1-yl-N-[7-(2,4-dichloro-benzoyl)-5,6,7,8-tetrahydro-pyrido[3,4-d]pyrimidin-4-yl]-acetamide;
2-Adamantan-1-yl-N-[7-(quinoxaline-2-carbonyl)-5,6,7,8-tetrahydro-pyrido[3,4-d]pyrimidin-4-yl]-acetamide;
2-Adamantan-1-yl-N-(7-cyclopropanecarbonyl-5,6,7,8-tetrahydro-pyrido[3,4-d]pyrimidin-4-yl)-acetamide;
2-Adamantan-1-yl-N-{7-[2-(3-methoxy-phenyl)-acetyl]-5,6,7,8-tetrahydro-pyrido[3,4-d]pyrimidin-4-yl}-acetamide;
2-Adamantan-1-yl-N-[7-(3,3-dimethyl-butyryl)-5,6,7,8-tetrahydro-pyrido[3,4-d]pyrimidin-4-yl]-acetamide;
2-Adamantan-1-yl-N-[7-(2-cyclopentyl-acetyl)-5,6,7,8-tetrahydro-pyrido[3,4-d]pyrimidin-4-yl]-acetamide;
2-Adamantan-1-yl-N-{7-[2-(4-chloro-phenoxy)-acetyl]-5,6,7,8-tetrahydro-pyrido[3,4-d]pyrimidin-4-yl}-acetamide;
2-Adamantan-1-yl-N-{7-[2-(4-chloro-phenyl)-acetyl]-5,6,7,8-tetrahydro-pyrido[3,4-d]pyrimidin-4-yl}-acetamide;
2-Adamantan-1-yl-N-[7-(2-fluoro-4-trifluoromethyl-benzoyl)-5,6,7,8-tetrahydro-pyrido[3,4-d]pyrimidin-4-yl]-acetamide;
2-Adamantan-1-yl-N-[7-(3-fluoro-5-trifluoromethyl-benzoyl)-5,6,7,8-tetrahydro-pyrido[3,4-d]pyrimidin-4-yl]-acetamide; |

| Name |
|---|
| 2-Adamantan-1-yl-N-[7-(2-trifluoromethoxy-benzoyl)-5,6,7,8-tetrahydro-pyrido[3,4-d]pyrimidin-4-yl]-acetamide;
2-Adamantan-1-yl-N-[7-(3-trifluoromethoxy-benzoyl)-5,6,7,8-tetrahydro-pyrido[3,4-d]pyrimidin-4-yl]-acetamide;
2-Adamantan-1-yl-N-[7-(2-trifluoromethyl-benzoyl)-5,6,7,8-tetrahydro-pyrido[3,4-d]pyrimidin-4-yl]-acetamide;
2-Adamantan-1-yl-N-[7-(2-chloro-5-trifluoromethyl-benzoyl)-5,6,7,8-tetrahydro-pyrido[3,4-d]pyrimidin-4-yl]-acetamide;
2-Adamantan-1-yl-N-[7-(2-chloro-6-fluoro-benzoyl)-5,6,7,8-tetrahydro-pyrido[3,4-d]pyrimidin-4-yl]-acetamide;
2-Adamantan-1-yl-N-[7-(5-methyl-2-phenyl-2H-[1,2,3]triazole-4-carbonyl)-5,6,7,8-tetrahydro-pyrido[3,4-d]pyrimidin-4-yl]-acetamide;
2-Adamantan-1-yl-N-[7-(2-phenoxy-pyridine-3-carbonyl)-5,6,7,8-tetrahydro-pyrido[3,4-d]pyrimidin-4-yl]-acetamide;
2-Adamantan-1-yl-N-[7-(2,4-dimethoxy-benzoyl)-5,6,7,8-tetrahydro-pyrido[3,4-d]pyrimidin-4-yl]-acetamide;
2-Adamantan-1-yl-N-[7-(2,3-dihydro-benzo[1,4]dioxine-2-carbonyl)-5,6,7,8-tetrahydro-pyrido[3-4-d]pyrimidin-4-yl]-acetamide;
2-Adamantan-1-yl-N-[7-(2,4-difluoro-benzoyl)-5,6,7,8-tetrahydro-pyrido[3,4-d]pyrimidin-4-yl]-acetamide;
2-Adamantan-1-yl-N-[7-(2-methyl-benzoyl)-5,6,7,8-tetrahydro-pyrido[3,4-d]pyrimidin-4-yl]-acetamide;
2-Adamantan-1-yl-N-[7-(2,5-difluoro-benzoyl)-5,6,7,8-tetrahydro-pyrido[3,4-d]pyrimidin-4-yl]-acetamide;
2-Adamantan-1-yl-N-[7-(2-fluoro-benzoyl)-5,6,7,8-tetrahydro-pyrido[3,4-d]pyrimidin-4-yl]-acetamide;
2-Adamantan-1-yl-N-[7-(6-chloro-pyridine-3-carbonyl)-5,6,7,8-tetrahydro-pyrido[3,4-d]pyrimidin-4-yl]-acetamide;
2-Adamantan-1-yl-N-[7-(2,3-dichloro-benzoyl)-5,6,7,8-tetrahydro-pyrido[3,4-d]pyrimidin-4-yl]-acetamide;
2-Adamantan-1-yl-N-[7-(5-methyl-isoxazole-3-carbonyl)-5,6,7,8-tetrahydro-pyrido[3,4-d]pyrimidin-4-yl]-acetamide;
2-Adamantan-1-yl-N-[7-(1,5-dimethyl-1H-pyrazole-3-carbonyl)-5,6,7,8-tetrahydro-pyrido[3,4-d]pyrimidin-4-yl]-acetamide;
2-Adamantan-1-yl-N-[7-(2,5-dimethyl-2H-pyrazole-3-carbonyl)-5,6,7,8-tetrahydro-pyrido[3,4-d]pyrimidin-4-yl]-acetamide;
2-Adamantan-1-yl-N-[7-(1-phenyl-5-trifluoromethyl-1H-pyrazole-4-carbonyl)-5,6,7,8-tetrahydro-pyrido[3,4-d]pyrimidin-4-yl]-acetamide;
2-Adamantan-1-yl-N-[7-(2-methyl-5-phenyl-furan-3-carbonyl)-5,6,7,8-tetrahydro-pyrido[3,4-d]pyrimidin-4-yl]-acetamide;
2-Adamantan-1-yl-N-[7-(5-methyl-1-phenyl-1H-pyrazole-4-carbonyl)-5,6,7,8-tetrahydro-pyrido[3,4-d]pyrimidin-4-yl]-acetamide;
2-Adamantan-1-yl-N-{7-[5-(4-chloro-phenyl)-2-methyl-furan-3-carbonyl]-5,6,7,8-tetrahydro-pyrido[3,4-d]pyrimidin-4-yl}-acetamide;
2-Adamantan-1-yl-N-[7-(naphthalene-2-carbonyl)-5,6,7,8-tetrahydro-pyrido[3,4-d]pyrimidin-4-yl]-acetamide;
2-Adamantan-1-yl-N-[7-(4-methyl-benzoyl)-5,6,7,8-tetrahydro-pyrido[3,4-d]pyrimidin-4-yl]-acetamide;
2-Adamantan-1-yl-N-[7-(2-methoxy-benzoyl)-5,6,7,8-tetrahydro-pyrido[3,4-d]pyrimidin-4-yl]-acetamide;
2-Adamantan-1-yl-N-[7-(2,5-dimethyl-furan-3-carbonyl)-5,6,7,8-tetrahydro-pyrido[3,4-d]pyrimidin-4-yl]-acetamide:
2-Adamantan-1-yl-N-[7-(2-chloro-benzoyl)-5,6,7,8-tetrahydro-pyrido[3,4-d]pyrimidin-4-yl]-acetamide;
N-[7-(1-Acetyl-piperidine-4-carbonyl)-5,6,7,8-tetrahydro-pyrido[3,4-d]pyrimidin-4-yl]-2-adamantan-1-yl-acetamide;
2-Adamantan-1-yl-N-[7-(isoxazole-5-carbonyl)-5,6,7,8-tetrahydro-pyrido[3,4-d]pyrimidin-4-yl]-acetamide;
2-Adamantan-1-yl-N-[7-(3,5-dimethyl-isoxazole-4-carbonyl)-5,6,7,8-tetrahydro-pyrido[3,4-d]pyrimidin-4-yl]-acetamide;
2-Adamantan-1-yl-N-[7-(2-chloro-pyridine-4-carbonyl)-5,6,7,8-tetrahydro-pyrido[3,4-d]pyrimidin-4-yl]-acetamide;
2-Adamantan-1-yl-N-[7-(5-methyl-isoxazole-4-carbonyl)-5,6,7,8-tetrahydro-pyrido[3,4-d]pyrimidin-4-yl]-acetamide;
2-Adamantan-1-yl-N-[7-(2-tert-butyl-5-methyl-2H-pyrazole-3-carbonyl)-5,6,7,8-tetrahydro-pyrido[3,4-d]pyrimidin-4-yl]-acetamide;
2-Adamantan-1-yl-N-[7-(4-tert-butyl-benzoyl)-5,6,7,8-tetrahydro-pyrido[3,4-d]pyrimidin-4-yl]-acetamide;
2-Adamantan-1-yl-N-{7-[2-(2-bromo-phenyl)-acetyl]-5,6,7,8-tetrahydro-pyrido[3,4-d]pyrimidin-4-yl}-acetamide;
2-Adamantan-1-yl-N-[7-(quinoline-2-carbonyl)-5,6,7,8-tetrahydro-pyrido[3,4-d]pyrimidin-4-yl]-acetamide;
2-Adamantan-1-yl-N-[7-(pyridine-4-carbonyl)-5,6,7,8-tetrahydro-pyrido[3,4-d]pyrimidin-4-yl]-acetamide;
2-Adamantan-1-yl-N-[7-(pyridine-2-carbonyl)-5,6,7,8-tetrahydro-pyrido[3,4-d]pyrimidin-4-yl]-acetamide;
2-Adamantan-1-yl-N-{7-[1-(2,2,2-trifluoro-acetyl)-pyrrolidine-2-carbonyl]-5,6,7,8-tetrahydro-pyrido[3,4-d]pyrimidin-4-yl}-acetamide;
2-Adamantan-1-yl-N-[7-(3-methoxy-propionyl)-5,6,7,8-tetrahydro-pyrido[3,4-d]pyrimidin-4-yl]-acetamide;
2-Adamantan-1-yl-N-[7-(pyrazine-2-carbonyl)-5,6,7,8-tetrahydro-pyrido[3,4-d]pyrimidin-4-yl]-acetamide;
2-Adamantan-1-yl-N-[7-(2,3-dihydro-benzofuran-5-carbonyl)-5,6,7,8-tetrahydro-pyrido[3,4-d]pyrimidin-4-yl]-acetamide;
2-Adamantan-1-yl-N-[7-(3-fluoro-4-methoxy-benzoyl)-5,6,7,8-tetrahydro-pyrido[3,4-d]pyrimidin-4-yl]-acetamide;
2-Adamantan-1-yl-N-[7-(quinoxaline-6-carbonyl)-5,6,7,8-tetrahydro-pyrido[3,4-d]pyrimidin-4-yl]-acetamide;
2-Adamantan-1-yl-N-[7-(3,4-dimethoxy-benzoyl)-5,6,7,8-tetrahydro-pyrido[3-4-d]pyrimidin-4-yl]-acetamide;
2-Adamantan-1-yl-N-[7-(chroman-3-carbonyl)-5,6,7,8-tetrahydro-pyrido[3,4-d]pyrimidin-4-yl]-acetamide;
2-Adamantan-1-yl-N-[7-(2-chloro-5-fluoro-benzoyl)-5,6,7,8-tetrahydro-pyrido[3,4-d]pyrimidin-4-yl]-acetamide;
2-Adamantan-1-yl-N-[7-(3,5-dichloro-benzoyl)-5,6,7,8-tetrahydro-pyrido[3,4-d]pyrimidin-4-yl]-acetamide;
2-Adamantan-1-yl-N-{7-[1-(2,3-dihydro-benzo[1,4]diaxin-6-yl)-ethyl]-5,6,7,8-tetrahydro-pyrido[3,4-d]pyrimidin-4-yl}-acetamide;
2-Adamantan-1-yl-N-[7-(9H-fluoren-2-ylmethyl)-5,6,7,8-tetrahydro-pyrido[3,4-d]pyrimidin-4-yl]-acetamide;
2-Adamantan-1-yl-N-[7-(2,4-dichloro-benzyl)-5,6,7,8-tetrahydro-pyrido[3,4-d]pyrimidin-4-yl]-acetamide;
2-Adamantan-1-yl-N-[7-(2,4-dimethyl-benzyl)-5,6,7,8-tetrahydro-pyrido[3,4-d]pyrimidin-4-yl]-acetamide;
2-Adamantan-1-yl-N-(7-benzo[1,3]dioxol-5-ylmethyl-5,6,7,8-tetrahydro-pyrido[3,4-d]pyrimidin-4-yl)-acetamide;
2-Adamantan-1-yl-N-[7-(3,4-difluoro-benzyl)-5,6,7,8-tetrahydro-pyrido[3,4-d]pyrimidin-4-yl]-acetamide;
2-Adamantan-1-yl-N-[7-(3-chloro-4-fluoro-benzyl)-5,6,7,8-tetrahydro-pyrido[3,4-d]pyrimidin-4-yl]-acetamide;
2-Adamantan-1-yl-N-[7-(3-chloro-4-methoxy-benzyl)-5,6,7,8-tetrahydro-pyrido[3,4-d]pyrimidin-4-yl]-acetamide;
2-Adamantan-1-yl-N-[7-(4-chloro-3-trifluoromethyl-benzyl)-5,6,7,8-tetrahydro-pyrido[3,4-d]pyrimidin-4-yl]-acetamide;
2-Adamantan-1-yl-N-[7-(2-chloro-4-fluoro-benzyl)-5,6,7,8-tetrahydro-pyrido[3,4-d]pyrimidin-4-yl]-acetamide;
2-Adamantan-1-yl-N-[7-(2,4-bis-trifluoromethyl-benzyl)-5,6,7,8-tetrahydro-pyrido[3,4-d]pyrimidin-4-yl]-acetamide;
2-Adamantan-1-yl-N-[7-(4-chloro-2-fluoro-benzyl)-5,6,7,8-tetrahydro-pyrido[3,4-d]pyrimidin-4-yl]-acetamide;
2-Adamantan-1-yl-N-[7-(4-chloro-3-fluoro-benzyl)-5,6,7,8-tetrahydro-pyrido[3,4-d]pyrimidin-4-yl]-acetamide;
2-Adamantan-1-yl-N-[7-(4-benzyloxy-2-methoxy-benzyl)-5,6,7,8-tetrahydro-pyrido[3,4-d]pyrimidin-4-yl]-acetamide;
4-{4-[4-(2-Adamantan-1-yl-acetylamino)-5,8-dihydro-6H-pyrido[3,4-d]pyrimidin-7-ylmethyl]-3-methoxy-phenoxy}-butyric acid;
2-Adamantan-1-yl-N-[7-(1H-indol-6-ylmethyl)-5,6,7,8-tetrahydro-pyrido[3,4-d]pyrimidin-4-yl]-acetamide;
2-Adamantan-1-yl-N-[7-(3,4-dihydro-2H-benzo[b][1,4]dioxepin-7-ylmethyl)-5,6,7,8-tetrahydro-pyrido[3,4-d]pyrimidin-4-yl]-acetamide;
Adamantane-1-carboxylic acid (7-benzyl-5,6,7,8-tetrahydro-pyrido[3-4-d]pyrimidin-4-yl)-amide;
2-Adamantan-1-yl-N-(7-benzyl-5,6,7,8-tetrahydro-pyrido[3,4-d]pyrimidin-4-yl)-isobutyramide;
N-(7-Benzyl-5,6,7,8-tetrahydro-pyrido[3,4-d]pyrimidin-4-yl)-2-(3,5-dimethyl-adamantan-1-yl)-acetamide;
N-(7-Benzyl-5,6,7,8-tetrahydro-pyrido[3,4-d]pyrimidin-4-yl)-2-(3,5-dimethyl-adamantan-1-yl)-isobutyramide;
N-(7-Benzyl-5,6,7,8-tetrahydro-pyrido[3,4-d]pyrimidin-4-yl)-2-(3,5,7-trimethyl-adamantan-1-yl)-acetamide;
N-(7-Benzyl-5,6,7,8-tetrahydro-pyrido[3,4-d]pyrimidin-4-yl)-2-(3,5,7-trimethyl-adamantan-1-yl)-isobutyramide;
3,5,7-Trimethyl-adamantane-1-carboxylic acid (7-benzyl-5,6,7,8-tetrahydro-pyrido[3,4-d]pyrimidin-4-yl)-amide;
2-Adamantan-1-yl-N-[7-(2,4-difluoro-benzyl)-5,6,7,8-tetrahydro-pyrido[3,4-d]pyrimidin-4-yl]-isobutyramide;
2-Adamantan-1-yl-N-[7-(2-chloro-benzyl)-5,6,7,8-tetrahydro-pyrido[3,4-d]pyrimidin-4-yl]-isobutyramide;
2-Adamantan-1-yl-N-[7-(2-methyl-benzyl)-5,6,7,8-tetrahydro-pyrido[3,4-d]pyrimidin-4-yl]-isobutyramide;
2-Adamantan-1-yl-N-[7-(2,3-dihydro-benzo[1,4]dioxin-6-ylmethyl)-5,6,7,8-tetrahydro-pyrido[3,4-d]pyrimidin-4-yl]-isobutyramide; |

| Name |
|---|
| 2-Adamantan-1-yl-N-[7-(1H-indol-6-ylmethyl)-5,6,7,8-tetrahydro-pyrido[3,4-d]pyrimidin-4-yl]-isobutyramide;
2-Adamantan-1-yl-N-[7-(4-fluoro-benzyl)-5,6,7,8-tetrahydro-pyrido[3,4-d]pyrimidin-4-yl]-isobutyramide;
2-Adamantan-1-yl-N-(7-phenylmethanesulfonyl-5,6,7,8-tetrahydro-pyrido[3,4-d]pyrimidin-4-yl)-isobutyl-amide;
2-Adamantan-1-yl-N-[7-(3-chloro-benzenesulfonyl)-5,6,7,8-tetrahydro-pyrido[3,4-d]pyrimidin-4-yl]-isobutyramide;
2-Adamantan-1-yl-N-[7-(3,4-difluoro-benzenesulfonyl)-5,6,7,8-tetrahydro-pyrido[3,4-d]pyrimidin-4-yl]-isobutyramide;
2-Adamantan-1-yl-N-[7-(3,4-dichloro-phenylmethanesulfonyl)-5,6,7,8-tetrahydro-pyrido[3,4-d]pyrimidin-4-yl]-isobutyramide;
2-Adamantan-1-yl-N-[7-(4-chloro-phenylmethanesulfonyl)-5,6,7,8-tetrahydro-pyrido[3,4-d]pyrimidin-4-yl]-isobutyramide;
2-Adamantan-1-yl-N-[7-(3-methyl-benzoyl)-5,6,7,8-tetrahydro-pyrido[3,4-d]pyrimidin-4-yl]-isobutyl-amide;
2-Adamantan-1-yl-N-[7-(3-trifluoromethyl-benzoyl)-5,6,7,8-tetrahydro-pyrido[3,4-d]pyrimidin-4-yl]-isobutyramide;
2-Adamantan-1-yl-N-[7-(3,4-dichloro-benzoyl)-5,6,7,8-tetrahydro-pyrido[3,4-d]pyrimidin-4-yl]-isobutyramide;
2-Adamantan-1-yl-N-[7-(2,6-difluoro-benzoyl)-5,6,7,8-tetrahydro-pyrido[3,4-d]pyrimidin-4-yl]-isobutyramide;
2-Adamantan-1-yl-N-[7-(2-chloro-6-fluoro-benzoyl)-5,6,7,8-tetrahydro-pyrido[3,4-d]pyrimidin-4-yl]-isobutyramide;
2-Adamantan-1-yl-N-[7-(2,5-difluoro-benzoyl)-5,6,7,8-tetrahydro-pyrido[3,4-d]pyrimidin-4-yl]-isobutyramide;
2-Adamantan-1-yl-N-[7-(2,3-dichloro-benzoyl)-5,6,7,8-tetrahydro-pyrido[3,4-d]pyrimidin-4-yl]-isobutyramide;
2-Adamantan-1-yl-N-[7-(2-cyclopentyl-acetyl)-5,6,7,8-tetrahydro-pyrido[3,4-d]pyrimidin-4-yl]-isobutyramide;
2-Adamantan-1-yl-N-(7-cyclohexanecarbonyl-5,6,7,8-tetrahydro-pyrido[3,4-d]pyrimidin-4-yl)-isobutyramide;
2-Adamantan-1-yl-N-[7-(3,3-dimethyl-butyryl)-5,6,7,8-tetrahydro-pyrido[3,4-d]pyrimidin-4-yl]-isobutyramide;
2-Adamantan-1-yl-N-[7-(2-fluoro-benzyl)-5,6,7,8-tetrahydro-pyrido[3,4-d]pyrimidin-4-yl]-isobutyramide;
N-[7-(2-Chloro-benzyl)-5,6,7,8-tetrahydro-pyrido[3,4-d]pyrimidin-4-yl]-2-(3,5-dimethyl-adamantan-1-yl)-acetamide;
2-(3,5-Dimethyl-adamantan-1-yl)-N-[7-(2-fluoro-benzyl)-5,6,7,8-tetrahydro-pyrido[3,4-d]pyrimidin-4-yl]-acetamide;
2-(3,5-Dimethyl-adamantan-1-yl)-N-[7-(2-methyl-benzyl)-5,6,7,8-tetrahydro-pyrido[3,4-d]pyrimidin-4-yl]-acetamide;
N-[7-(2,3-Dihydro-benzo[1,4]dioxin-6-ylmethyl)-5,6,7,8-tetrahydro-pyrido[3,4-d]pyrimidin-4-yl]-2-(3,5-dimethyl-adamantan-1-yl)-acetamide;
N-[7-(2-4-Difluoro-benzyl)-5,6,7,8-tetrahydro-pyrido[3,4-d]pyrimidin-4-yl]-2-(3,5-dimethyl-adamantan-1-yl)-acetamide;
2-(3,5-Dimethyl-adamantan-1-yl)-N-[7-(1H-indol-6-ylmethyl)-5,6,7,8-tetrahydro-pyrido[3,4-d]pyrimidin-4-yl]-acetamide;
2-(3,5-Dimethyl-adamantan-1-yl)-N-[7-(4-fluoro-benzyl)-5,6,7,8-tetrahydro-pyridol[3,4-d]pyrimidin-4-yl]-acetamide;
2-(3,5-Dimethyl-adamantan-1-yl)-N-(7-phenylmethanesulfonyl-5,6,7,8-tetrahydro-pyrido[3,4-d]pyrimidin-4-yl)-acetamide;
N-[7-(3,4-Dichloro-phenylmethanesulfonyl)-5,6,7,8-tetrahydro-pyrido[3,4-d]pyrimidin-4-yl]-2-(3,5-dimethyl-adamantan-1-yl)-acetamide;
N-[7-(4-Chloro-phenylmethanesulfonyl)-5,6,7,8-tetrahydro-pyrido[3,4-d]pyrimidin-4-yl]-2-(3,5-dimethyl-adamantan-1-yl)-acetamide;
N-[7-(3-Chloro-benzenesulfonyl)-5,6,7,8-tetrahydro-pyrido[3,4-d]pyrimidin-4-yl]-2-(3,5-dimethyl-adamantan-1-yl)-acetamide;
N-[7-(2,3-Difluoro-benzenesulfonyl)-5,6,7,8-tetrahydro-pyrido[3,4-d]pyrimidin-4-yl]-2-(3,5-dimethyl-adamantan-1-yl)-acetamide;
2-(3,5-Dimethyl-adamantan-1-yl)-N-[7-(3-methyl-benzoyl)-5,6,7,8-tetrahydro-pyrido[3,4-d]pyrimidin-4-yl]-acetamide;
2-(3,5-Dimethyl-adamantan-1-yl)-N-[7-(3-trifluoromethyl-benzoyl)-5,6,7,8-tetrahydro-pyrido[3,4-d]pyrimidin-4-yl]-acetamide;
N-[7-(2-Cyclopentyl-acetyl)-5,6,7,8-tetrahydro-pyrido[3,4-d]pyrimidin-4-yl]-2-(3,5-dimethyl-adamantan-1-yl)-acetamide;
N-[7-(3,4-Dichloro-benzoyl)-5,6,7,8-tetrahydro-pyrido[3,4-d]pyrimidin-4-yl]-2-(3,5-dimethyl-adamantan-1-yl)-acetamide;
N-(7-Cyclohexanecarbonyl-5,6,7,8-tetrahydro-pyrido[3,4-d]pyrimidin-4-yl)-2-(3,5-dimethyl-adamantan-1-yl)-acetamide;
N-[7-(2,6-Difluoro-benzoyl)-5,6,7,8-tetrahydro-pyrido[3,4-d]pyrimidin-4-yl]-2-(3,5-dimethyl-adamantan-1-yl)-acetamide;
2-(3,5-Dimethyl-adamantan-1-yl)-N-[7-(3,3-dimethyl-butyryl)-5,6,7,8-tetrahydro-pyrido[3,4-d]pyrimidin-4-yl]-acetamide;
N-[7-(2-Chloro-6-fluoro-benzoyl)-5,6,7,8-tetrahydro-pyrido[3,4-d]pyrimidin-4-yl]-2-(3,5-dimethyl-adamantan-1-yl)-acetamide;
N-[7-(2,5-Difluoro-benzoyl)-5,6,7,8-tetrahydro-pyrido[3-4-d]pyrimidin-4-yl]-2-(3,5-dimethyl-adamantan-1-yl)-acetamide;
N-[7-(2,3-Dichloro-benzoyl)-5,6,7,8-tetrahydro-pyrido[3,4-d]pyrimidin-4-yl]-2-(3,5-dimethyl-adamantan-1-yl)-acetamide;
Adamantane-1-carboxylic acid [7-(2,6-dichloro-benzoyl)-5,6,7,8-tetrahydro-pyrido[3,4-d]pyrimidin-4-yl]-amide;
Adamantane-1-carboxylic acid (7-acetyl-5,6,7,8-tetrahydro-pyrido[3-4-d]pyrimidin-4-yl)-amide;
Adamantane-1-carboxylic acid (7-benzoyl-5,6,7,8-tetrahydro-pyrido[3,4-d]pyrimidin-4-yl)-amide;
Adamantane-1-carboxylic acid [7-(2-chloro-pyridine-3-carbonyl)-5,6,7,8-tetrahydro-pyrido[3,4-d]pyrimidin-4-yl]-amide;
Adamantane-1-carboxylic acid (7-propionyl-5,6,7,8-tetrahydro-pyrido[3,4-d]pyrimidin-4-yl)-amide;
Adamantane-1-carboxylic acid {7-[2-(4-methoxy-phenyl)-acetyl]-5,6,7,8-tetrahydro-pyrido[3,4-d]pyrimidin-4-yl}-amide;
Adamantane-1-carboxylic acid (7-phenylacetyl-5,6,7,8-tetrahydro-pyrido[3,4-d]pyrimidin-4-yl)-amide;
Adamantane-1-carboxylic acid [7-(4-chloro-benzoyl)-5,6,7,8-tetrahydro-pyrido[3,4-d]pyrimidin-4-yl]-amide;
Adamantane-1-carboxylic acid [7-(3-fluoro-benzoyl)-5,6,7,8-tetrahydro-pyrido[3,4-d]pyrimidin-4-yl]-amide;
Adamantane-1-carboxylic acid [7-(4-trifluoromethoxy-benzoyl)-5,6,7,8-tetrahydro-pyrido[3-4-d]pyrimidin-4-yl]-amide;
Adamantane-1-carboxylic acid [7-(4-ethyl-benzoyl)-5,6,7,8-tetrahydro-pyrido[3,4-d]pyrimidin-4-yl]-amide;
Adamantane-1-carboxylic acid [7-(3-methyl-benzoyl)-5,6,7,8-tetrahydro-pyrido[3,4-d]pyrimidin-4-yl]-amide;
Adamantane-1-carboxylic acid [7-(3-cyclopentyl-propionyl)-5,6,7,8-tetrahydro-pyrido[3,4-d]pyrimidin-4-yl]-amide;
Adamantane-1-carboxylic acid [7-(3,4-difluoro-benzoyl)-5,6,7,8-tetrahydro-pyrido[3,4-d]pyrimidin-4-yl]-amide;
Adamantane-1-carboxylic acid [7-(3-trifluoromethyl-benzoyl)-5,6,7,8-tetrahydro-pyrido[3,4-d]pyrimidin-4-yl]-amide;
Adamantane-1-carboxylic acid [7-(4-methoxy-benzoyl)-5,6,7,8-tetrahydro-pyrido[3,4-d]pyrimidin-4-yl]-amide;
Adamantane-1-carboxylic acid [7-(3,5,5-trimethyl-hexanoyl)-5,6,7,8-tetrahydro-pyrido[3,4-d]pyrimidin-4-yl]-amide;
Adamantane-1-carboxylic acid (7-diphenylacetyl-5,6,7,8-tetrahydro-pyrido[3,4-d]pyrimidin-4-yl)-amide;
Adamantane-1-carboxylic acid (7-cyclopentanecarbonyl-5,6,7,8-tetrahydro-pyrido[3,4-d]pyrimidin-4-yl)-amide;
Adamantane-1-carboxylic acid {7-[2-(2,5-dimethoxy-phenyl)-acetyl]-5,6,7,8-tetrahydro-pyrido[3,4-d]pyrimidin-4-yl}-amide;
Adamantane-1-carboxylic acid [7-(2-methoxy-acetyl)-5,6,7,8-tetrahydro-pyrido[3,4-d]pyrimidin-4-yl]-amide;
Adamantane-1-carboxylic acid {7-[2-(4-fluoro-phenyl)-acetyl]-5,6,7,8-tetrahydro-pyrido[3,4-d]pyrimidin-4-yl}-amide;
Adamantane-1-carboxylic acid [7-(3-cyano-benzoyl)-5,6,7,8-tetrahydro-pyrido[3,4-d]pyrimidin-4-yl]-amide;
Adamantane-1-carboxylic acid [7-(4-trifluoromethyl-benzoyl)-5,6,7,8-tetrahydro-pyrido[3,4-d]pyrimidin-4-yl]-amide;
Adamantane-1-carboxylic acid (7-cyclohexanecarbonyl-5,6,7,8-tetrahydro-pyrido[3,4-d]pyrimidin-4-yl)-amide;
Adamantane-1-carboxylic acid [7-(3,4-dichloro-benzoyl)-5,6,7,8-tetrahydro-pyrido[3,4-d]pyrimidin-4-yl]-amide;
Adamantane-1-carboxylic acid [7-(3,5-dimethoxy-benzoyl)-5,6,7,8-tetrahydro-pyrido[3,4-d]pyrimidin-4-yl]-amide;
Adamantane-1-carboxylic acid [7-(2,6-difluoro-benzoyl)-5,6,7,8-tetrahydro-pyrido[3,4-d]pyrimidin-4-yl]-amide;
Adamantane-1-carboxylic acid [7-(3-phenyl-propionyl)-5,6,7,8-tetrahydro-pyrido[3,4-d]pyrimidin-4-yl]-amide;
Adamantane-1-carboxylic acid [7-(2-phenoxy-acetyl)-5,6,7,8-tetrahydro-pyrido[3,4-d]pyrimidin-4-yl]-amide;
Adamantane-1-carboxylic acid [7-(3-methoxy-benzoyl)-5,6,7,8-tetrahydro-pyrido[3,4-d]pyrimidin-4-yl]-amide;
Adamantane-1-carboxylic acid [7-(4-fluoro-benzoyl)-5,6,7,8-tetrahydro-pyrido[3,4-d]pyrimidin-4-yl]-amide;
Adamantane-1-carboxylic acid [7-(2,2-dimethyl-propionyl)-5,6,7,8-tetrahydro-pyrido[3,4-d]pyrimidin-4-yl]-amide;
Adamantane-1-carboxylic acid [7-(3-chloro-benzoyl)-5,6,7,8-tetrahydro-pyrido[3,4-d]pyrimidin-4-yl]-amide;
Adamantane-1-carboxylic acid {7{2-(3-4-dimethoxy-phenyl)-acetyl]-5,6,7,8-tetrahydro-pyrido[3,4-d]pyrimidin-4-yl}-amide; |

| Name |
|---|
| Adamantane-1-carboxylic acid [7-(3-methyl-butyryl)-5,6,7,8-tetrahydro-pyrido[3,4-d]pyrimidin-4-yl]-amide;
Adamantane-1-carboxylic acid [7-(2-benzyloxy-acetyl)-5,6,7,8-tetrahydro-pyrido[3,4-d]pyrimidin-4-yl]-amide;
Adamantane-1-carboxylic acid [7-(4-cyano-benzoyl)-5,6,7,8-tetrahydro-pyrido[3,4-d]pyrimidin-4-yl]-amide;
Adamantane-1-carboxylic acid [7-(2,4-dichloro-benzoyl)-5,6,7,8-tetrahydro-pyrido[3,4-d]pyrimidin-4-yl]-amide;
Adamantane-1-carboxylic acid [7-(quinoxaline-2-carbonyl)-5,6,7,8-tetrahydro-pyrido[3,4-d]pyrimidin-4-yl]-amide;
Adamantane-1-carboxylic acid (7-cyclopropanecarbonyl-5,6,7,8-tetrahydro-pyrido[3,4-d]pyrimidin-4-yl)-amide;
Adamantane-1-carboxylic acid {7-[2-(3-methoxy-phenyl)-acetyl]-5,6,7,8-tetrahydro-pyrido[3,4-d]pyrimidin-4-yl}-amide;
Adamantane-1-carboxylic acid [7-(3,3-dimethyl-butyryl)-5,6,7,8-tetrahydro-pyrido[3,4-d]pyrimidin-4-yl]-amide;
Adamantane-1-carboxylic acid [7-(2-cyclopentyl-acetyl)-5,6,7,8-tetrahydro-pyrido[3,4-d]pyrimidin-4-yl]-amide;
Adamantane-1-carboxylic acid {7-[2-(4-chloro-phenoxy)-acetyl]-5,6,7,8-tetrahydro-pyrido[3,4-d]pyrimidin-4-yl}-amide;
Adamantane-1-carboxylic acid {7-[2-(4-chloro-phenyl)-acetyl]-5,6,7,8-tetrahydro-pyrido[3,4-d]pyrimidin-4-yl}-amide;
Adamantane-1-carboxylic acid [7-(2-fluoro-4-trifluoromethyl-benzoyl)-5,6,7,8-tetrahydro-pyrido[3,4-d]pyrimidin-4-yl]-amide;
Adamantane-1-carboxylic acid [7-(3-fluoro-5-trifluoromethyl-benzoyl)-5,6,7,8-tetrahydro-pyrido[3,4-d]pyrimidin-4-yl]-amide;
Adamantane-1-carboxylic acid [7-(2-trifluoromethoxy-benzoyl)-5,6,7,8-tetrahydro-pyrido[3,4-d]pyrimidin-4-yl]-amide;
Adamantane-1-carboxylic acid [7-(3-trifluoromethoxy-benzoyl)-5,6,7,8-tetrahydro-pyrido[3,4-d]pyrimidin-4-yl]-amide;
Adamantane-1-carboxylic acid [7-(2-trifluoromethyl-benzoyl)-5,6,7,8-tetrahydro-pyrido[3,4-d]pyrimidin-4-yl]-amide;
Adamantane-1-carboxylic acid [7-(2-chloro-5-trifluoromethyl-benzoyl)-5,6,7,8-tetrahydro-pyrido[3,4-d]pyrimidin-4-yl]-amide;
Adamantane-1-carboxylic acid [7-(2-chloro-6-fluoro-benzoyl)-5,6,7,8-tetrahydro-pyrido[3,4-d]pyrimidin-4-yl]-amide;
Adamantane-1-carboxylic acid [7-(5-methyl-2-phenyl-2H-[1,2,3]triazole-4-carbonyl)-5,6,7,8-tetrahydro-pyrido[3,4-d]pyrimidin-4-yl]-amide;
Adamantane-1-carboxylic acid [7-(2-phenoxy-pyridine-3-carbonyl)-5,6,7,8-tetrahydro-pyrido[3,4-d]pyrimidin-4-yl]-amide;
Adamantane-1-carboxylic acid [7-(2,4-dimethoxy-benzoyl)-5,6,7,8-tetrahydro-pyrido[3,4-d]pyrimidin-4-yl]-amide;
Adamantane-1-carboxylic acid [7-(2,3-dihydro-benzo[1,4]dioxine-2-carbonyl)-5,6,7,8-tetrahydro-pyrido[3,4-d]pyrimidin-4-yl]-amide;
Adamantane-1-carboxylic acid [7-(2,4-difluoro-benzoyl)-5,6,7,8-tetrahydro-pyrido[3,4-d]pyrimidin-4-yl]-amide;
Adamantane-1-carboxylic acid [7-(2-methyl-benzoyl)-5,6,7,8-tetrahydro-pyrido[3,4-d]pyrimidin-4-yl]-amide;
Adamantane-1-carboxylic acid [7-(2,5-difluoro-benzoyl)-5,6,7,8-tetrahydro-pyridol[3,4-d]pyrimidin-4-yl]-amide;
Adamantane-1-carboxylic acid [7-(2-fluoro-benzoyl)-5,6,7,8-tetrahydro-pyrido[3,4-d]pyrimidin-4-yl]-amide;
Adamantane-1-carboxylic acid [7-(6-chloro-pyridine-3-carbonyl)-5,6,7,8-tetrahydro-pyrido[3,4-d]pyrimidin-4-yl]-amide;
Adamantane-1-carboxylic acid [7-(2,3-dichloro-benzoyl)-5,6,7,8-tetrahydro-pyrido[3,4-d]pyrimidin-4-yl]-amide;
Adamantane-1-carboxylic acid [7-(5-methyl-isoxazole-3-carbonyl)-5,6,7,8-tetrahydro-pyrido[3,4-d]pyrimidin-4-yl]-amide;
Adamantane-1-carboxylic acid [7-(1,5-dimethyl-1H-pyrazole-3-carbonyl)-5,6,7,8-tetrahydro-pyrido[3,4-d]pyrimidin-4-yl]-amide;
Adamantane-1-carboxylic acid [7-(2-methyl-5-phenyl-furan-3-carbonyl)-5,6,7,8-tetrahydro-pyrido[3,4-d]pyrimidin-4-yl]-amide;
Adamantane-1-carboxylic acid [7-(5-methyl-1-phenyl-1H-pyrazole-4-carbonyl)-5,6,7,8-tetrahydro-pyrido[3,4-d]pyrimidin-4-yl]-amide;
Adamantane-1-carboxylic acid {7-[5-(4-chloro-phenyl)-2-methyl-furan-3-carbonyl]-5,6,7,8-tetrahydro-pyrido[3,4-d]pyrimidin-4-yl}-amide;
Adamantane-1-carboxylic acid [7-(naphthalene-2-carbonyl)-5,6,7,8-tetrahydro-pyrido[3,4-d]pyrimidin-4-yl]-amide;
Adamantane-1-carboxylic acid [7-(4-methyl-benzoyl)-5,6,7,8-tetrahydro-pyrido[3,4-d]pyrimidin-4-yl]-amide;
Adamantane-1-carboxylic acid [7-(2-methoxy-benzoyl)-5,6,7,8-tetrahydro-pyrido[3,4-d]pyrimidin-4-yl]-amide;
Adamantane-1-carboxylic acid [7-(2,5-dimethyl-furan-3-carbonyl)-5,6,7,8-tetrahydro-pyrido[3,4-d]pyrimidin-4-yl]-amide;
Adamantane-1-carboxylic acid [7-(2-chloro-benzoyl)-5,6,7,8-tetrahydro-pyrido[3,4-d]pyrimidin-4-yl]-amide;
Adamantane-1-carboxylic acid [7-(1-acetyl-piperidine-4-carbonyl)-5,6,7,8-tetrahydro-pyrido[3,4-d]pyrimidin-4-yl]-amide;
Adamantane-1-carboxylic acid [7-(isoxazole-5-carbonyl)-5,6,7,8-tetrahydro-pyrido[3,4-d]pyrimidin-4-yl]-amide;
Adamantane-1-carboxylic acid [7-(2-chloro-pyridine-4-carbonyl)-5,6,7,8-tetrahydro-pyrido[3,4-d]pyrimidin-4-yl]-amide;
Adamantane-1-carboxylic acid [7-(2-tert-butyl-5-methyl-2H-pyrazole-3-carbonyl)-5,6,7,8-tetrahydro-pyrido[3,4-d]pyrimidin-4-yl]-amide;
Adamantane-1-carboxylic acid [7-(4-tert-butyl-benzoyl)-5,6,7,8-tetrahydro-pyrido[3,4-d]pyrimidin-4-yl]-amide
Adamantane-1-carboxylic acid {7-[2-(2-bromo-phenyl)-acetyl]-5,6,7,8-tetrahydro-pyrido[3,4-d]pyrimidin-4-yl}-amide;
Adamantane-1-carboxylic acid [7-(quinoline-2-carbonyl)-5,6,7,8-tetrahydro-pyrido[3,4-d]pyrimidin-4-yl]-amide;
Adamantane-1-carboxylic acid {7-[1-(2,2,2-trifluoro-acetyl)-pyrrolidine-2-carbonyl]-5,6,7,8-tetrahydro-pyrido[3,4-d]pyrimidin-4-yl}-amide;
Adamantane-1-carboxylic acid [7-(pyrazine-2-carbonyl)-5,6,7,8-tetrahydro-pyrido[3,4-d]pyrimidin-4-yl]-amide;
Adamantane-1-carboxylic acid [7-(2,3-dihydro-benzofuran-5-carbonyl)-5,6,7,8-tetrahydro-pyrido[3,4-d]pyrimidin-4-yl]-amide;
Adamantane-1-carboxylic acid [7-(3-fluoro-4-methoxy-benzoyl)-5,6,7,8-tetrahydro-pyrido[3,4-d]pyrimidin-4-yl]-amide;
Adamantane-1-carboxylic acid 7-(3,4-dimethoxy-benzoyl)-5,6,7,8-tetrahydro-pyrido[3,4-d]pyrimidin-4-yl]-amide;
Adamantane-1-carboxylic acid [7-(chroman-3-carbonyl)-5,6,7,8-tetrahydro-pyrido[3,4-d]pyrimidin-4-yl]-amide;
Adamantane-1-carboxylic acid [7-(2-chloro-5-fluoro-benzoyl)-5,6,7,8-tetrahydro-pyrido[3,4-d]pyrimidin-4-yl]-amide;
Adamantane-1-carboxylic acid [7-(3,5-dichloro-benzoyl)-5,6,7,8-tetrahydro-pyrido[3,4-d]pyrimidin-4-yl]-amide;
Adamantane-1-carboxylic acid (7-methanesulfonyl-5,6,7,8-tetrahydro-pyrido[3,4-d]pyrimidin-4-yl)-amide;
Adamantane-1-carboxylic acid (7-benzenesulfonyl-5,6,7,8-tetrahydro-pyrido[3,4-d]pyrimidin-4-yl)-amide;
Adamantane-1-carboxylic acid [7-(toluene-4-sulfonyl)-5,6,7,8-tetrahydro-pyrido[3,4-d]pyrimidin-4-yl]-amide;
Adamantane-1-carboxylic acid [7-(naphthalene-2-sulfonyl)-5,6,7,8-tetrahydro-pyrido[3,4-d]pyrimidin-4-yl]-amide;
Adamantane-1-carboxylic acid [7-(quinoline-8-sulfonyl)-5,6,7,8-tetrahydro-pyrido[3,4-d]pyrimidin-4-yl]-amide;
Adamantane-1-carboxylic acid [7-(propane-1-sulfonyl)-5,6,7,8-tetrahydro-pyrido[3,4-d]pyrimidin-4-yl]-amide;
Adamantane-1-carboxylic acid (7-ethanesulfonyl-5,6,7,8-tetrahydro-pyrido[3,4-d]pyrimidin-4-yl)-amide;
Adamantane-1-carboxylic acid [7-(4-methoxy-benzenesulfonyl)-5,6,7,8-tetrahydro-pyrido[3,4-d]pyrimidin-4-yl]-amide;
Adamantane-1-carboxylic acid [7-(4-chloro-benzenesulfonyl)-5,6,7,8-tetrahydro-pyrido[3,4-d]pyrimidin-4-yl]-amide;
Adamantane-1-carboxylic acid [7-(3,4-dimethoxy-benzenesulfonyl)-5,6,7,8-tetrahydro-pyrido[3,4-d]pyrimidin-4-yl]-amide:
Adamantane-1-carboxylic acid [7-(4-fluoro-benzenesulfonyl)-5,6,7,8-tetrahydro-pyrido[3,4-d]pyrimidin-4-yl]-amide;
Adamantane-1-carboxylic acid (7-phenylmethanesulfonyl-5,6,7,8-tetrahydro-pyrido[3,4-d]pyrimidin-4-yl)-amide;
Adamantane-1-carboxylic acid [7-(3-trifluoromethyl-benzenesulfonyl)-5,6,7,8-tetrahydro-pyrido[3,4-d]pyrimidin-4-yl]-amide;
Adamantane-1-carboxylic acid [7-(4-trifluoromethoxy-benzenesulfonyl)-5,6,7,8-tetrahydro-pyrido[3,4-d]pyrimidin-4-yl]-amide;
Adamantane-1-carboxylic acid [7-(4-methyl-3,4-dihydro-2H-benzo[1,4]oxazine-7-sulfonyl)-5,6,7,8-tetrahydro-pyrido[3,4-d]pyrimidin-4-yl]-amide;
Adamantane-1-carboxylic acid [7-(5-chloro-1,3-dimethyl-1H-pyrazole-4-sulfonyl)-5,6,7,8-tetrahydro-pyrido[3,4-d]pyrimidin-4-yl]-amide;
Adamantane-1-carboxylic acid [7-(5-methyl-1-phenyl-1H-pyrazole-4-sulfonyl)-5,6,7,8-tetrahydro-pyrido[3,4-d]pyrimidin-4-yl]-amide;
Adamantane-1-carboxylic acid [7-(3-trifluoromethoxy-benzenesulfonyl)-5,6,7,8-tetrahydro-pyrido[3,4-d]pyrimidin-4-yl]-amide;
Adamantane-1-carboxylic acid [7-(3-methoxy-benzenesulfonyl)-5,6,7,8-tetrahydro-pyrido[3,4-d]pyrimidin-4-yl]-amide; |

| Name |
|---|
| Adamantane-1-carboxylic acid [7-(1,2-dimethyl-1H-imidazole-4-sulfonyl)-5,6,7,8-tetrahydro-pyrido[3,4-d]pyrimidin-4-yl]-amide;
Adamantane-1-carboxylic acid [7-(2-chloro-4-cyano-benzenesulfonyl)-5,6,7,8-tetrahydro-pyrido[3,4-d]pyrimidin-4-yl]-amide;
Adamantane-1-carboxylic acid [7-(2-fluoro-benzenesulfonyl)-5,6,7,8-tetrahydro-pyrido[3,4-d]pyrimidin-4-yl]-amide;
Adamantane-1-carboxylic acid [7-(4-cyano-benzenesulfonyl)-5,6,7,8-tetrahydro-pyrido[3,4-d]pyrimidin-4-yl]-amide;
Adamantane-1-carboxylic acid [7-(3,5-dimethyl-isoxazole-4-sulfonyl)-5,6,7,8-tetrahydro-pyrido[3,4-d]pyrimidin-4-yl]-amide;
Adamantane-1-carboxylic acid (7-methanesulfonylmethanesulfonyl-5,6,7,8-tetrahydro-pyrido[3,4-d]pyrimidin-4-yl)-amide;
Adamantane-1-carboxylic acid [7-(2-oxo-2H-chromene-6-sulfonyl)-5,6,7,8-tetrahydro-pyrido[3,4-d]pyrimidin-4-yl]-amide;
Adamantane-1-carboxylic acid {7-[4-(pyridin-2-yloxy)-benzenesulfonyl]-5,6,7,8-tetrahydro-pyrido[3,4-d]pyrimidin-4-yl}-amide;
Adamantane-1-carboxylic acid {7-[4-(pyridin-3-yloxy)-benzenesulfonyl]-5,6,7,8-tetrahydro-pyrido[3,4-d]pyrimidin-4-yl}-amide;
Adamantane-1-carboxylic acid {7-[4-(pyridin-4-yloxy)-benzenesulfonyl]-5,6,7,8-tetrahydro-pyrido[3,4-d]pyrimidin-4-yl}-amide;
Adamantane-1-carboxylic acid {7-[4-{4-methoxy-phenoxy)-benzenesulfonyl]-5,6,7,8-tetrahydro-pyrido[3,4-d]pyrimidin-4-yl}-amide;
Adamantane-1-carboxylic acid {7-[4-(4-trifluoromethyl-phenoxy)-benzenesulfonyl]-5,6,7,8-tetrahydro-pyrido[3,4-d]pyrimidin-4-yl}-amide;
Adamantane-1-carboxylic acid {7-[3-(3,4-dichloro-phenoxy)-benzenesulfonyl]-5,6,7,8-tetrahydro-pyrido[3,4-d]pyrimidin-4-yl}-amide;
Adamantane-1-carboxylic acid [7-(4[40 -methoxy-biphenyl-4-sulfonyl)-5,6,7,8-tetrahydro-pyrido[3,4-d]pyrimidin-4-yl]-amide;
Adamantane-1-carboxylic acid [7-(pyridine-3-sulfonyl)-5,6,7,8-tetrahydro-pyrido[3,4-d]pyrimidin-4-yl]-amide;
Adamantane-1-carboxylic acid [7-(2-chloro-5-trifluoromethyl-benzenesulfonyl)-5,6,7,8-tetrahydro-pyrido[3,4-d]pyrimidin-4-yl]-amide;
Adamantane-1-carboxylic acid [7-(3,5-bis-trifluoromethyl-phenylmethanesulfonyl)-5,6,7,8-tetrahydro-pyrido[3,4-d]pyrimidin-4-yl]-amide;
Adamantane-1-carboxylic acid [7-(4-trifluoromethyl-phenylmethanesulfonyl)-5,6,7,8-tetrahydro-pyrido[3,4-d]pyrimidin-4-yl]-amide;
Adamantane-1-carboxylic acid [7-(4-fluoro-phenylmethanesulfonyl)-5,6,7,8-tetrahydro-pyrido[3,4-d]pyrimidin-4-yl]-amide;
Adamantane-1-carboxylic acid [7-(3,4-dichloro-phenylmethanesulfonyl)-5,6,7,8-tetrahydro-pyrido[3,4-d]pyrimidin-4-yl]-amide;
Adamantane-1-carboxylic acid [7-(3,5-dichloro-phenylmethanesulfonyl)-5,6,7,8-tetrahydro-pyrido[3,4-d]pyrimidin-4-yl]-amide;
Adamantane-1-carboxylic acid [7-(3-trifluoromethyl-phenylmethanesulfonyl)-5,6,7,8-tetrahydro-pyrido[3,4-d]pyrimidin-4-yl]-amide;
Adamantane-1-carboxylic acid (7-p-tolylmethanesulfonyl-5,6,7,8-tetrahydro-pyrido[3,4-d]pyrimidin-4-yl)-amide;
Adamantane-1-carboxylic acid [7-(4-chloro-phenylmethanesulfonyl)-5,6,7,8-tetrahydro-pyrido[3-4-d]pyrimidin-4-yl]-amide;
Adamantane-1-carboxylic acid [7-(4-difluoromethoxy-benzenesulfonyl)-5,6,7,8-tetrahydro-pyrido[3,4-d]pyrimidin-4-yl]-amide;
Adamantane-1-carboxylic acid [7-(4-phenoxy-benzenesulfonyl)-5,6,7,8-tetrahydro-pyrido[3,4-d]pyrimidin-4-yl]-amide;
Adamantane-1-carboxylic acid [7-(2-chloro-benzenesulfonyl)-5,6,7,8-tetrahydro-pyrido[3,4-d]pyrimidin-4-yl]-amide;
Adamantane-1-carboxylic acid [7-(3-chloro-4-fluoro-benzenesulfonyl)-5,6,7,8-tetrahydro-pyrido[3,4-d]pyrimidin-4-yl]-amide;
Adamantane-1-carboxylic acid [7-(biphenyl-2-sulfonyl)-5,6,7,8-tetrahydro-pyrido[3,4-d]pyrimidin-4-yl]-amide;
Adamantane-1-carboxylic acid [7-(2-trifluoromethyl-benzenesulfonyl)-5,6,7,8-tetrahydro-pyrido[3,4-d]pyrimidin-4-yl]-amide;
Adamantane-1-carboxylic acid [7-(4-pyrazol-1-yl-benzenesulfonyl)-5,6,7,8-tetrahydro-pyrido[3,4-d]pyrimidin-4-yl]-amide;
Adamantane-1-carboxylic acid [7-(2,4-dimethoxy-benzenesulfonyl)-5,6,7,8-tetrahydro-pyrido[3,4-d]pyrimidin-4-yl]-amide;
Adamantane-1-carboxylic acid [7-(1,3,5-trimethyl-1H-pyrazole-4-sulfonyl)-5,6,7,8-tetrahydro-pyrido[3,4-d]pyrimidin-4-yl]-amide;
Adamantane-1-carboxylic acid [7-(2-trifluoromethoxy-benzenesulfonyl)-5,6,7,8-tetrahydro-pyrido[3,4-d]pyrimidin-4-yl]-amide;
Adamantane-1-carboxylic acid [7-(toluene-2-sulfonyl)-5,6,7,8-tetrahydro-pyrido[3,4-d]pyrimidin-4-yl]-amide;
Adamantane-1-carboxylic acid [7-(2,3-dihydro-benzo[1,4]dioxine-6-sulfonyl)-5,6,7,8-tetrahydro-pyrido[3,4-d]pyrimidin-4-yl]-amide;
Adamantane-1-carboxylic acid [7-(4-trifluoromethyl-benzenesulfonyl)-5,6,7,8-tetrahydro-pyrido[3,4-d]pyrimidin-4-yl]-amide;
Adamantane-1-carboxylic acid [7-(4-chloro-2-fluoro-benzenesulfonyl)-5,6,7,8-tetrahydro-pyrido[3,4-d]pyrimidin-4-yl]-amide;
Adamantane-1-carboxylic acid [7-(2,5-difluoro-benzenesulfonyl)-5,6,7,8-tetrahydro-pyrido[3,4-d]pyrimidin-4-yl]-amide;
Adamantane-1-carboxylic acid [7-(2,5-dichloro-benzenesulfonyl)-5,6,7,8-tetrahydro-pyrido[3,4-d]pyrimidin-4-yl]-amide;
Adamantane-1-carboxylic acid [7-(5-chloro-2-fluoro-benzenesulfonyl)-5,6,7,8-tetrahydro-pyrido[3,4-d]pyrimidin-4-yl]-amide;
Adamantane-1-carboxylic acid [7-(2,6-difluoro-benzenesulfonyl)-5,6,7,8-tetrahydro-pyrido[3,4-d]pyrimidin-4-yl]-amide;
Adamantane-1-carboxylic acid [7-(3-chloro-4-methyl-benzenesulfonyl)-5,6,7,8-tetrahydro-pyrido[3,4-d]pyrimidin-4-yl]-amide;
Adamantane-1-carboxylic acid [7-(3,5-dichloro-benzenesulfonyl)-5,6,7,8-tetrahydro-pyrido[3,4-d]pyrimidin-4-yl]-amide;
Adamantane-1-carboxylic acid [7-(2,4-difluoro-benzenesulfonyl)-5,6,7,8-tetrahydro-pyrido[3,4-d]pyrimidin-4-yl]-amide;
Adamantane-1-carboxylic acid [7-(2,6-dichloro-benzenesulfonyl)-5,6,7,8-tetrahydro-pyrido[3,4-d]pyrimidin-4-yl]-amide;
Adamantane-1-carboxylic acid [7-(2-chloro-4-fluoro-benzenesulfonyl)-5,6,7,8-tetrahydro-pyrido[3,4-d]pyrimidin-4-yl]-amide;
Adamantane-1-carboxylic acid [7-(5-fluoro-2-methyl-benzenesulfonyl)-5,6,7,8-tetrahydro-pyrido[3,4-d]pyrimidin-4-yl]-amide;
Adamantane-1-carboxylic acid [7-(propane-2-sulfonyl)-5,6,7,8-tetrahydro-pyrido[3,4-d]pyrimidin-4-yl]-amide;
Adamantane-1-carboxylic acid [7-(2-methoxy-5-methyl-benzenesulfonyl)-5,6,7,8-tetrahydro-pyrido[3,4-d]pyrimidin-4-yl]-amide;
Adamantane-1-carboxylic acid [7-(2,5-dimethoxy-benzenesulfonyl)-5,6,7,8-tetrahydro-pyrido[3-4-d]pyrimidin-4-yl]-amide;
Adamantane-1-carboxylic acid [7-(3,5-dimethyl-benzenesulfonyl)-5,6,7,8-tetrahydro-pyrido[3,4-d]pyrimidin-4-yl]-amide;
Adamantane-1-carboxylic acid [7-(2-cyano-benzenesulfonyl)-5,6,7,8-tetrahydro-pyrido[3,4-d]pyrimidin-4-yl]-amide;
Adamantane-1-carboxylic acid [7-(3,5,5-trimethyl-hexyl)-5,6,7,8-tetrahydro-pyrido[3,4-d]pyrimidin-4-yl]-amide;
Adamantane-1-carboxylic acid [7-(2,2-diphenyl-ethyl)-5,6,7,8-tetrahydro-pyrido[3,4-d]pyrimidin-4-yl]-amide;
Adamantane-1-carboxylic acid [7-(2-phenyl-propyl)-5,6,7,8-tetrahydro-pyrido[3,4-d]pyrimidin-4-yl]-amide;
Adamantane-1-carboxylic acid (7-propyl-5,6,7,8-tetrahydro-pyrido[3,4-d]pyrimidin-4-yl)-amide;
Adamantane-1-carboxylic acid (7-cyclohexylmethyl-5,6,7,8-tetrahydro-pyrido[3,4-d]pyrimidin-4-yl)-amide;
Adamantane-1-carboxylic acid (7-cyclopropylmethyl-5,6,7,8-tetrahydro-pyrido(3,4-d]pyrimidin-4-yl)-amide;
Adamantane-1-carboxylic acid (7-pentyl-5,6,7,8-tetrahydro-pyrido[3,4-d]pyrimidin-4-yl)-amide;
Adamantane-1-carboxylic acid [7-(3-phenyl-propyl)-5,6,7,8-tetrahydro-pyrido[3,4-d]pyrimidin-4-yl]-amide;
Adamantane-1-carboxylic acid (7-pyridin-3-ylmethyl-5,6,7,8-tetrahydro-pyrido[3,4-d]pyrimidin-4-yl)-amide;
Adamantane-1-carboxylic acid [7-(1-methyl-1H-pyrrol-2-ylmethyl)-5,6,7,8-tetrahydro-pyrido[3,4-d]pyrimidin-4-yl]-amide;
Adamantane-1-carboxylic acid [7-(4-methoxy-benzyl)-5,6,7,8-tetrahydro-pyrido[3,4-d]pyrimidin-4-yl]-amide; |

| Name |
|---|
| Adamantane-1-carboxylic acid [7-(1H-indol-3-ylmethyl)-5,6,7,8-tetrahydro-pyrido[3,4-d]pyrimidin-4-yl]-amide;
Adamantane-1-carboxylic acid (7-benzo[1,3]dioxol-5-ylmethyl-5,6,7,8-tetrahydro-pyrido[3,4-d]pyrimidin-4-yl)-amide;
Adamantane-1-carboxylic acid (7-naphthalen-2-ylmethyl-5,6,7,8-tetrahydro-pyrido[3,4-d]pyrimidin-4-yl)-amide;
Adamantane-1-carboxylic acid [7-(3,4-dimethoxy-benzyl)-5,6,7,8-tetrahydro-pyrido[3,4-d]pyrimidin-4-yl]-amide;
Adamantane-1-carboxylic acid [7-(6-methyl-4-oxo-4H-chromen-3-ylmethyl)-5,6,7,8-tetrahydro-pyrido[3,4-d]pyrimidin-4-yl]-amide;
Adamantane-1-carboxylic acid [7-(3-phenoxy-benzyl)-5,6,7,8-tetrahydro-pyrido[3,4-d]pyrimidin-4-yl]-amide;
Adamantane-1-carboxylic acid [7-(5-bromo-2-methoxy-benzyl)-5,6,7,8-tetrahydro-pyrido[3,4-d]pyrimidin-4-yl]-amide;
Adamantane-1-carboxylic acid [7-(2,4-dichloro-benzyl)-5,6,7,8-tetrahydro-pyrido[3,4-d]pyrimidin-4-yl]-amide;
Adamantane-1-carboxylic acid [7-(3-cyano-benzyl)-5,6,7,8-tetrahydro-pyrido[3,4-d]pyrimidin-4-yl]-amide;
Adamantane-1-carboxylic acid [7-(4-tert-butyl-benzyl)-5,6,7,8-tetrahydro-pyrido(3,4-d]pyrimidin-4-yl]-amide;
Adamantane-1-carboxylic acid [7-(6,6-dimethyl-bicyclo[3.1.1]hept-2-en-2-ylmethyl)-5,6,7,8-tetrahydro-pyrido[3,4-d]pyrimidin-4-yl]-amide;
Adamantane-1-carboxylic acid [7-(3-trifluoromethyl-benzyl)-5,6,7,8-tetrahydro-pyrido[3,4-d]pyrimidin-4-yl]-amide;
Adamantane-1-carboxylic acid [7-(4-dimethylamino-benzyl)-5,6,7,8-tetrahydro-pyrido[3,4-d]pyrimidin-4-yl]-amide;
Adamantane-1-carboxylic acid [7-(4-phenoxy-benzyl)-5,6,7,8-tetrahydro-pyrido[3,4-d]pyrimidin-4-yl]-amide;
Adamantane-1-carboxylic acid [7-(2-chloro-6-fluoro-benzyl)-5,6,7,8-tetrahydro-pyrido[3,4-d]pyrimidin-4-yl]-amide;
Adamantane-1-carboxylic acid (7-butyl-5,6,7,8-tetrahydro-pyrido[3,4-d]pyrimidin-4-yl)-amide;
Adamantane-1-carboxylic acid (7-ethyl-5,6,7,8-tetrahydro-pyrido[3,4-d]pyrimidin-4-yl)-amide;
Adamantane-1-carboxylic acid [7-(1-methyl-1H-indol-3-ylmethyl)-5,6,7,8-tetrahydro-pyrido[3,4-d]pyrimidin-4-yl]-amide;
Adamantane-1-carboxylic acid [7-(2-ethyl-butyl)-5,6,7,8-tetrahydro-pyrido[3,4-d]pyrimidin-4-yl]-amide;
Adamantane-1-carboxylic acid [7-(2-methyl-pentyl)-5,6,7,8-tetrahydro-pyrido[3,4-d]pyrimidin-4-yl]-amide;
Adamantane-1-carboxylic acid [7-(3-methyl-butyl)-5,6,7,8-tetrahydro-pyrido[3,4-d]pyrimidin-4-yl]-amide;
Adamantane-1-carboxylic acid [7-(4-methoxy-benzyl)-5,6,7,8-tetrahydro-pyrido[3,4-d]pyrimidin-4-yl]-amide;
Adamantane-1-carboxylic acid [7-(3,4-dimethyl-benzyl)-5,6,7,8-tetrahydro-pyrido[3,4-d]pyrimidin-4-yl]-amide;
Adamantane-1-carboxylic acid [7-(2-chloro-3,4-dimethoxy-benzyl)-5,6,7,8-tetrahydro-pyrido[3,4-d]pyrimidin-4-yl]-amide;
Adamantane-1-carboxylic acid [7-(6-bromo-benzo[1,3]dioxol-5-ylmethyl)-5,6,7,8-tetrahydro-pyrido[3,4-d]pyrimidin-4-yl]-amide
Adamantane-1-carboxylic acid [7-(4-benzyloxy-3-methoxy-benzyl)-5,6,7,8-tetrahydro-pyrido[3,4-d]pyrimidin-4-yl]-amide;
Adamantane-1-carboxylic acid [7-(2,3-dihydro-benzo[1,4]dioxin-6-ylmethyl)-5,6,7,8-tetrahydro-pyrido[3,4-d]pyrimidin-4-yl]-amide;
Adamantane-1-carboxylic acid [7-(3,4-dichloro-benzyl)-5,6,7,8-tetrahydro-pyrido[3,4-d]pyrimidin-4-yl]-amide;
Adamantane-1-carboxylic acid [7-(2,3-dimethoxy-benzyl)-5,6,7,8-tetrahydro-pyrido[3,4-d]pyrimidin-4-yl]-amide;
Adamantane-1-carboxylic acid [7-(3-benzyloxy-4-methoxy-benzyl)-5,6,7,8-tetrahydro-pyrido[3,4-d]pyrimidin-4-yl]-amide;
Adamantane-1-carboxylic acid [7-(3-hydroxy-4-methoxy-benzyl)-5,6,7,8-tetrahydro-pyrido[3,4-d]pyrimidin-4-yl]-amide;
Adamantane-1-carboxylic acid [7-(3-bromo-4,5-dimethoxy-benzyl)-5,6,7,8-tetrahydro-pyrido[3,4-d]pyrimidin-4-yl]-amide;
Adamantane-1-carboxylic acid [7-(3-cyano-4-fluoro-benzyl)-5,6,7,8-tetrahydro-pyrido[3,4-d]pyrimidin-4-yl]-amide;
Adamantane-1-carboxylic acid (7-benzo[1,3]dioxol-4-ylmethyl-5,6,7,8-tetrahydro-pyrido[3,4-d]pyrimidin-4-yl)-amide;
Adamantane-1-carboxylic acid [7-(4-bromo-benzyl)-5,6,7,8-tetrahydro-pyrido[3,4-d]pyrimidin-4-yl]-amide;
Adamantane-1-carboxylic acid [7-(3-chloro-benzyl)-5,6,7,8-tetrahydro-pyrido[3,4-d]pyrimidin-4-yl]-amide;
Adamantane-1-carboxylic acid [7-(6-chloro-benzo[1,3]dioxol-5-ylmethyl)-5,6,7,8-tetrahydro-pyrido[3,4-d]pyrimidin-4-yl]-amide;
Adamantane-1-carboxylic acid [7-(2,2-dimethyl-propyl)-5,6,7,8-tetrahydro-pyrido[3,4-d]pyrimidin-4-yl]-amide;
Adamantane-1-carboxylic acid [7-(4-chloro-benzyl)-5,6,7,8-tetrahydro-pyrido[3,4-d]pyrimidin-4-yl]-amide;
Adamantane-1-carboxylic acid [7-(4-methyl-benzyl)-5,6,7,8-tetrahydro-pyrido[3,4-d]pyrimidin-4-yl]-amide
Adamantane-1-carboxylic acid [7-(4-cyano-benzyl)-5,6,7,8-tetrahydro-pyrido[3,4-d]pyrimidin-4-yl]-amide;
Adamantane-1-carboxylic acid [7-(4-trifluoromethyl-benzyl)-5,6,7,8-tetrahydro-pyrido[3,4-d]pyrimidin-4-yl]-amide;
Adamantane-1-carboxylic acid [7-(3-fluoro-benzyl)-5,6,7,8-tetrahydro-pyrido[3,4-d]pyrimidin-4-yl]-amide;
Adamantane-1-carboxylic acid [7-(3-methyl-benzyl)-5,6,7,8-tetrahydro-pyrido[3,4-d]pyrimidin-4-yl]-amide;
Adamantane-1-carboxylic acid [7-(4-fluoro-benzyl)-5,6,7,8-tetrahydro-pyrido[3,4-d]pyrimidin-4-yl]-amide;
Adamantane-1-carboxylic acid [7-(2,4-dimethoxy-benzyl)-5,6,7,8-tetrahydro-pyrido[3,4-d]pyrimidin-4-yl]-amide;
Adamantane-1-carboxylic acid [7-(2,4-difluoro-benzyl)-5,6,7,8-tetrahydro-pyrido[3,4-d]pyrimidin-4-yl]-amide;
Adamantane-1-carboxylic acid [7-pyridin-4-ylmethyl-5,6,7,8-tetrahydro-pyrido[3,4-d]pyrimidin-4-yl]-amide;
Adamantane-1-carboxylic acid [7-(4-chloro-3-fluoro-benzyl)-5,6,7,8-tetrahydro-pyrido[3,4-d]pyrimidin-4-yl]-amide;
Adamantane-1-carboxylic acid [7-(2-fluoro-4-trifluoromethyl-benzyl)-5,6,7,8-tetrahydro-pyrido[3,4-d]pyrimidin-4-yl]-amide;
Adamantane-1-carboxylic acid [7-(6-bromo-pyridin-3-ylmethyl)-5,6,7,8-tetrahydro-pyrido[3,4-d]pyrimidin-4-yl]-amide;
Adamantane-1-carboxylic acid [7-(3-bromo-benzyl)-5,6,7,8-tetrahydro-pyrido[3,4-d]pyrimidin-4-yl]-amide;
Adamantane-1-carboxylic acid [7-(2-methoxy-benzyl)-5,6,7,8-tetrahydro-pyrido[3,4-d]pyrimidin-4-yl]-amide;
Adamantane-1-carboxylic acid [7-(4-acetylamino-benzyl)-5,6,7,8-tetrahydro-pyrido[3,4-d]pyrimidin-4-yl]-amide;
Adamantane-1-carboxylic acid [7-(2-bromo-benzyl)-5,6,7,8-tetrahydro-pyrido[3,4-d]pyrimidin-4-yl]-amide
Adamantane-1-carboxylic acid [7-(5-bromo-2-fluoro-benzyl)-5,6,7,8-tetrahydro-pyrido[3,4-d]pyrimidin-4-yl]-amide
Adamantane-1-carboxylic acid (7-cyclopentylmethyl-5,6,7,8-tetrahydro-pyrido[3,4-d]pyrimidin-4-yl)-amide;
Adamantane-1-carboxylic acid [7-(4-trifluoromethoxy-benzyl)-5,6,7,8-tetrahydro-pyrido[3,4-d]pyrimidin-4-yl]-amide;
Adamantane-1-carboxylic acid [7-(4-difluoromethoxy-benzyl)-5,6,7,8-tetrahydro-pyrido[3,4-d]pyrimidin-4-yl]-amide;
Adamantane-1-carboxylic acid {7-[4-(4-fluoro-benzyloxy)-benzyl]-5,6,7,8-tetrahydro-pyrido[3-4-d]pyrimidin-4-yl}-amide;
Adamantane-1-carboxylic acid [7-(2-fluoro-4,5-dimethoxy-benzyl)-5,6,7,8-tetrahydro-pyrido[3,4-d]pyrimidin-4-yl]-amide;
Adamantane-1-carboxylic acid [7-(2,6-difluoro-4-methoxy-benzyl)-5,6,7,8-tetrahydro-pyrido[3,4-d]pyrimidin-4-yl]-amide;
Adamantane-1-carboxylic acid [7-(3-ethoxy-benzyl)-5,6,7,8-tetrahydro-pyrido[3,4-d]pyrimidin-4-yl]-amide
Adamantane-1-carboxylic acid {7-[3-(3-trifluoromethyl-phenoxy)-benzyl]-5,6,7,8-tetrahydro-pyrido[3,4-d]pyrimidin-4-yl}-amide;
Adamantane-1-carboxylic acid [7-(2,2-difluoro-benzo[1,3]dioxol-5-ylmethyl)-5,6,7,8-tetrahydro-pyrido[3,4-d]pyrimidin-4-yl]-amide;
Adamantane-1-carboxylic acid [7-(2-fluoro-5-methoxy-benzyl)-5,6,7,8-tetrahydro-pyrido[3,4-d]pyrimidin-4-yl]-amide;
Adamantane-1-carboxylic acid [7-(4-fluoro-3-methoxy-benzyl)-5,6,7,8-tetrahydro-pyrido[3,4-d]pyrimidin-4-yl]-amide;
Adamantane-1-carboxylic acid [7-(4-ethoxy-benzyl)-5,6,7,8-tetrahydro-pyrido[3,4-d]pyrimidin-4-yl]-amide;
Adamantane-1-carboxylic acid [7-(2,5-dimethoxy-benzyl)-5,6,7,8-tetrahydro-pyrido[3,4-d]pyrimidin-4-yl]-amide;
Adamantane-1-carboxylic acid [7-(3-trifluoromethoxy-benzyl)-5,6,7,8-tetrahydro-pyrido[3,4-d]pyrimidin-4-yl]-amide;
Adamantane-1-carboxylic acid [7-(3,5-dimethoxy-benzyl)-5,6,7,8-tetrahydro-pyrido[3,4-d]pyrimidin-4-yl]-amide;
Adamantane-1-carboxylic acid [7-(6-chloro-pyridin-3-ylmethyl)-5,6,7,8-tetrahydro-pyrido[3,4-d]pyrimidin-4-yl]-amide; and
Adamantane-1-carboxylic acid [7-(4-chloro-2-fluoro-benzyl)-5,6,7,8-tetrahydro-pyrido[3,4-d]pyrimidin-4-yl]-amide. |

* * * * *